(12) United States Patent
Manoharan et al.

(10) Patent No.: US 9,566,340 B2
(45) Date of Patent: Feb. 14, 2017

(54) MONOMERS AND OLIGONUCLEOTIDES COMPRISING CYCLOADDITION ADDUCT(S)

(71) Applicant: Alnylam Pharmaceuticals, Inc., Cambridge, MA (US)

(72) Inventors: Muthiah Manoharan, Cambridge, MA (US); Jayaprakash K. Nair, Cambridge, MA (US); Kallanthottahil G. Rajeev, Cambridge, MA (US); Michael E. Jung, Cambridge, MA (US)

(73) Assignee: Alnylam Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 14/918,022

(22) Filed: Oct. 20, 2015

(65) Prior Publication Data

US 2016/0101189 A1    Apr. 14, 2016

Related U.S. Application Data

(62) Division of application No. 13/575,461, filed as application No. PCT/US2011/022975 on Jan. 28, 2011, now Pat. No. 9,198,972.

(Continued)

(51) Int. Cl.
| | |
|---|---|
| *A01N 43/04* | (2006.01) |
| *A61K 31/70* | (2006.01) |
| *C12N 15/11* | (2006.01) |
| *C07H 23/00* | (2006.01) |
| *C07H 17/02* | (2006.01) |
| *A61K 47/48* | (2006.01) |
| *C07D 249/16* | (2006.01) |

(Continued)

(52) U.S. Cl.
CPC ..... *A61K 47/48092* (2013.01); *A61K 31/7088* (2013.01); *A61K 31/711* (2013.01); *A61K 31/713* (2013.01); *A61K 47/48169* (2013.01); *A61K 47/48176* (2013.01); *C07D 249/16* (2013.01); *C07D 471/04* (2013.01); *C07D 487/04* (2013.01); *C07D 493/04* (2013.01); *C07D 493/08* (2013.01); *C07D 495/04* (2013.01); *C07D 495/08* (2013.01); *C07F 9/5725* (2013.01); *C07F 9/65515* (2013.01); *C07F 9/65586* (2013.01); *C07H 19/067* (2013.01)

(58) Field of Classification Search
CPC ............ C07H 19/067; A61K 47/48092; A61K 47/48169; A61K 47/48176; C07D 493/04; C07D 249/16; C07D 487/04; C07D 493/08; C07D 495/04; C07D 495/08; C07D 471/04; C07F 9/5725; C07F 9/65515; C07F 9/65586

See application file for complete search history.

(56) References Cited

U.S. PATENT DOCUMENTS

| | | | |
|---|---|---|---|
| 7,767,421 | B2 | 8/2010 | Gee et al. |
| 7,910,335 | B2 | 3/2011 | Salic et al. |

(Continued)

OTHER PUBLICATIONS

Wilson et al., "Noncovalent Cell Surface Engineering with Cationic Graft Copolymers," Journal of the American Chemical Society 131(51):18228-18229 (2009).

(Continued)

*Primary Examiner* — Lawrence E Crane
(74) *Attorney, Agent, or Firm* — Jeffrey N. Townes; LeClairRyan

(57) ABSTRACT

The invention features compounds of formula V or XII:

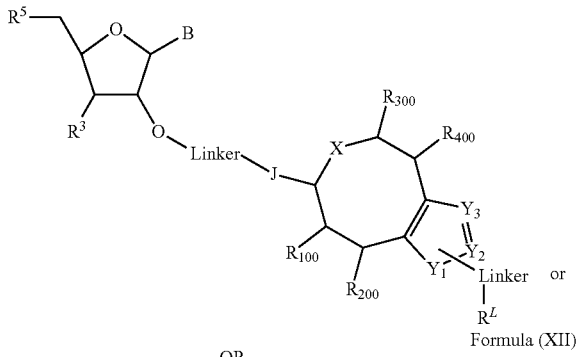

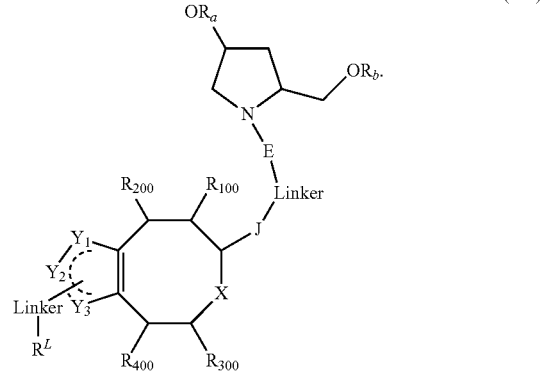

In one embodiment, the invention relates compounds and processes for conjugating ligand to oligonucleotide. The invention further relates to methods for treating various disorders and diseases such as viral infections, bacterial infections, parasitic infections, cancers, allergies, autoimmune diseases, immunodeficiencies and immunosuppression.

12 Claims, 22 Drawing Sheets

Related U.S. Application Data

(60) Provisional application No. 61/299,296, filed on Jan. 28, 2010, provisional application No. 61/405,980, filed on Oct. 22, 2010.

(51) Int. Cl.

| | | |
|---|---|---|
| C07D 471/04 | (2006.01) |
| C07D 487/04 | (2006.01) |
| C07D 493/04 | (2006.01) |
| C07D 493/08 | (2006.01) |
| C07D 495/04 | (2006.01) |
| C07D 495/08 | (2006.01) |
| C07F 9/572 | (2006.01) |
| C07F 9/655 | (2006.01) |
| C07F 9/6558 | (2006.01) |
| C07H 19/067 | (2006.01) |
| A61K 31/7088 | (2006.01) |
| A61K 31/711 | (2006.01) |
| A61K 31/713 | (2006.01) |

(56) References Cited

U.S. PATENT DOCUMENTS

| | | |
|---|---|---|
| 8,541,570 B2 | 9/2013 | Gee et al. |
| 8,859,753 B2 | 10/2014 | Salic et al. |
| 9,198,972 B2 * | 12/2015 | Manoharan ...... A61K 47/48092 |
| 2007/0099222 A1 | 5/2007 | Gee et al. |
| 2007/0207476 A1 | 9/2007 | Salic et al. |
| 2012/0035115 A1 | 2/2012 | Manoharan et al. |

OTHER PUBLICATIONS

Ning et al., "Visualizing Metabolically Labeled Glycoconjugates of Living Cells by Copper-Free and Fast Huisgen Cycloadditions," Angewandte Chemie 47(12):2253-2255 (2008).

Gutsmiedl et al., "Copper-Free "Click" Modification of DNA via Nitrile Oxide-Norbornene 1,3-Dipolar Cycloaddition," Organic Letters 11(11):2405-2408 (2009).

Jewett et al., "Cu-Free Click Cycloaddition Reactions in Chemical Biology," Chemical Society Reviews 39 (4):1272-1279 (2010).

Jao et al., "Exploring RNA Transcription and Turnover in Vivo by Using Click Chemistry," Proceedings of the National Academy of Sciences of the United States of America 105(41):15779-15784 (2008).

Best, "Click Chemistry and Bioorthogonal Reactions: Unprecedented Selectivity in the Labeling of Biological Molecules," Biochemistry 48(28):6571-6584 (2009).

Jayaprakash et al., "Non-Nucleoside Building Blocks for Copper-Assisted and Copper-Free Click Chemistry for the Efficient Synthesis of RNA Conjugates," Organic Letters 12(23):5410-5413 (2010).

* cited by examiner (c)

SEQUENCE LISTING

```
<160> NUMBER OF SEQ ID NOS: 34

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

```
Ala Ala Leu Glu Ala Leu Ala Glu Ala Leu Ala Glu Ala Leu Glu Ala
1               5                   10                  15

Leu Glu Ala Leu Ala Glu Ala Ala Ala Gly Gly Cys
            20                  25

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Ala Leu Ala Glu Ala Leu Ala Glu Ala Leu Ala Glu Ala Leu Ala
1               5                   10                  15

Glu Ala Leu Ala Glu Ala Leu Ala Ala Ala Gly Gly Cys
            20                  25                  30

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Leu Glu Ala Leu Ala Glu Ala Leu Glu Ala Leu Ala Glu Ala
1               5                   10                  15

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Leu Phe Glu Ala Ile Glu Gly Phe Ile Glu Asn Gly Trp Glu Gly
1               5                   10                  15

Met Ile Trp Asp Tyr Gly
            20

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
```

```
                                    peptide

<400> SEQUENCE: 6

Gly Leu Phe Glu Ala Ile Glu Gly Phe Ile Glu Asn Gly Trp Glu Gly
1               5                   10                  15

Met Ile Asp Gly Trp Tyr Gly Cys
            20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Leu Phe Glu Ala Ile Glu Gly Phe Ile Glu Asn Gly Trp Glu Gly
1               5                   10                  15

Met Ile Asp Gly Gly Cys
            20

<210> SEQ ID NO 8
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Leu Phe Gly Ala Leu Ala Glu Ala Leu Ala Glu Ala Leu Ala Glu
1               5                   10                  15

His Leu Ala Glu Ala Leu Ala Glu Ala Leu Glu Ala Leu Ala Ala Gly
            20                  25                  30

Gly Ser Cys
        35

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
            20                  25                  30

Ser Cys

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Norleucine
```

```
<400> SEQUENCE: 10

Gly Leu Phe Glu Ala Ile Glu Gly Phe Ile Glu Asn Gly Trp Glu Gly
1               5                   10                  15

Leu Ile Asp Gly Lys
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Norleucine

<400> SEQUENCE: 11

Gly Leu Phe Glu Ala Ile Glu Gly Phe Ile Glu Asn Gly Trp Glu Gly
1               5                   10                  15

Leu Ile Asp Gly
            20

<210> SEQ ID NO 12
<211> LENGTH: 16
<212> TYPE: PRT
<213> ORGANISM: Unknown
<220> FEATURE:
<223> OTHER INFORMATION: Description of Unknown: Penetratin cell
      permeation peptide

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 13
<212> TYPE: PRT
<213> ORGANISM: Human immunodeficiency virus

<400> SEQUENCE: 13

Gly Arg Lys Lys Arg Arg Gln Arg Arg Arg Pro Pro Gln
1               5                   10

<210> SEQ ID NO 14
<211> LENGTH: 27
<212> TYPE: PRT
<213> ORGANISM: Unknown
<220> FEATURE:
<223> OTHER INFORMATION: Description of Unknown: Signal sequence-based
      cell permeation peptide

<400> SEQUENCE: 14

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 15
<211> LENGTH: 18
<212> TYPE: PRT
<213> ORGANISM: Unknown
<220> FEATURE:
<223> OTHER INFORMATION: Description of Unknown: PVEC cell permeation
      peptide
```

<400> SEQUENCE: 15

Leu Leu Ile Ile Leu Arg Arg Arg Ile Arg Lys Gln Ala His Ala His
1               5                   10                  15

Ser Lys

<210> SEQ ID NO 16
<211> LENGTH: 26
<212> TYPE: PRT
<213> ORGANISM: Unknown
<220> FEATURE:
<223> OTHER INFORMATION: Description of Unknown: Transportan cell
      permeation peptide

<400> SEQUENCE: 16

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 17
<211> LENGTH: 18
<212> TYPE: PRT
<213> ORGANISM: Unknown
<220> FEATURE:
<223> OTHER INFORMATION: Description of Unknown: Amphiphilic model cell
      permeation peptide

<400> SEQUENCE: 17

Lys Leu Ala Leu Lys Leu Ala Leu Lys Ala Leu Lys Ala Ala Leu Lys
1               5                   10                  15

Leu Ala

<210> SEQ ID NO 18
<211> LENGTH: 9
<212> TYPE: PRT
<213> ORGANISM: Unknown
<220> FEATURE:
<223> OTHER INFORMATION: Description of Unknown: Arg9 cell permeation
      peptide

<400> SEQUENCE: 18

Arg Arg Arg Arg Arg Arg Arg Arg Arg
1               5

<210> SEQ ID NO 19
<211> LENGTH: 10
<212> TYPE: PRT
<213> ORGANISM: Unknown
<220> FEATURE:
<223> OTHER INFORMATION: Description of Unknown: Bacterial cell wall
      permeation peptide

<400> SEQUENCE: 19

Lys Phe Phe Lys Phe Phe Lys Phe Phe Lys
1               5                   10

<210> SEQ ID NO 20
<211> LENGTH: 37
<212> TYPE: PRT
<213> ORGANISM: Unknown
<220> FEATURE:
<223> OTHER INFORMATION: Description of Unknown: LL-37 cell permeation
      peptide

<400> SEQUENCE: 20

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35
```

```
<210> SEQ ID NO 21
<211> LENGTH: 31
<212> TYPE: PRT
<213> ORGANISM: Unknown
<220> FEATURE:
<223> OTHER INFORMATION: Description of Unknown: Cecropin P1 cell
      permeation peptide

<400> SEQUENCE: 21
```

```
Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
                20                  25                  30
```

```
<210> SEQ ID NO 22
<211> LENGTH: 30
<212> TYPE: PRT
<213> ORGANISM: Unknown
<220> FEATURE:
<223> OTHER INFORMATION: Description of Unknown: Alpha-defensin cell
      permeation peptide

<400> SEQUENCE: 22
```

```
Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30
```

```
<210> SEQ ID NO 23
<211> LENGTH: 36
<212> TYPE: PRT
<213> ORGANISM: Unknown
<220> FEATURE:
<223> OTHER INFORMATION: Description of Unknown: B-defensin cell
      permeation peptide

<400> SEQUENCE: 23
```

```
Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
                20                  25                  30

Lys Cys Cys Lys
            35
```

```
<210> SEQ ID NO 24
<211> LENGTH: 12
<212> TYPE: PRT
<213> ORGANISM: Unknown
<220> FEATURE:
<223> OTHER INFORMATION: Description of Unknown: Bactenecin cell
      permeation peptide

<400> SEQUENCE: 24
```

```
Arg Lys Cys Arg Ile Val Val Ile Arg Val Cys Arg
1               5                   10
```

```
<210> SEQ ID NO 25
<211> LENGTH: 42
<212> TYPE: PRT
<213> ORGANISM: Unknown
<220> FEATURE:
<223> OTHER INFORMATION: Description of Unknown: PR-39 cell permeation
      peptide

<400> SEQUENCE: 25

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 26
<211> LENGTH: 13
<212> TYPE: PRT
<213> ORGANISM: Unknown
<220> FEATURE:
<223> OTHER INFORMATION: Description of Unknown: Indolicidin cell
      permeation peptide

<400> SEQUENCE: 26

Ile Leu Pro Trp Lys Trp Pro Trp Trp Pro Trp Arg Arg
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ala Val Ala Leu Leu Pro Ala Val Leu Leu Ala Leu Leu Ala Pro
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ala Leu Leu Pro Val Leu Leu Ala Ala Pro
1               5                   10

<210> SEQ ID NO 29
<211> LENGTH: 16
<212> TYPE: PRT
<213> ORGANISM: Drosophila sp.

<400> SEQUENCE: 29

Arg Gln Ile Lys Ile Trp Phe Gln Asn Arg Arg Met Lys Trp Lys Lys
1               5                   10                  15

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 30

Tyr Gly Arg Lys Lys Arg Arg Gln Arg Arg Pro Pro Gln
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Arg Gly Asp Lys
1               5

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 5'-alkyne-RNA base
<220> FEATURE:
<223> OTHER INFORMATION: see specification as filed for detailed
      description of actual embodiment

<400> SEQUENCE: 32
ncuuacgcug aguacuucga tt                                          22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (22)..(22)
<223> OTHER INFORMATION: 3'-alkyne-RNA base
<220> FEATURE:
<223> OTHER INFORMATION: see specification as filed for detailed
      description of actual embodiment

<400> SEQUENCE: 33
cuuacgcuga guacuucgat tn                                          22

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:

```
<221> NAME/KEY: modified_base
<222> LOCATION: (12)..(12)
<223> OTHER INFORMATION: Internal-alkyne-RNA base
<220> FEATURE:
<223> OTHER INFORMATION: see specification as filed for detailed
      description of actual embodiment

<400> SEQUENCE: 34
cuuacgcuga gnacuucgat t                                          21
```

MONOMERS AND OLIGONUCLEOTIDES COMPRISING CYCLOADDITION ADDUCT(S)

PRIORITY CLAIM

This application is divisional application of U.S. patent application Ser. No. 13/575,461, filed Oct. 17, 2012, which claims priority to PCT Application No. PCT/US2011/022975, filed Jan. 28, 2011, which claims priority to U.S. Provisional Application No. 61/405,980, filed Oct. 22, 2010 and U.S. Provisional Application No. 61/299,296, filed Jan. 28, 2010, all of which are hereby incorporated by reference in their entirety.

FIELD OF INVENTION

The present invention relates to the field of conjugation of ligands to oligonucleotides with copper free cycloaddition chemistry.

BACKGROUND

Oligonucleotide compounds have important therapeutic applications in medicine. Oligonucleotides can be used to silence genes that are responsible for a particular disease. Gene-silencing prevents formation of a protein by inhibiting translation. Importantly, gene-silencing agents are a promising alternative to traditional small, organic compounds that inhibit the function of the protein linked to the disease. siRNA, antisense RNA, and micro-RNA are oligonucleotides that prevent the formation of proteins by gene-silencing.

RNA interference or "RNAi" is a term initially coined by Fire and co-workers to describe the observation that double-stranded RNA (dsRNA) can block gene expression (Fire et al. (1998) Nature 391, 806-811; Elbashir et al. (2001) Genes Dev. 15, 188-200). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown.

siRNA compounds are promising agents for a variety of diagnostic and therapeutic purposes. siRNA compounds can be used to identify the function of a gene. In addition, siRNA compounds offer enormous potential as a new type of pharmaceutical agent which acts by silencing disease-causing genes. Research is currently underway to develop interference RNA therapeutic agents for the treatment of many diseases including central-nervous-system diseases, inflammatory diseases, metabolic disorders, oncology, infectious diseases, and ocular disease.

Despite the different synthetic strategies developed for conjugation of various ligands to the oligonucleotides, the synthesis of ligand-oligonucleotide conjugates is anything but trivial and requires extensive expertise in organic chemistry and solid-phase synthesis. A real advance would be to use a coupling reaction that can be utilized for a large variety of ligands and oligonucleotides. The Huisgen 1,3-dipolar cycloaddition of alkynes and azides, the "click" reaction, is especially attractive for irreversible coupling of two molecules under mild conditions. The "click" chemistry has recently emerged as an efficient strategy to conjugate carbohydrates, peptides and proteins, fluorescent labels and lipids to oligonucleotides. Therefore, there is a clear need for new reagents that can be utilize for "click" chemistry for conjugation of ligands to oligonucleotides. The present invention is directed to this very important end.

SUMMARY

The invention relates to compounds that can be used as a ribose replacement or can be used as universal base to conjugate various ligands to oligonucleotides, e.g. iRNA agents, through "copper free click" chemistry. These compounds are also referred to as the "click-carrier" herein.

In one aspect, the invention features, a compound having the structure shown in formula (I)

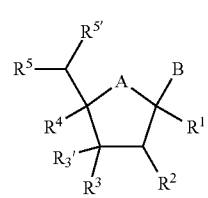

Formula (I)

wherein:

A is O, S, $NR^N$ or $CR^P{}_2$;

B is independently for each occurrence hydrogen, optionally substituted natural or non-natural nucleobase, optionally substituted triazole, optionally substituted tetrazole, $R^6$, NH—C(O)—O—C(CH$_2$B$_1$)$_3$, NH—C(O)—NH—C(CH$_2$B$_1$)$_3$, where B$_1$ is halogen, mesylate, optionally substituted triazole, optionally substituted tetrazole, or $R^6$;

$R^1$, $R^2$, $R^3$, $R^4$ and $R^5$ are each independently for each occurrence H, $OR^7$, F, $N(R^N)_2$, $N_3$, CN, -J-linker-$N_3$, -J-linker-CN, -J-linker-$R^8$, -J-linker-cycloalkyne, -J-linker-$R_L$, -J-Q-linker-$R^L$ or -J-linker-Q-linker-$R^L$;

$R^{3'}$ is H or OH;

$R^{5'}$ is independently for each occurrence H, halogen, optionally substituted alkyl, optionally substituted alkenyl, or optionally substituted alkynyl, J is absent, O, S, $NR^N$, OC(O)NH, NHC(O)O, C(O)NH, NHC(O), NHSO, NHSO$_2$, NHSO$_2$NH, OC(O), C(O)O, OC(O)O, NHC(O)NH, NHC(S)NH, OC(S)NH, O—N=CH, OP(N(R$^N$)$_2$)O, or OP(N(R$^N$)$_2$);

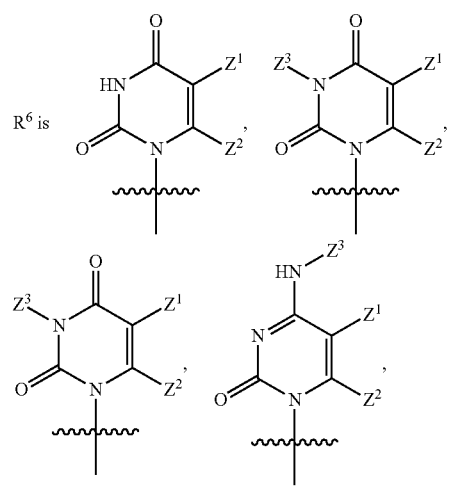

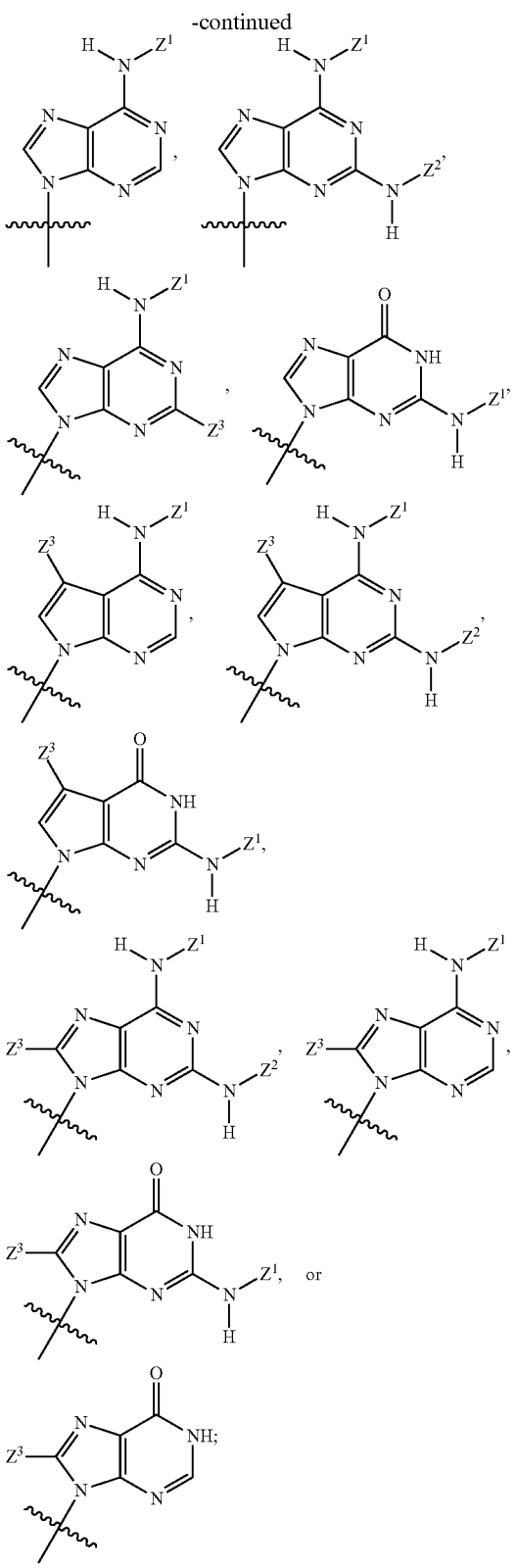

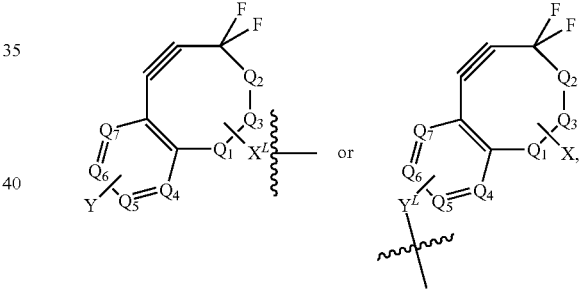

a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P(Z$^1$)(Z$^2$)—O-nucleoside, —P(Z$^4$)(Z$^5$)—O-oligonucleotide, —P(Z$^4$)(Z$^5$)-formula (I), —P(Z$^4$)(O-linker-Q-linker-R$^L$)—O-nucleoside, —P(Z$^4$)(O-linker-N$_3$)—O-nucleoside, P(Z$^4$)(O-linker-CN)—O-nucleoside, P(Z$^4$)(O-linker-R$^8$)—O-nucleoside, P(Z$^4$)(O-linker-cycloalkyne)-O-nucleoside, —P(Z$^4$)(O-linker-R$^L$)—O-oligonucleotide, —P(Z$^4$)(O-linker-Q-linker-R$^L$)—O-oligonucleotide, —P(Z$^4$)(O-linker-R$^L$)—O-oligonucleotide, P(Z$^4$)(O-linker-N$_3$)—O-oligonucleotide, —P(Z$^4$)(O-linker-CN)—O-oligonucleotide, P(Z$^4$)(O-linker-R$^8$)—O-oligonucleotide, P(Z$^4$)(O-linker-cycloalkyne)-O-oligonucleotide, —P(Z$^4$)(-linker-Q-linker-R$^L$)—O-nucleoside, P(Z$^4$)(-linker-R$^L$)—O-nucleoside, —P(Z$^4$)(-linker-N$_3$)—O-nucleoside, P(Z$^4$)(-linker-CN)—O-nucleoside, P(Z$^4$)(-linker-R$^8$)—O-nucleoside, P(Z$^4$)(-linker-cycloalkyne)-O-nucleoside, —P(Z$^4$)(-linker-Q-linker-R$^L$)—O-oligonucleotide, (Z$^4$)(-linker-R$^L$)—O-oligonucleotide, P(Z$^4$)(-linker-N$_3$)—O-oligonucleotide, —P(Z$^4$)(-linker-CN)—O-oligonucleotide, P(Z$^1$)(-linker-R$^8$)—O-oligonucleotide or P(Z$^4$)(-linker-cycloalkyne)-O-oligonucleotide;

R$^8$ is

X$^L$ and Y$^L$ are independently absent, a linker, —(CH$_2$)$_n$O—, —(CH$_2$)$_n$COO—, —(CH$_2$)$_n$N(R$^9$)—, —(CH$_2$)$_n$S—, (CH$_2$)$_n$S—S—, —(CH$_2$)$_n$O—N(R$^9$)—, or —(CH$_2$)$_n$CO—;

X and Y are independently H, a bond, (CH$_2$)$_n$OH, (CH$_2$)$_n$COOH, (CH$_2$)$_n$N(R$^9$)(R$^9$), (CH$_2$)$_n$SH, (CH$_2$)$_n$S—SP-Py, (CH$_2$)$_n$O—N(R$^9$)(R$^9$), (CH$_2$)$_n$CHO, or (CH$_2$)$_n$COR$^{10}$;

Q$^1$, Q$^2$ and Q$^3$ are independently C(R$^P$)$_2$, NR$^9$, O, or S;

Q$^4$, Q$^5$, Q$^6$ and Q$^7$ are independently CR$^P$ or N;

R$^9$, R$^{10}$ and R$^N$ are independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

R$^L$ is hydrogen or a ligand;

R$^P$ is independently for each occurrence H, optionally substituted alkyl, optionally substituted alkenyl, optionally substituted alkynyl, optionally substituted aryl, optionally substituted cycloalkyl, optionally substituted aralkyl or optionally substituted heteroaryl;

R$^7$ is independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), Q is independently for each occurrence

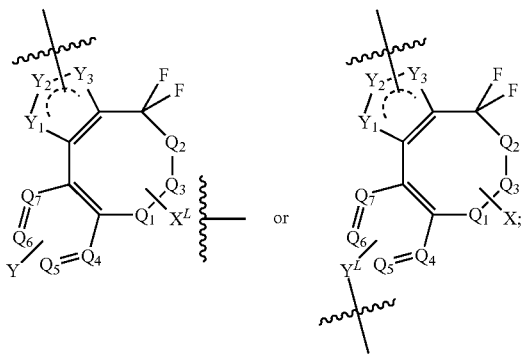

$Y_1$, $Y_2$ and $Y_3$ are independently $CR^P$, N, O, or S;

$Z^1$, $Z^2$ and $Z^3$ are independently H or $R^8$;

$Z^4$ and $Z^5$ are each independently for each occurrence O, S or optionally substituted alkyl;

n is 0-20; and provided that at least one $R^8$ or Q is present.

In one embodiment, the invention features, a compound having the structure shown in formula (II)

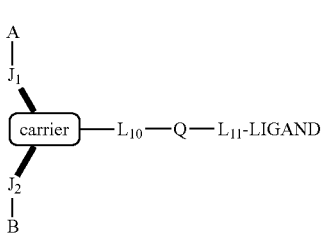

(II)

A and B are independently for each occurrence hydrogen, protecting group, optionally substituted aliphatic, optionally substituted aryl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^4$)($Z^5$)—O-nucleoside, or —P($Z^4$)($Z^5$)—O-oligonucleotide; wherein $Z^4$ and $Z^5$ are each independently for each occurrence O, S or optionally substituted alkyl;

$J_1$ and $J_2$ are independently O, S, $NR^N$, optionally substituted alkyl, OC(O)NH, NHC(O)O, C(O)NH, NHC(O), OC(O), C(O)O, OC(O)O, NHC(O)NH, NHC(S)NH, OC(S) NH, OP(N($R^P$)$_2$)O, or OP(N($R^P$)$_2$);

(carrier) is cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone;

$L_{10}$ and $L_{11}$ are independently absent or a linker;

Q is independently for each occurrence

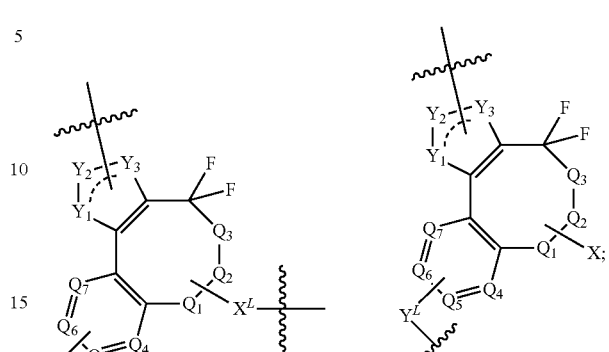

$X^L$ and $Y^L$ are independently absent, a linker, —(CH$_2$)$_n$O—, —(CH$_2$)$_n$COO—, —(CH$_2$)$_n$N(R$^9$)—, —(CH$_2$)$_n$S—, (CH$_2$)$_n$S—S—, —(CH$_2$)$_n$O—N(R$^9$)—, or —(CH$_2$)$_n$CO—;

X and Y are independently H, a bond, (CH$_2$)$_n$OH, (CH$_2$)$_n$COOH, (CH$_2$)$_n$N(R$^9$)(R$^9$), (CH$_2$)$_n$SH, (CH$_2$)$_n$S—SP-Py, (CH$_2$)$_n$O—N(R$^9$)(R$^9$), (CH$_2$)$_n$CHO, or (CH$_2$)$_n$COR$^{10}$;

$R^9$, and $R^{10}$ are independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

$Y_1$, $Y_2$ and $Y_3$ are independently $CR^P$, N, O, or S;

$R^P$ is independently for each occurrence H, optionally substituted alkyl, optionally substituted alkenyl, optionally substituted alkynyl, optionally substituted aryl, optionally substituted cycloalkyl, optionally substituted aralkyl or optionally substituted heteroaryl;

$Q^1$, $Q^2$ and $Q^3$ are independently C($R^P$)$_2$, $NR^9$, O, or S;

$Q^4$, $Q^5$, $Q^6$ and $Q^7$ are independently $CR^P$ or N;

$Z^4$ and $Z^5$ are each independently for each occurrence O, S or optionally substituted alkyl; and n is 0-20.

In another embodiment of the present invention there are disclosed pharmaceutical compositions comprising a therapeutically effective amount of an iRNA agent of the invention in combination with a pharmaceutically acceptable carrier or excipient. In yet another embodiment of the invention describes process for preparing said compounds

BRIEF DESCRIPTION OF THE DRAWINGS

FIG. 1 discloses SEQ ID NO: 32.

FIG. 4 discloses SEQ ID NO: 33.

FIG. 5 discloses SEQ ID NO: 33.

FIG. 6 discloses SEQ ID NO: 34.

FIG. 7 discloses SEQ ID NO: 34.

FIG. 8 discloses SEQ ID NO: 32.

DETAILED DESCRIPTION

In one embodiment of the compounds of the present invention are compounds represented by formula I or II as illustrated above, or a pharmaceutically acceptable salt, ester or prodrug thereof.

Figure 13:
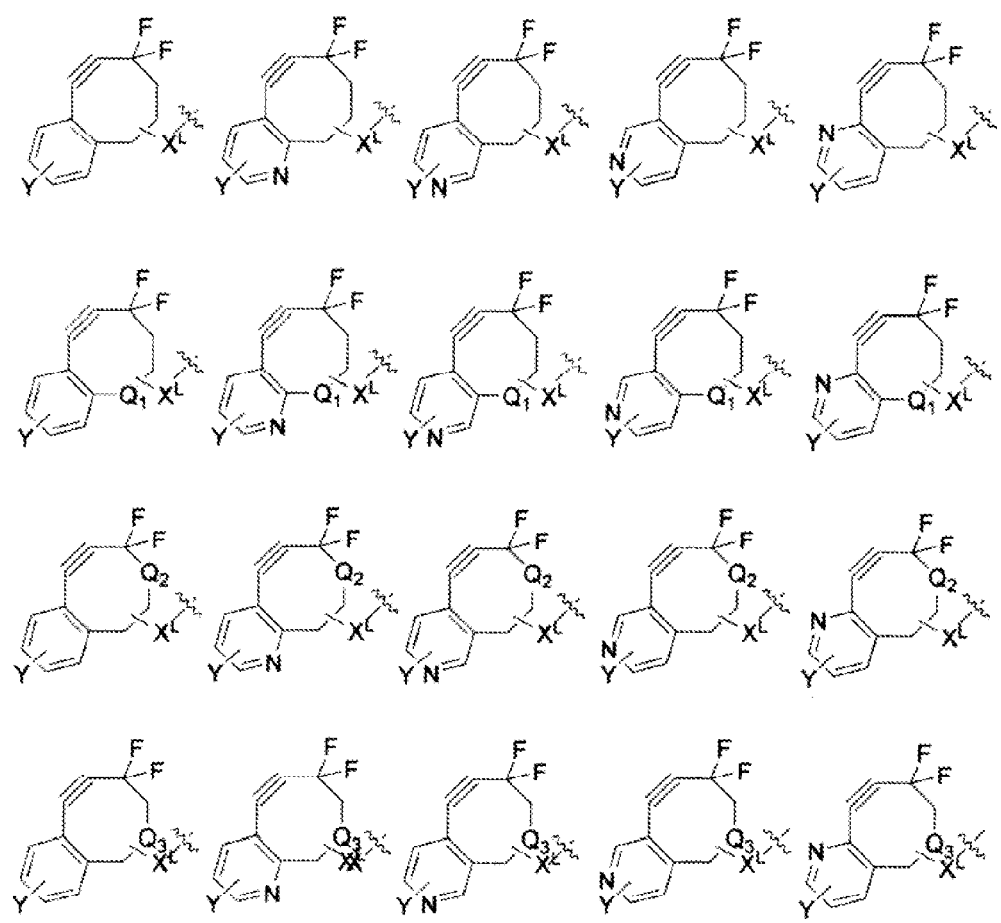
FIGS. 13 and 14 depict some embodiments of $R^8$.
Figure 14:
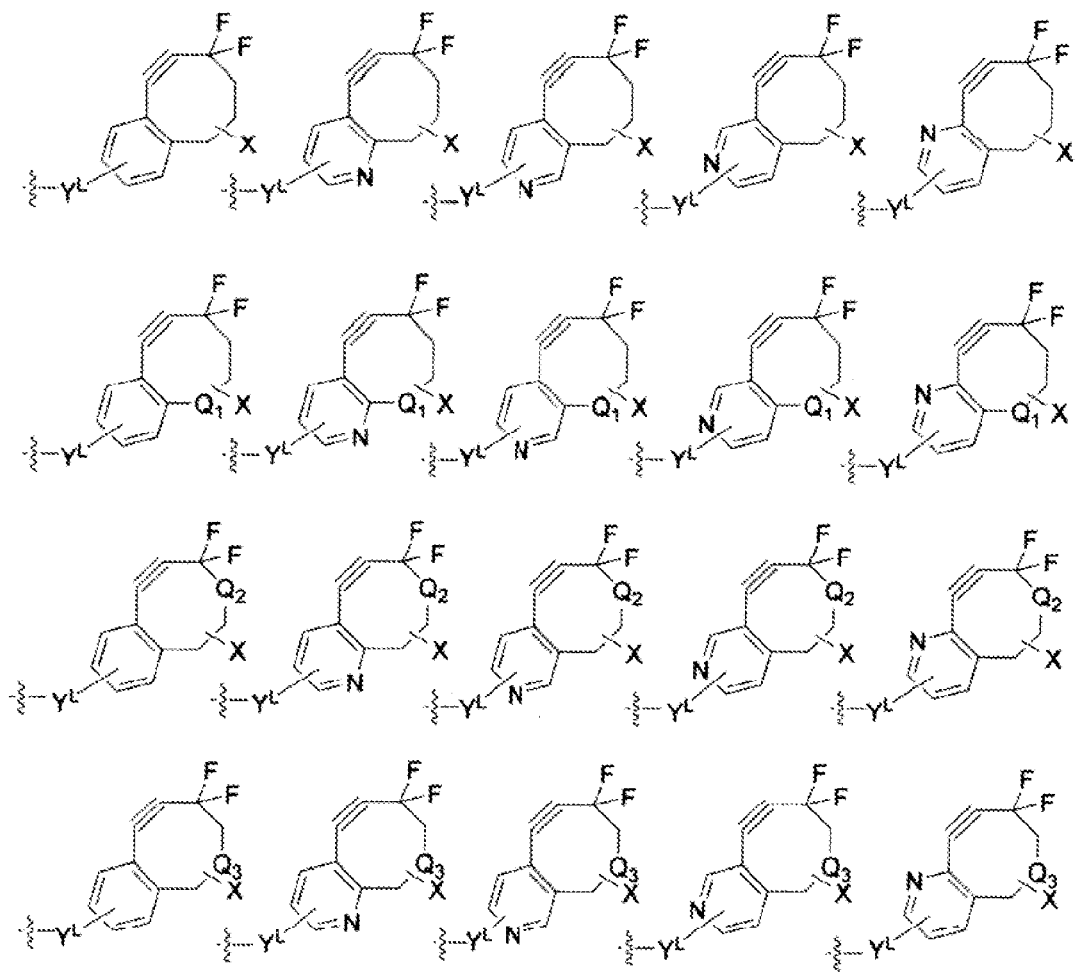

In some embodiments of the compounds described herein, $R^8$ is as shown in FIGS. 13 and 14.

Figure 15:
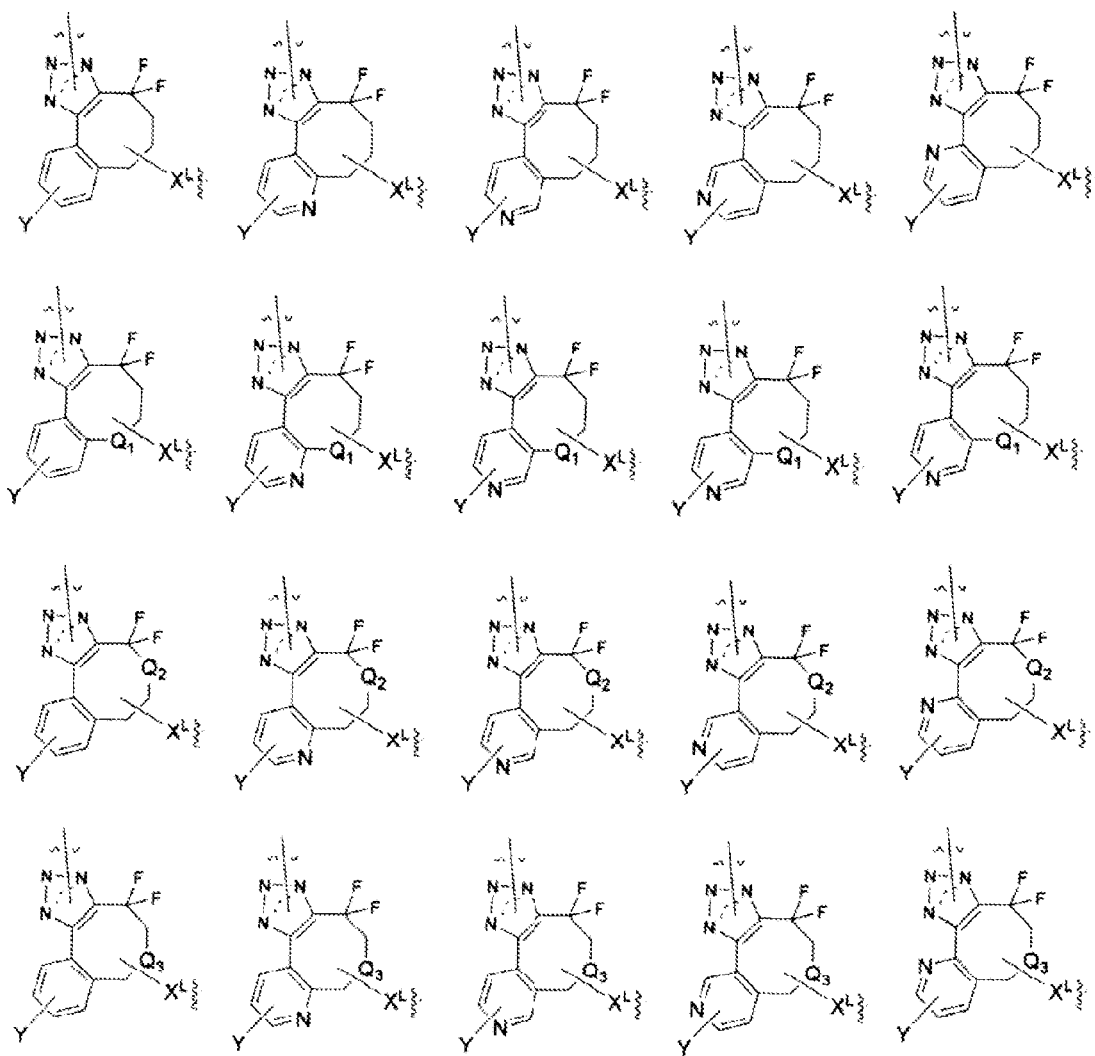
FIGS. 15 and 16 depict some embodiments of Q.
Figure 16:
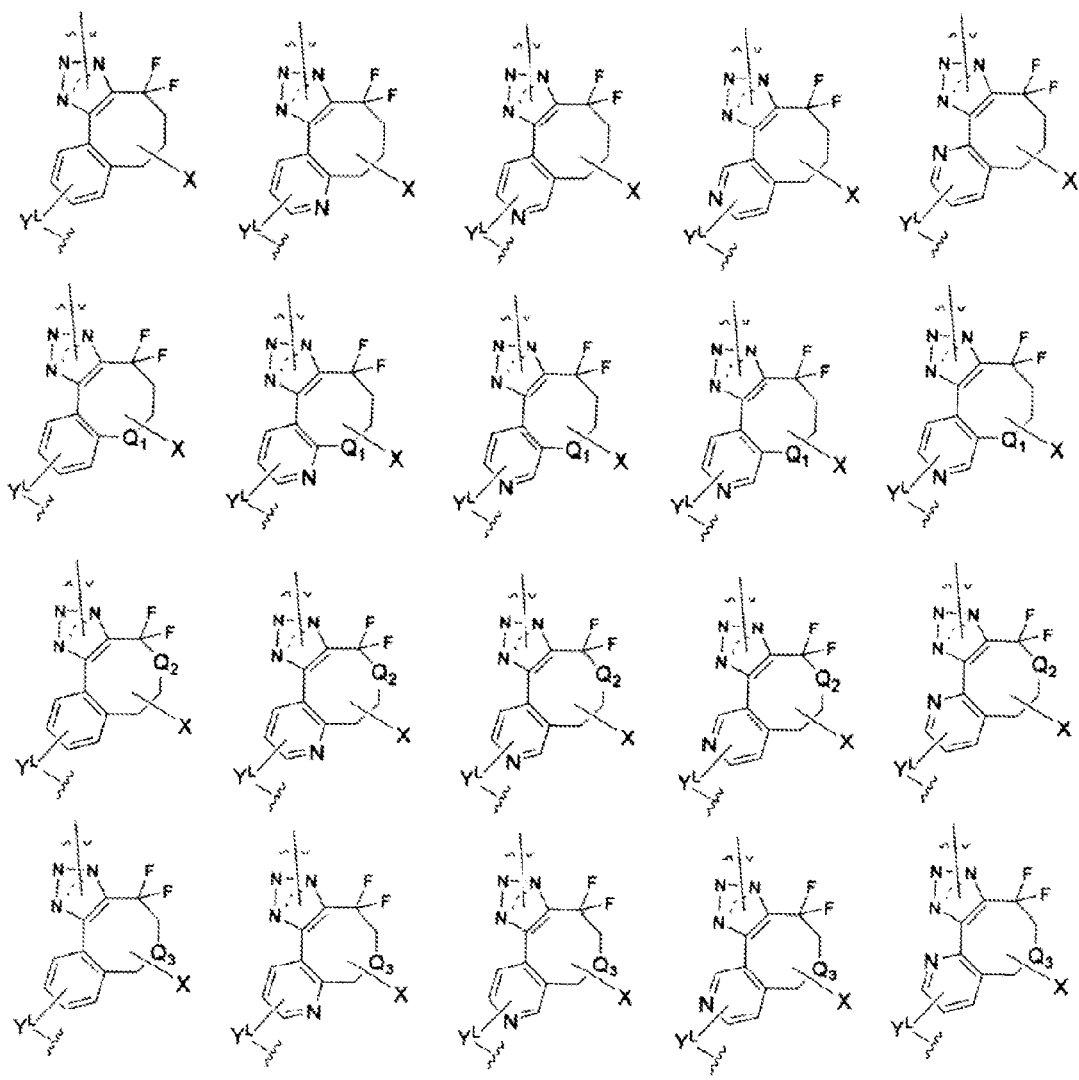

In some embodiments of the compounds described herein, Q is as shown in FIGS. 15 and 16.

In some embodiments of the compounds described herein $Y_1$, $Y_2$ and $Y_3$ are N.

In one embodiment, the invention features a compound having the structure shown in formula (III):

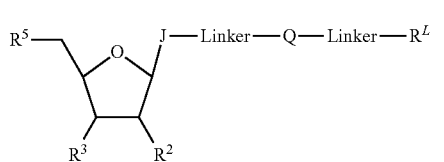

Formula (III)

wherein each linker can be the same or different, and $R^2$, $R^3$, $R^5$, $R^L$ and Q are as defined for the first embodiment.

In one embodiment the invention features a compound having the structure shown in (IIIa) or (IIIb):

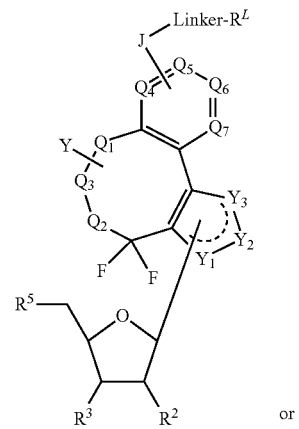

Formula (IIIa)

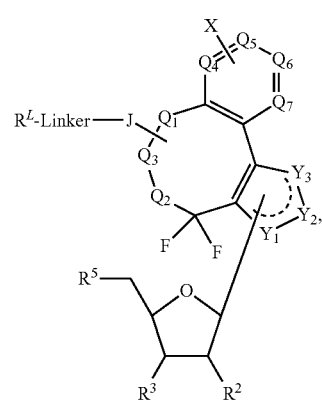

Formula (IIIb)

wherein $R^2$, $R^3$, $R^5$, $R^L$, J, $Q_1$, $Q_2$, $Q_3$, $Q_4$, $Q_5$, $Q_6$, $Q_7$, X, Y, $Y_1$, $Y_2$, and $Y_3$ are as defined in the first embodiment.

In one embodiment, the invention features, a compound having the structure shown in formula (IVa) or (IVb):

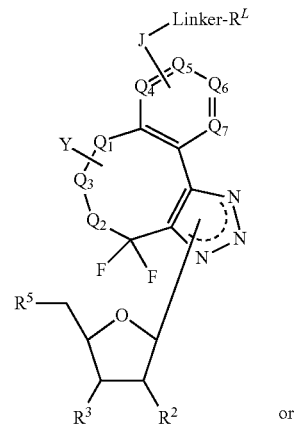

Formula (IVa)

-continued

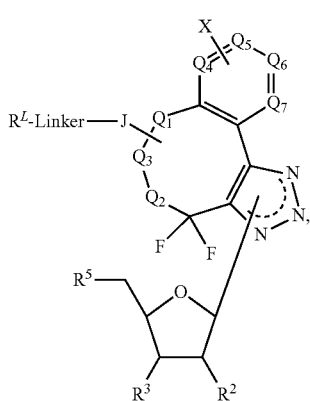

Formula (IVb)

wherein $R^2$, $R^3$, $R^5$, $R^L$, J, $Q_1$, $Q_2$, $Q_3$, $Q_4$, $Q_5$, $Q_6$, $Q_7$, X and Y, are as defined in the first embodiment.

In one embodiment, the invention features, a compound having the structure shown in formula (V):

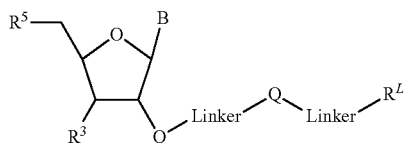

Formula (V)

wherein each linker can be the same or different, and B, $R^3$, $R^5$, $R^L$, and Q are as defined in the first embodiment.

In one embodiment, the invention features, a compound having the structure shown in formula (Va) or (Vb):

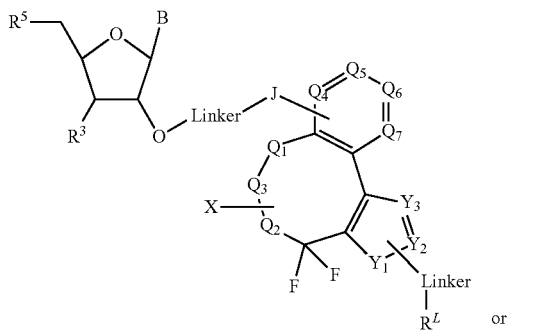

Formula (Vb)

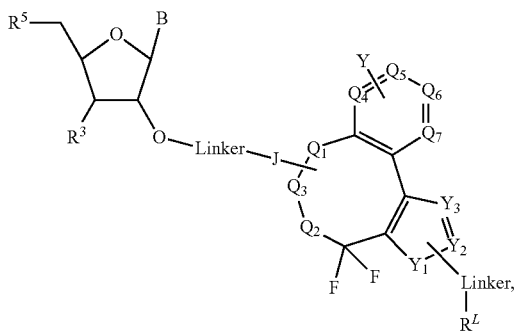

Formula (Va)

wherein B, $R^3$, $R^5$, $R^L$, J, $Q_1$, $Q_2$, $Q_3$, $Q_4$, $Q_5$, $Q_6$, $Q_7$, X, Y, $Y_1$, $Y_2$, and $Y_3$ are as defined in the first embodiment.

In one embodiment, the invention features, a compound having the structure shown in formula (VIa) or (VIb):

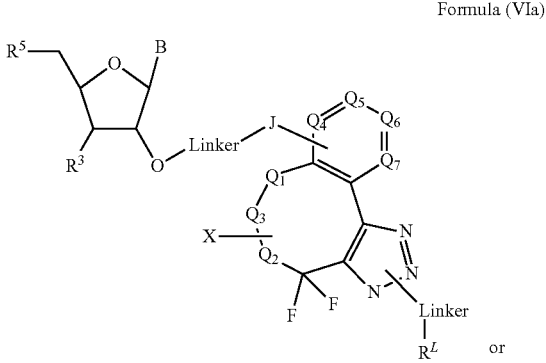

Formula (VIa)

Formula (VIb)

wherein B, $R^3$, $R^5$, $R^L$, J, $Q_1$, $Q_2$, $Q_3$, $Q_4$, $Q_5$, $Q_6$, $Q_7$, X, Y, $Y_1$, $Y_2$, and $Y_3$ are as defined in the first embodiment.

In one embodiment, the invention features, a compound having the structure shown in formula (VII):

Formula (VII)

wherein each linker can be the same or different, and B, $R^2$, $R^5$, $R^L$, and Q are as defined in the first embodiment.

In one embodiment, the invention features, a compound having the structure shown in formula (VIIa) or (VIIb):

Formula (VIIa)

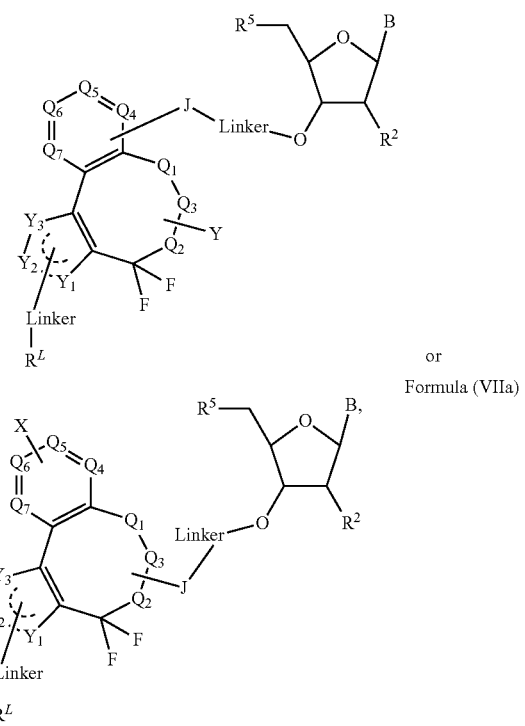

or
Formula (VIIa)

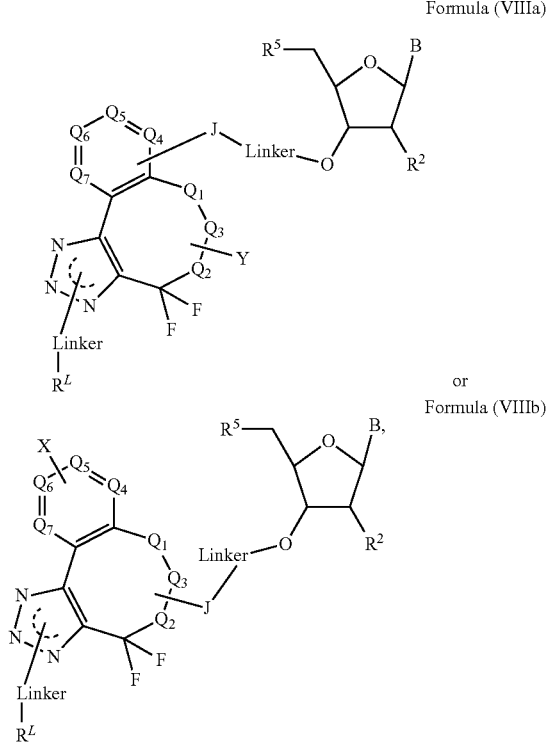

wherein B, $R^2$, $R^5$, $R^L$, J, $Q_1$, $Q_2$, $Q_3$, $Q_4$, $Q_5$, $Q_6$, $Q_7$, X, Y, $Y_1$, $Y_2$, and $Y_3$ are as defined in the first embodiment.

In one embodiment, the invention features, a compound having the structure shown in formula (VIIIa) or (VIIIb):

Formula (VIIIa)

or
Formula (VIIIb)

wherein B, $R^2$, $R^5$, $R^L$, J, $Q_1$, $Q_2$, $Q_3$, $Q_4$, $Q_5$, $Q_6$, $Q_7$, X, and Y are as defined in the first embodiment.

In one embodiment, the invention features, a compound having the structure shown in formula (IX):

Formula (IXa)

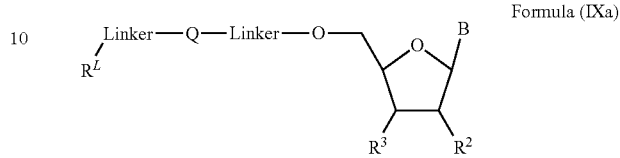

wherein B, $R^2$, $R^3$, $R^L$, J, $Q_1$, $Q_2$, $Q_3$, $Q_4$, $Q_5$, $Q_6$, $Q_7$, X, Y, $Y_1$, $Y_2$, and $Y_3$ are as defined in the first embodiment. In one embodiment, the invention features, a compound having the structure shown in formula (IXa) or (IXb):

Formula (IXa)

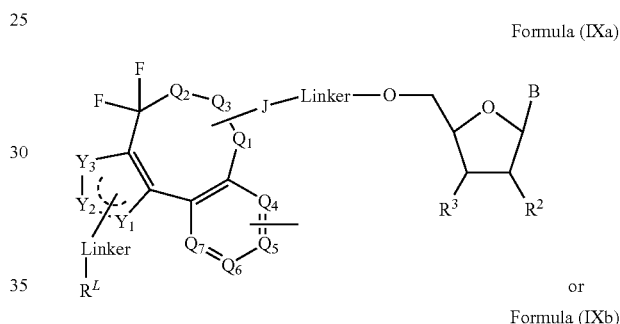

or
Formula (IXb)

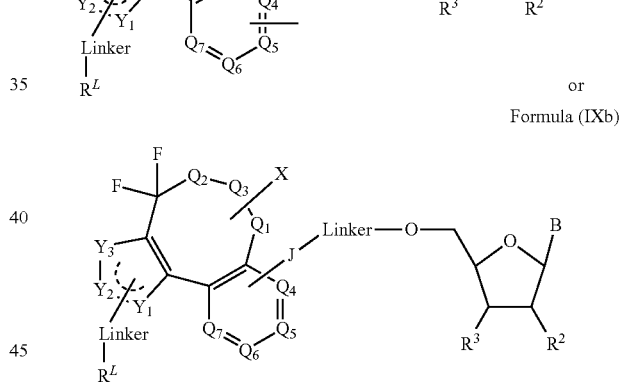

wherein B, $R^2$, $R^3$, $R^L$, J, $Q_1$, $Q_2$, $Q_3$, $Q_4$, $Q_5$, $Q_6$, $Q_7$, X, Y, $Y_1$, $Y_2$, and $Y_3$ are as defined in the first embodiment.

In one embodiment, the invention features, a compound having the structure shown in formula (Xa) or (Xb):

Formula (Xa)

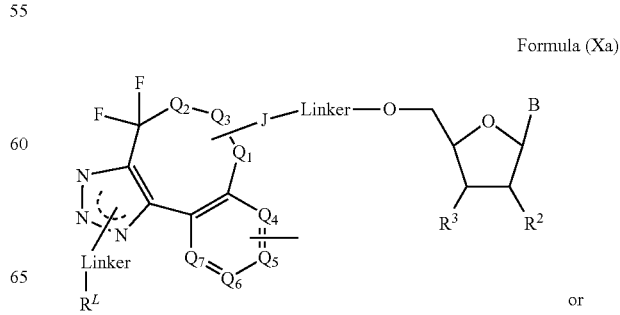

or

-continued

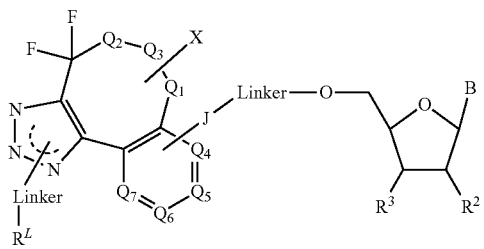

Formula (Xb)

wherein B, R², R³, R$^L$, J, Q$_1$, Q$_2$, Q$_3$, Q$_4$, Q$_5$, Q$_6$, Q$_7$, X and Y are as defined in the first embodiment.

In one embodiment, the carrier may be based on the pyrroline ring system as shown in formula (XI):

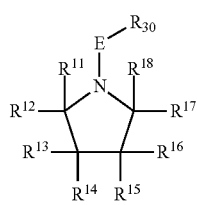

Formula (XI)

wherein E is absent or C(O), C(O)O, C(O)NH, C(S), C(S)NH, SO, SO$_2$, or SO$_2$NH;

R$^{11}$, R$^{12}$, R$^{13}$, R$^{14}$, R$^{15}$, R$^{16}$, R$^{17}$, and R$^{18}$ are each independently for each occurrence H, —CH$_2$OR$^a$, or OR$^b$, R$^a$ and R$^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P(Z$^1$)(Z$^2$)—O-nucleoside, —P(Z$^4$)(Z$^5$)—O-oligonucleotide, —P(Z$^4$)(Z$^5$)-formula (I), —P(Z$^4$)(O-linker-Q-linker-R$^L$)—O-nucleoside, —P(Z$^4$)(O-linker-N$_3$)—O-nucleoside, P(Z$^4$)(O-linker-CN)—O-nucleoside, P(Z$^4$)(O-linker-R$^8$)—O-nucleoside, P(Z$^4$)(O-linker-cycloalkyne)-O-nucleoside, —P(Z$^4$)(O-linker-R$^L$)—O-oligonucleotide, —P(Z$^4$)(O-linker-Q-linker-R$^L$)—O-oligonucleotide, —P(Z$^4$)(O-linker-R$^L$)—O-oligonucleotide, P(Z$^4$)(O-linker-N$_3$)—O-oligonucleotide, —P(Z$^4$)(O-linker-CN)—O-oligonucleotide, P(Z$^4$)(O-linker-R$^8$)—O-oligonucleotide, P(Z$^4$)(O-linker-cycloalkyne)-O-oligonucleotide, —P(Z$^4$)(-linker-Q-linker-R$^L$)—O-nucleoside, P(Z$^4$)(-linker-R$^L$)—O-nucleoside, —P(Z$^4$)(-linker-N$_3$)—O-nucleoside, P(Z$^4$)(-linker-CN)—O-nucleoside, P(Z$^4$)(-linker-R$^8$)—O-nucleoside, P(Z$^4$)(-linker-cycloalkyne)-O-nucleoside, —P(Z$^4$)(-linker-Q-linker-R$^L$)—O-oligonucleotide, (Z$^4$)(-linker-R$^L$)—O-oligonucleotide, P(Z$^4$)(-linker-N$_3$)—O-oligonucleotide, —P(Z$^4$)(-linker-CN)—O-oligonucleotide, P(Z$^1$)(-linker-R$^8$)—O-oligonucleotide or P(Z$^4$)(-linker-cycloalkyne)-O-oligonucleotide;

R$^{30}$ is independently for each occurrence -linker-Q-linker-R$^L$, -linker-R$^L$ or R$^{31}$;

R$^{31}$ is —C(O)CH(N(R$^{32}$)$_2$)(CH$_2$)$_n$N(R$^{32}$)$_2$;

R$^{32}$ is independently for each occurrence H, -linker-Q-linker-R$^L$, -linker-R$^L$ or R$^{31}$;

R$^L$ is hydrogen or a ligand;

R$^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

R$^P$ is independently for each occurrence H, optionally substituted alkyl, optionally substituted alkenyl, optionally substituted alkynyl, optionally substituted aryl, optionally substituted cycloalkyl or optionally substituted heteroaryl;

R$^8$ is

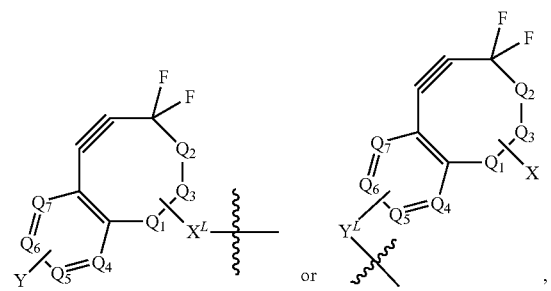

X$^L$ and Y$^L$ are independently absent, —(CH$_2$)$_n$O—, —(CH$_2$)$_n$COO—, —(CH$_2$)$_n$N(R$^9$)—, —(CH$_2$)$_n$S—, (CH$_2$)$_n$S—S—, —(CH$_2$)$_n$O—N(R$^9$)—, or —(CH$_2$)$_n$CO—;

X and Y are independently H, a bond, (CH$_2$)$_n$OH, (CH$_2$)$_n$COOH, (CH$_2$)$_n$N(R$^9$)(R$^9$), (CH$_2$)$_n$SH, (CH$_2$)$_n$S—SP-Py, (CH$_2$)$_n$O—N(R$^9$)(R$^9$), (CH$_2$)$_n$CHO, or (CH$_2$)$_n$COR$^{10}$;

Q$^1$, Q$^2$ and Q$^3$ are independently C(R$^P$)$_2$, NR$^9$, O, or S;

Q$^4$, Q$^5$, Q$^6$ and Q$^7$ are independently CR$^P$ or N;

Q is independently for each occurrence

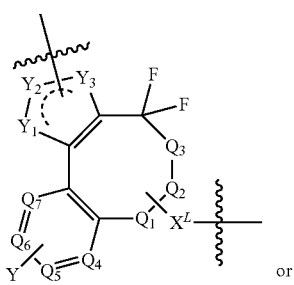

or

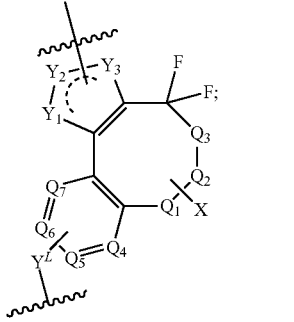

Y$_1$, Y$_2$ and Y$_3$ are independently CR$^P$, N, O, or S;

Z$^4$ and Z$^5$ are each independently for each occurrence O, S or optionally substituted alkyl;

$R^9$, and $R^{10}$ are independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

f and h are independently for each occurrence 1-20;

n is 0-20; and provided that at least one $R^8$ or Q is present.

For the pyrroline-based click-carriers, $R^{11}$ is —$CH_2OR^a$ and $R^{13}$ is $OR^b$; or $R^{11}$ is —$CH_2OR^a$ and $R^{15}$ is $OR^b$; or $R^{11}$ is —$CH_2OR^a$ and $R^{17}$ is $OR^b$; or $R^{13}$ is —$CH_2OR^a$ and $R^{11}$ is $OR^b$; or $R^{13}$ is —$CH_2OR^a$ and $R^{15}$ is $OR^b$; or $R^{13}$ is —$CH_2OR^a$ and $R^{17}$ is $OR^b$. In certain embodiments, $CH_2OR^a$ and $OR^b$ may be geminally substituted. For the 4-hydroxyproline-based carriers, $R^{11}$ is —$CH_2OR^a$ and $R^{17}$ is $OR^b$. The pyrroline- and 4-hydroxyproline-based compounds may therefore contain linkages (e.g., carbon-carbon bonds) wherein bond rotation is restricted about that particular linkage, e.g. restriction resulting from the presence of a ring. Thus, $CH_2OR^a$ and $OR^b$ may be cis or trans with respect to one another in any of the pairings delineated above Accordingly, all cis/trans isomers are expressly included. The compounds may also contain one or more asymmetric centers and thus occur as racemates and racemic mixtures, single enantiomers, individual diastereomers and diastereomeric mixtures. All such isomeric forms of the compounds are expressly included (e.g., the centers bearing $CH_2OR^a$ and $OR^b$ can both have the R configuration; or both have the S configuration; or one center can have the R configuration and the other center can have the S configuration and vice versa).

In one embodiment, $R^{11}$ is $CH_2OR^a$ and $R^{17}$ is $OR^b$.

In one embodiment, $R^b$ is a solid support.

In one preferred embodiment, $R^{31}$ is —$C(O)CH(N(R^{32})_2)(CH_2)_4N(R^{32})_2$ and at least one $R^{32}$ is —$C(O)(CH_2)_fCR^8$ or -linker-Q-linker-$R^L$ and $R^L$ is present.

In one preferred embodiment, $R^{31}$ is —$C(O)CH(N(R^{32})_2)(CH_2)_4NH_2$ and at least one $R^{32}$ is —$C(O)(CH_2)_fCR^8$ or -linker-Q-linker-$R^L$ and $R^L$ is present.

In one embodiment, the invention features, a compound having the structure shown in formula (XII):

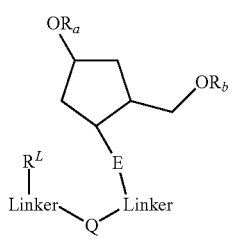

Formula (XII)

wherein $R_a$ and $R_b$ are independently hydrogen, an activated phosphate group, an activated phosphite group, a phosphoramidite, a solid support, —$P(Z^4)(Z^5)$—OH, —$P(Z^5)(Z^5)$—O-nucleoside, —$P(Z^5)(Z^5)$—O-oligonucleotide; each linker can be the same or different; and E, $R^L$, and Q are as defined in the previous embodiments.

In one embodiment, the invention features, a compound having the structure shown in formula (XIIa) or (XIIb):

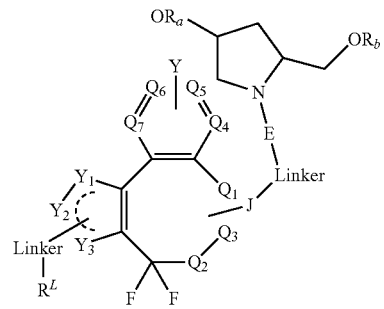

Formula (XIIa)

or

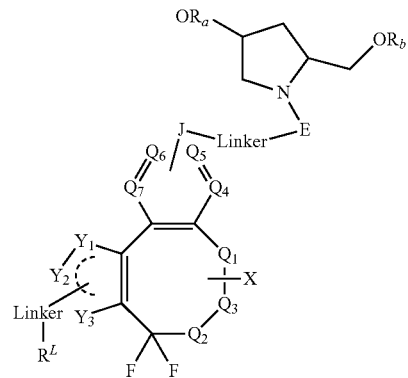

Formula (XIIb)

wherein $R_a$ and $R_b$ are independently hydrogen, an activated phosphate group, an activated phosphite group, a phosphoramidite, a solid support, —$P(Z^4)(Z^5)$—OH, —$P(Z^5)(Z^5)$—O-nucleoside, —$P(Z^5)(Z^5)$—O-oligonucleotide; each linker can be the same or different; and E, $R^L$, J, $Q_1$, $Q_2$, $Q_3$, $Q_4$, $Q_5$, $Q_6$, $Q_7$, X, Y, $Y_1$, $Y_2$, and $Y_3$ are as defined in the previous embodiments.

In one embodiment, the invention features, a compound having the structure shown in formula (XIIIa) or (XIIIb):

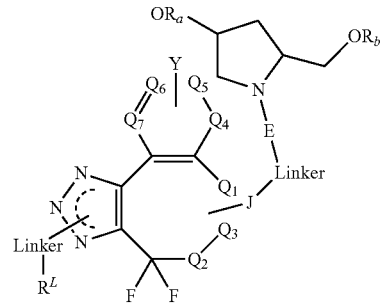

Formula (XIIIa)

or

-continued

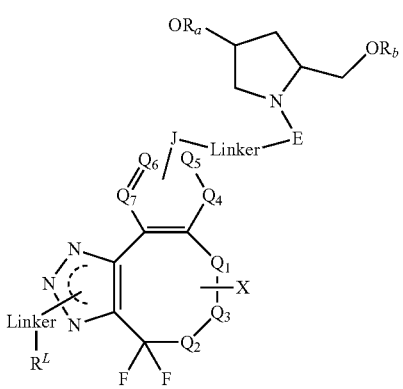

Formula (XIIIb)

wherein $R_a$ and $R_b$ are independently hydrogen, an activated phosphate group, an activated phosphite group, a phosphoramidite, a solid support, —P($Z^4$)($Z^5$)—OH, —P($Z^5$)($Z^5$)—O-nucleoside, —P($Z^5$)($Z^5$)—O-oligonucleotide; each linker can be the same or different; and E, $R^L$, J, $Q_1$, $Q_2$, $Q_3$, $Q_4$, $Q_5$, $Q_6$, $Q_7$, X, and Y are as defined in the previous embodiments.

In one embodiment features acyclic sugar replacement-based compounds, e.g., sugar replacement based click-carrier compounds, are also referred to herein as ribose replacement compound subunit (RRMS) compound compounds. Preferred acyclic carriers can have the structure shown in formula (XIV) below.

In one aspect, the invention features, an acyclic click-carrier compound having the structure shown in formula (XIV)

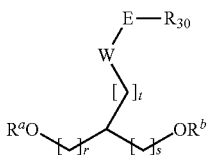

Formula (XIV)

wherein:

W is absent, O, S and N($R^N$), where $R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

E is absent or C(O), C(O)O, C(O)NH, C(S), C(S)NH, SO, $SO_2$, or $SO_2NH$;

$R^a$ and $R^b$ are each independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^5$)($Z^5$)—O-nucleoside, —P($Z^4$)($Z^5$)—O-oligonucleotide, —P($Z^5$)($Z^5$)-formula (I), —P($Z^5$)(O-linker-Q-linker-$R^L$)—O-nucleoside, —P($Z^5$)(O-linker-$N_3$)—O-nucleoside, P($Z^4$)(O-linker-CN)—O-nucleoside, P($Z^4$)(O-linker-$R^8$)—O-nucleoside, P($Z^4$)(O-linker-cycloalkyne)-O-nucleoside, —P($Z^4$)(O-linker-$R^L$)—O-oligonucleotide, —P($Z^4$)(O-linker-Q-linker-$R^L$)—O-oligonucleotide, —P($Z^4$)(O-linker-$R^L$)—O-oligonucleotide, P($Z^4$)(O-linker-$N_3$)—O-oligonucleotide, —P($Z^4$)(O-linker-CN)—O-oligonucleotide, P($Z^1$)(O-linker-$R^8$)—O-oligonucleotide, P($Z^4$)(O-linker-cycloalkyne)-O-oligonucleotide, —P($Z^4$)(-linker-Q-linker-$R^L$)—O-nucleoside, P($Z^4$)(-linker-$R^L$)—O-nucleoside, —P($Z^4$)(-linker-$N_3$)—O-nucleoside, P($Z^4$)(-linker-CN)—O-nucleoside, P($Z^4$)(-linker-$R^8$)—O-nucleoside, P($Z^4$)(-linker-cycloalkyne)-O-nucleoside, —P($Z^4$)(-linker-Q-linker-$R^L$)—O-oligonucleotide, ($Z^4$)(-linker-$R^L$)—O-oligonucleotide, P($Z^4$)(-linker-$N_3$)—O-oligonucleotide, —P($Z^4$)(-linker-CN)—O-oligonucleotide, P($Z^4$)(-linker-$R^8$)—O-oligonucleotide or P($Z^4$)(-linker-cycloalkyne)-O-oligonucleotide;

$R^{30}$ is independently for each occurrence -linker-Q-linker-$R^L$, -linker-$R^L$ or $R^{31}$;

$R^{31}$ is —C(O)CH(N($R^{32}$)$_2$)($CH_2$)$_n$N($R^{32}$)$_2$;

$R^{32}$ is independently for each occurrence H, -linker-Q-linker-$R^L$, -linker-$R^L$ or $R^{31}$;

$R^L$ is hydrogen or a ligand;

$R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

$R^P$ is independently for each occurrence H, optionally substituted alkyl, optionally substituted alkenyl, optionally substituted alkynyl, optionally substituted aryl, optionally substituted cycloalkyl or optionally substituted heteroaryl;

$R^8$ is

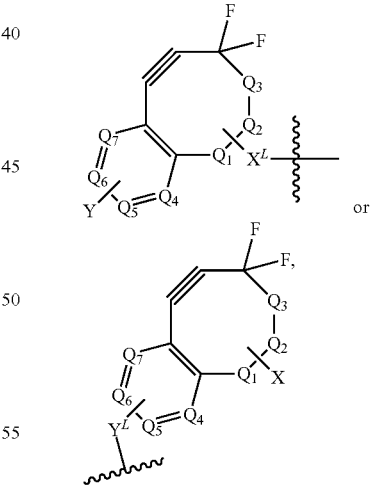

$X^L$ and $Y^L$ are independently absent, —($CH_2$)$_n$O—, —($CH_2$)$_n$COO—, —($CH_2$)$_n$N($R^9$)—, —($CH_2$)$_n$S—, ($CH_2$)$_n$S—S—, —($CH_2$)$_n$O—N($R^9$)—, or —($CH_2$)$_n$CO—;

X and Y are independently H, a bond, ($CH_2$)$_n$OH, ($CH_2$)$_n$COOH, ($CH_2$)$_n$N($R^9$)($R^9$), ($CH_2$)$_n$SH, ($CH_2$)$_n$S—SP-Py, ($CH_2$)$_n$O—N($R^9$)($R^9$), ($CH_2$)$_n$CHO, or ($CH_2$)$_n$COR$^{10}$;

$Q^1$, $Q^2$ and $Q^3$ are independently C($R^P$)$_2$, N$R^9$, O, or S;

$Q^4$, $Q^5$, $Q^6$ and $Q^7$ are independently C$R^P$ or N;

Q is independently for each occurrence

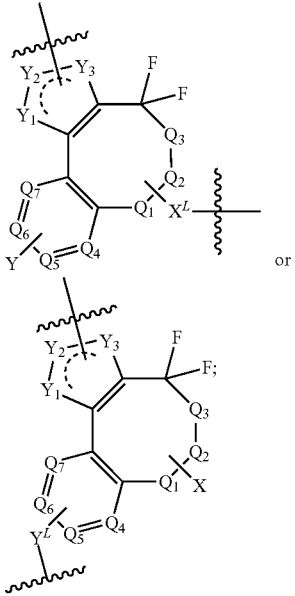

or

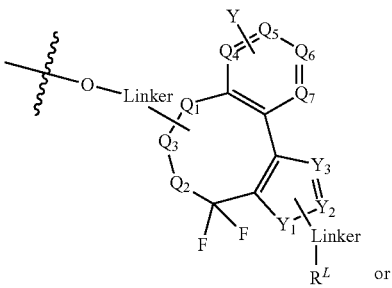

$Y_1$, $Y_2$ and $Y_3$ are independently $CR^P$, N, O, or S;

$Z^4$ and $Z^5$ are each independently for each occurrence O, S or optionally substituted alkyl;

$R^9$, and $R^{10}$ are independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

f and h are independently for each occurrence 1-20;

n is 0-20; and provided that at least one $R^8$ or Q is present

When r and s are different, then the tertiary carbon can be either the R or S configuration. In preferred embodiments, x and y are one and z is zero (e.g. carrier is based on serinol). The acyclic carriers can optionally be substituted, e.g. with hydroxy, alkoxy, perhaloalky.

Other carrier compounds amenable to the invention are described in copending applications U.S. Ser. No. 10/916,185, filed Aug. 10, 2004; U.S. Ser. No. 10/946,873, filed Sep. 21, 2004; U.S. Ser. No. 10/985,426, filed Nov. 9, 2004; U.S. Ser. No. 10/833,934, filed Aug. 3, 2007; U.S. Ser. No. 11/115,989 filed Apr. 27, 2005 and U.S. Ser. No. 11/119,533, filed Apr. 29, 2005, which are incorporated by reference in their entireties for all purposes.

In one embodiment, at least one $R^1$, $R^2$, $R^3$, $R^4$, or $R^5$ of formula (I) is

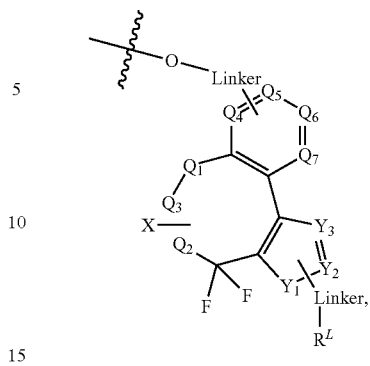

or

-continued

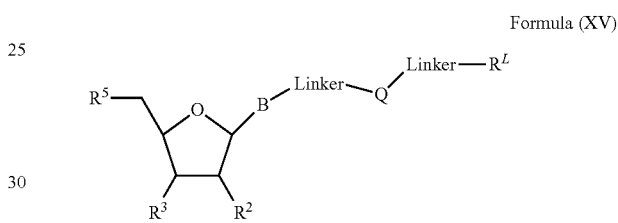

wherein $R^L$, $Q_1$, $Q_2$, $Q_3$, $Q_4$, $Q_5$, $Q_6$, $Q_7$, X, and Y are as previously defined.

In one embodiment, the invention features, a compound having the structure shown in formula (XV):

Formula (XV)

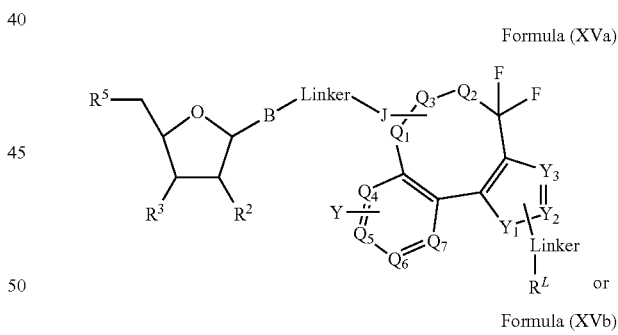

wherein each linker can be the same or different, and B, $R^2$, $R^3$, $R^5$, $R^L$, and Q are as defined in the first embodiment.

In one embodiment, the invention features, a compound having the structure shown in formula (XVa) or (XVb):

Formula (XVa)

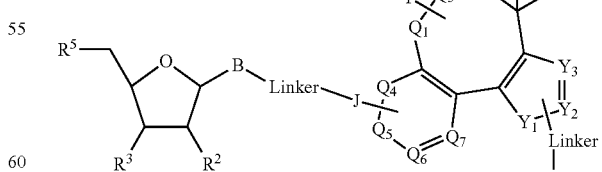

or

Formula (XVb)

wherein B, $R^2$, $R^3$, $R^5$, $R^L$, J, $Q_1$, $Q_2$, $Q_3$, $Q_4$, $Q_5$, $Q_6$, $Q_7$, X, Y, $Y_1$, $Y_2$, and $Y_3$ are as defined in the first embodiment.

In one embodiment, the invention features, a compound having the structure shown in formula (XVIa) or (XVIb):

Formula (XVIa)

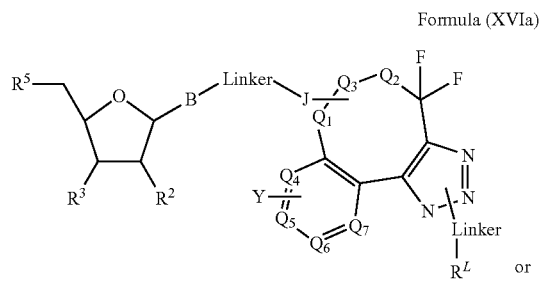

or

Formula (XVIb)

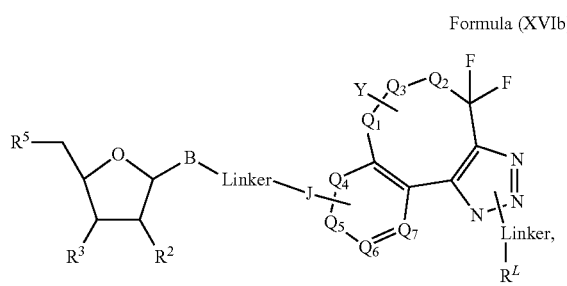

wherein B, $R^2$, $R^3$, $R^5$, $R^L$, J, $Q_1$, $Q_2$, $Q_3$, $Q_4$, $Q_5$, $Q_6$, $Q_7$, X, and Y are as defined in the first embodiment.

In one embodiment, the invention features, a compound having the structure shown in formula (XVIIa) or (XVIIb):

Formula (XVIIa)

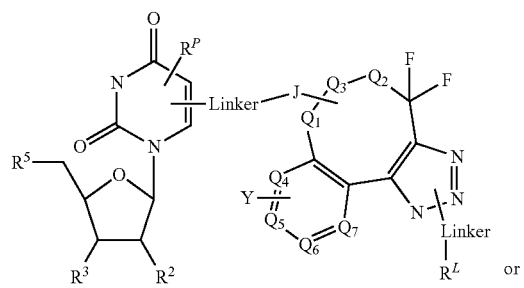

or

Formula (XVIIa)

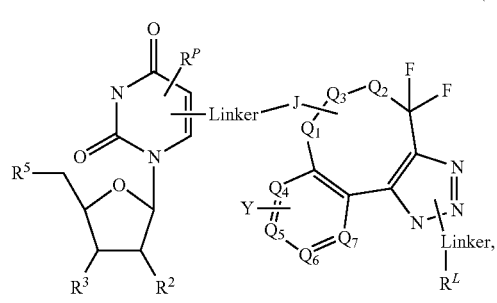

wherein $R^2$, $R^3$, $R^5$, $R^L$, $R^P$, J, $Q_1$, $Q_2$, $Q_3$, $Q_4$, $Q_5$, $Q_6$, $Q_7$, X, and Y are as defined in the first embodiment.

In one embodiment, the invention features a compound of formula (XVIII):

Formula (XVIII)

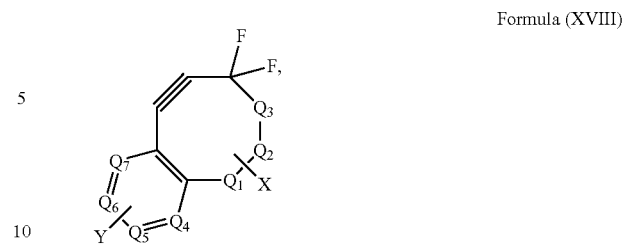

wherein $Q_1$, $Q_2$, $Q_2$, $Q_3$, $Q_4$, $Q_5$, $Q_6$, $Q_7$, X and Y are as defined in the first embodiment, provided that when X is H then Y is not H, and when Y is H then X is not H.

In the compounds of formula (XVIII), X and/or Y can be used for conjugation to nucleic acid (DNA, RNA, nucleic acid therapeutics such as siRNA and antisense oligonucleotides), any ligand of interest, any drug carrier or drug delivery vehicle.

Figure 11:
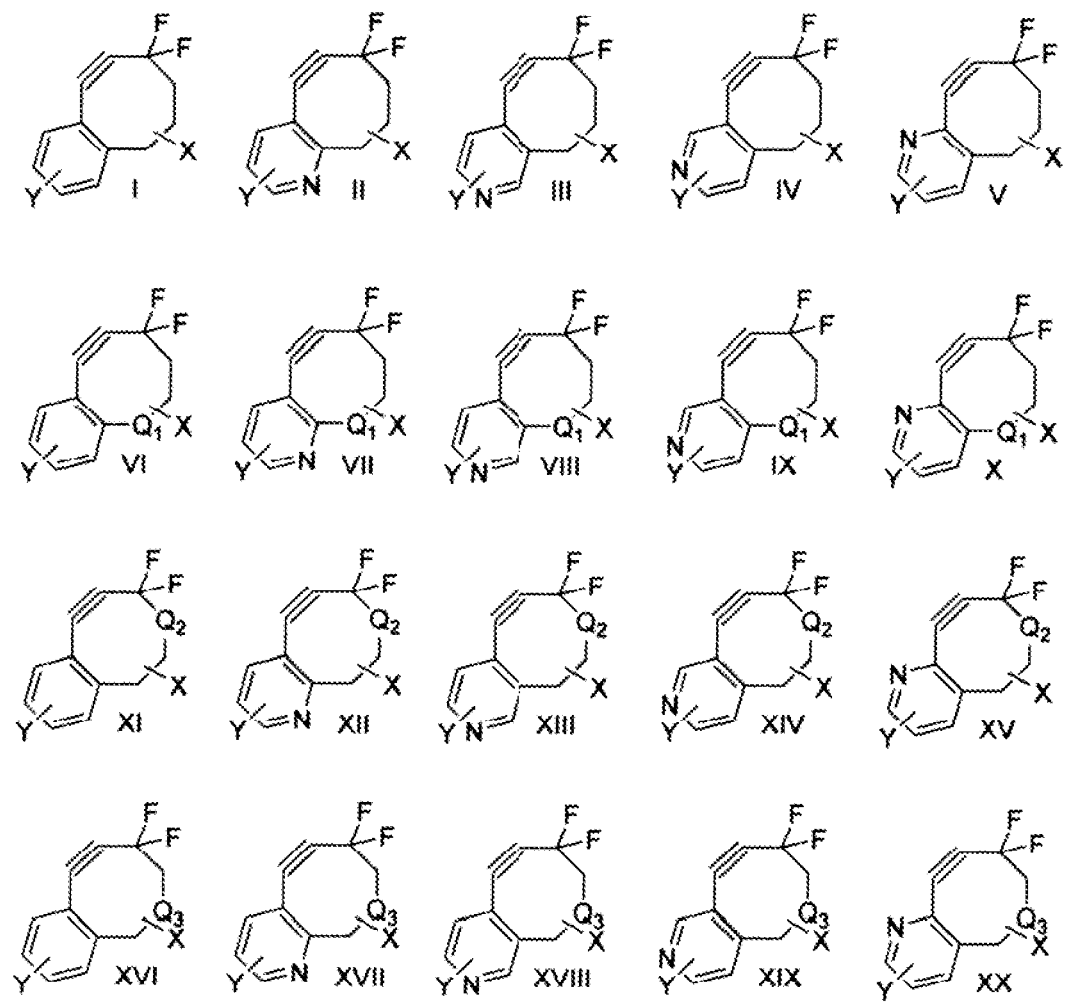
FIG. 11 depicts some of the exemplary strained/activated alkynes.

In some embodiments, a compound of formula (XVIII) is as shown in FIG. 11.

In one embodiment, the invention features a compound having the structure shown in formula (XIX)

XIX

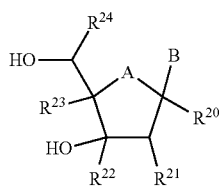

wherein:

A is O, S, $NR^N$ or $CR^P_2$;

B is independently for each occurrence hydrogen, optionally substituted natural or non-natural nucleobase, optionally substituted triazole, optionally substituted tetrazole, $R^6$, NH—C(O)—O—C(CH$_2$B$_1$)$_3$, NH—C(O)—NH—C(CH$_2$B$_1$)$_3$, where B$_1$ is halogen, mesylate, optionally substituted triazole, optionally substituted tetrazole, or $R^6$;

$R^{20}$, $R^{21}$, $R^{22}$, and $R^{23}$ are each independently for each occurrence H, $OR^7$, F, $N(R^N)_2$, $N_3$, CN, -J-linker-$N_3$, -J-linker-CN, -J-linker-$R^8$, -J-linker-cycloalkyne, -J-linker-$R_L$, -J-Q-linker-$R^L$ or -J-linker-Q-linker-$R^L$;

$R^{24}$ is independently for each occurrence H, halogen, optionally substituted alkyl, optionally substituted alkenyl, or optionally substituted alkynyl, J is absent, O, S, $NR^N$, OC(O)NH, NHC(O)O, C(O)NH, NHC(O), NHSO, NHSO$_2$, NHSO$_2$NH, OC(O), C(O)O, OC(O)O, NHC(O)NH, NHC(S)NH, OC(S)NH, O—N=CH, OP(N($R^N$)$_2$)O, or OP(N($R^N$)$_2$);

$R^6$ is

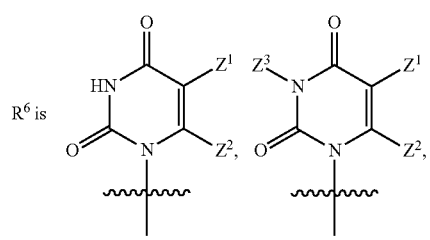

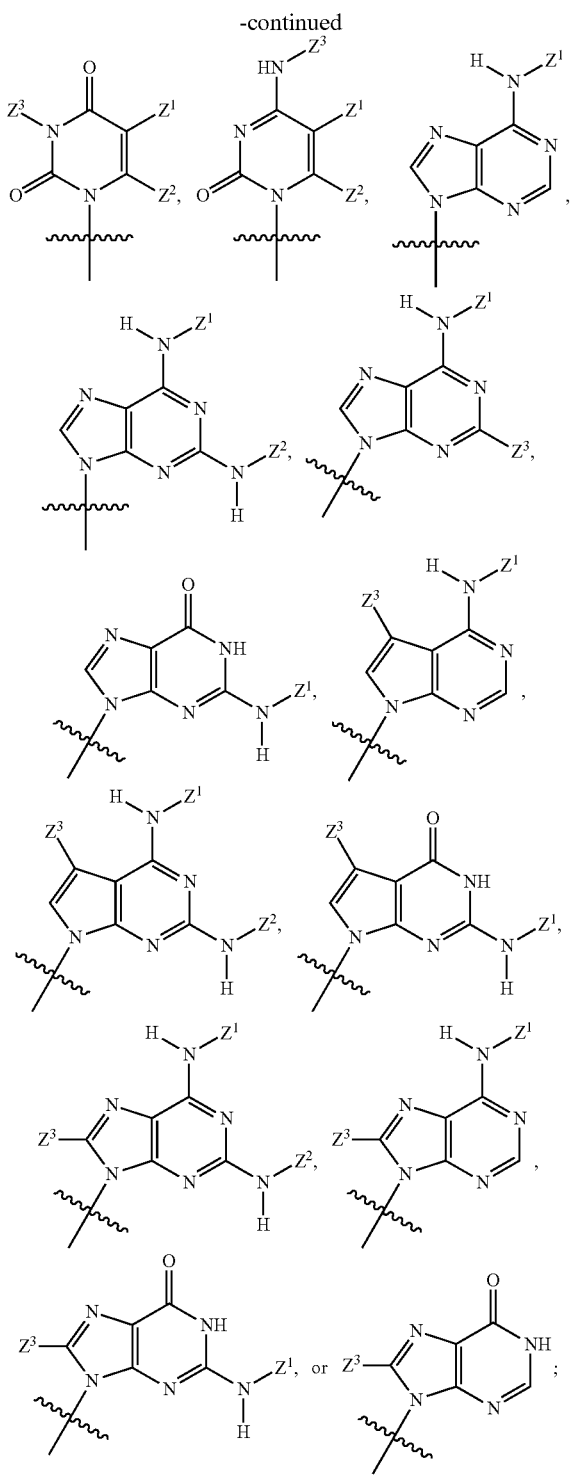

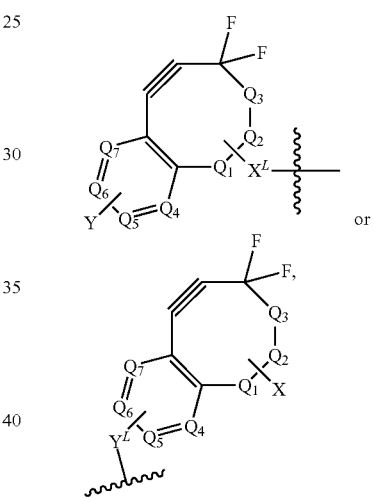

R[7] is independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^1$)($Z^2$)—O-nucleoside, —P($Z^4$)($Z^5$)—O-oligonucleotide, —P($Z^4$)($Z^5$)-formula (I), —P($Z^4$)(O-linker-Q-linker-$R^L$)—O-nucleoside, —P($Z^4$)(O-linker-$N_3$)—O-nucleoside, P($Z^4$)(O-linker-CN)—O-nucleoside, P($Z^4$)(O-linker-$R^8$)—O-nucleoside, P($Z^4$)(O-linker-cycloalkyne)-O-nucleoside, —P($Z^4$)(O-linker-$R^L$)—O-oligonucleotide, —P($Z^4$)(O-linker-Q-linker-$R^L$)—O-oligonucleotide, —P($Z^4$)(O-linker-$R^L$)—O-oligonucleotide, P($Z^4$)(O-linker-$N_3$)—O-oligonucleotide, —P($Z^4$)(O-linker-CN)—O-oligonucleotide, P($Z^4$)(O-linker-$R^8$)—O-oligonucleotide, P($Z^4$)(O-linker-cycloalkyne)-O-oligonucleotide, —P($Z^4$)(-linker-Q-linker-$R^L$)—O-nucleoside, P($Z^4$)(-linker-$R^L$)—O-nucleoside, —P($Z^4$)(-linker-$N_3$)—O-nucleoside, P($Z^4$)(-linker-CN)—O-nucleoside, P($Z^4$)(-linker-$R^8$)—O-nucleoside, P($Z^4$)(-linker-cycloalkyne)-O-nucleoside, —P($Z^4$)(-linker-Q-linker-$R^L$)—O-oligonucleotide, ($Z^4$)(-linker-$R^L$)—O-oligonucleotide, P($Z^4$)(-linker-$N_3$)—O-oligonucleotide, —P($Z^4$)(-linker-CN)—O-oligonucleotide, P($Z^1$)(-linker-$R^8$)—O-oligonucleotide or P($Z^4$)(-linker-cycloalkyne)-O-oligonucleotide;

R[8] is $X^L$ and $Y^L$ are independently absent, a linker, —$(CH_2)_n$O—, —$(CH_2)_n$COO—, —$(CH_2)_n$N($R^9$)—, —$(CH_2)_n$S—, ($CH_2)_n$S—S—, —$(CH_2)_n$O—N($R^9$)—, or —$(CH_2)_n$CO—;

X and Y are independently H, a bond, $(CH_2)_n$OH, $(CH_2)_n$COOH, $(CH_2)_n$N($R^9$)($R^9$), $(CH_2)_n$SH, $(CH_2)_n$S—SP-Py, $(CH_2)_n$O—N($R^9$)($R^9$), $(CH_2)_n$CHO, or $(CH_2)_n$COR[10];

$Q^1$, $Q^2$ and $Q^3$ are independently C($R^P$)$_2$, N$R^9$, O, or S;

$Q^4$, $Q^5$, $Q^6$ and $Q^7$ are independently C$R^P$ or N;

$R^9$, $R^{10}$ and $R^N$ are independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

$R^L$ is hydrogen or a ligand;

$R^P$ is independently for each occurrence H, optionally substituted alkyl, optionally substituted alkenyl, optionally substituted alkynyl, optionally substituted aryl, optionally substituted cycloalkyl, optionally substituted aralkyl or optionally substituted heteroaryl;

Q is independently for each occurrence

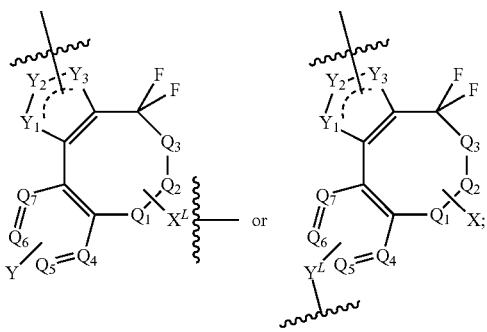

$Y_1$, $Y_2$ and $Y_3$ are independently $CR^P$, N, O, or S;

each of $Z^1$, $Z^2$ and $Z^3$ independently comprises a $R^8$ or an azide;

$Z^4$ and $Z^5$ are each independently for each occurrence O, S or optionally substituted alkyl;

n is 0-20; and provided that at least one $R^8$ or azide is present, and when $R^8$ is present then an azide is not present in the same compound and when an azide is present then $R^8$ is not present in the same compound.

Figure 12:
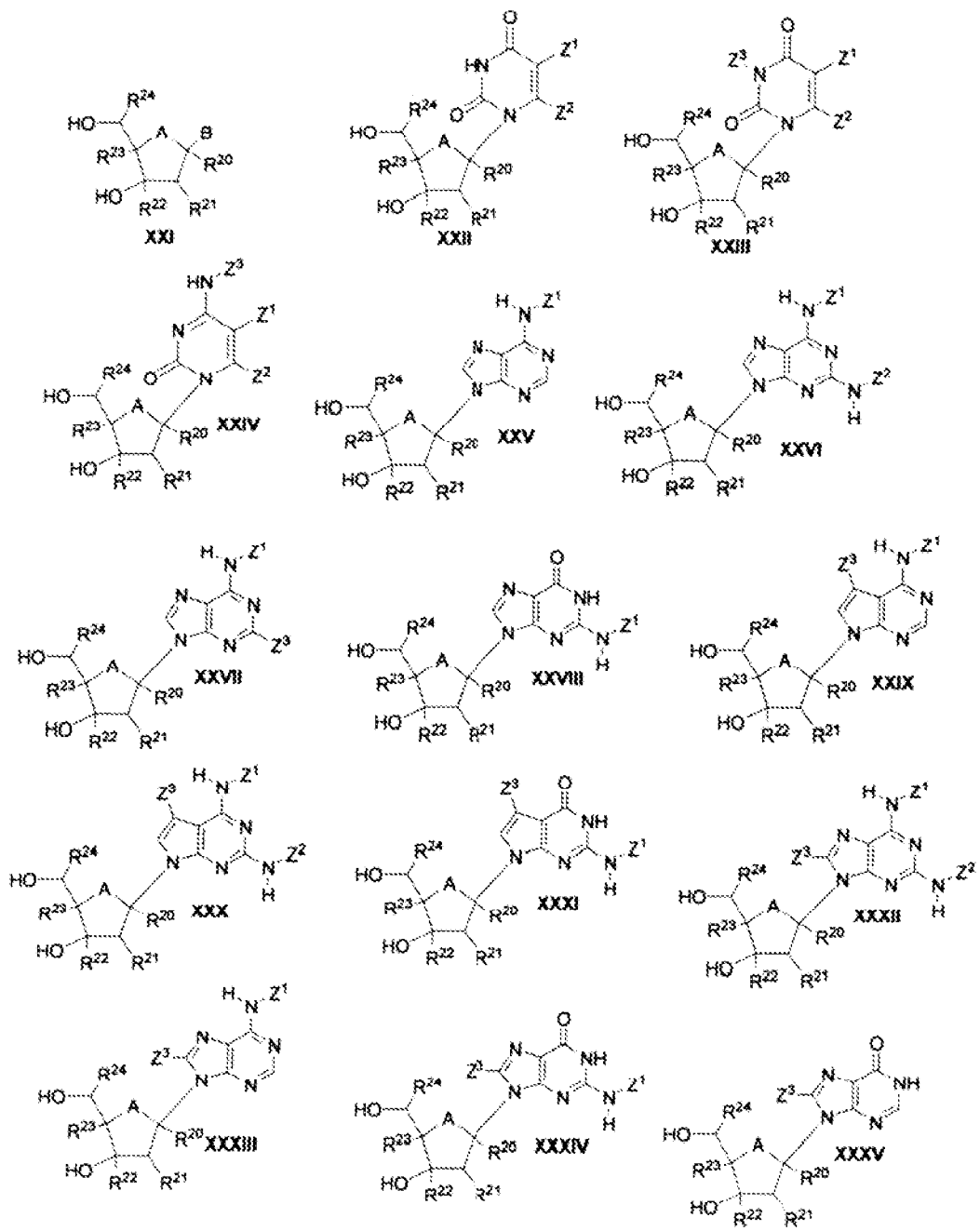
FIG. 12 depicts nucleosides functionalized with strained/activated alkynes for incorporation into nucleic acids. Each of $Z^1$, $Z^2$, and $Z^3$ comprises either an strained/activated alkyne (e.g. $R^8$) or an azide, provided that when an alkyne is present the azide is not present in the same nucleoside and when an azide is present the alkyne is not present in the same nucleoside. The activated alkyne moiety reacts with azido functionalized ligand or molecules of interest to obtain the desired conjugate.

In some embodiments, compounds of formula (XIX) are as shown in FIG. 12.

In one embodiment, $R^L$ is selected from:

Linkers

The term "linker" means an organic moiety that connects two parts of a compound. Linkers typically comprise a direct bond or an atom such as oxygen or sulfur, a unit such as $NR^1$, S—S, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R^1)_2$, C(O), substituted or unsubstituted aryl, substituted or unsubstituted heteroaryl, substituted or unsubstituted het-

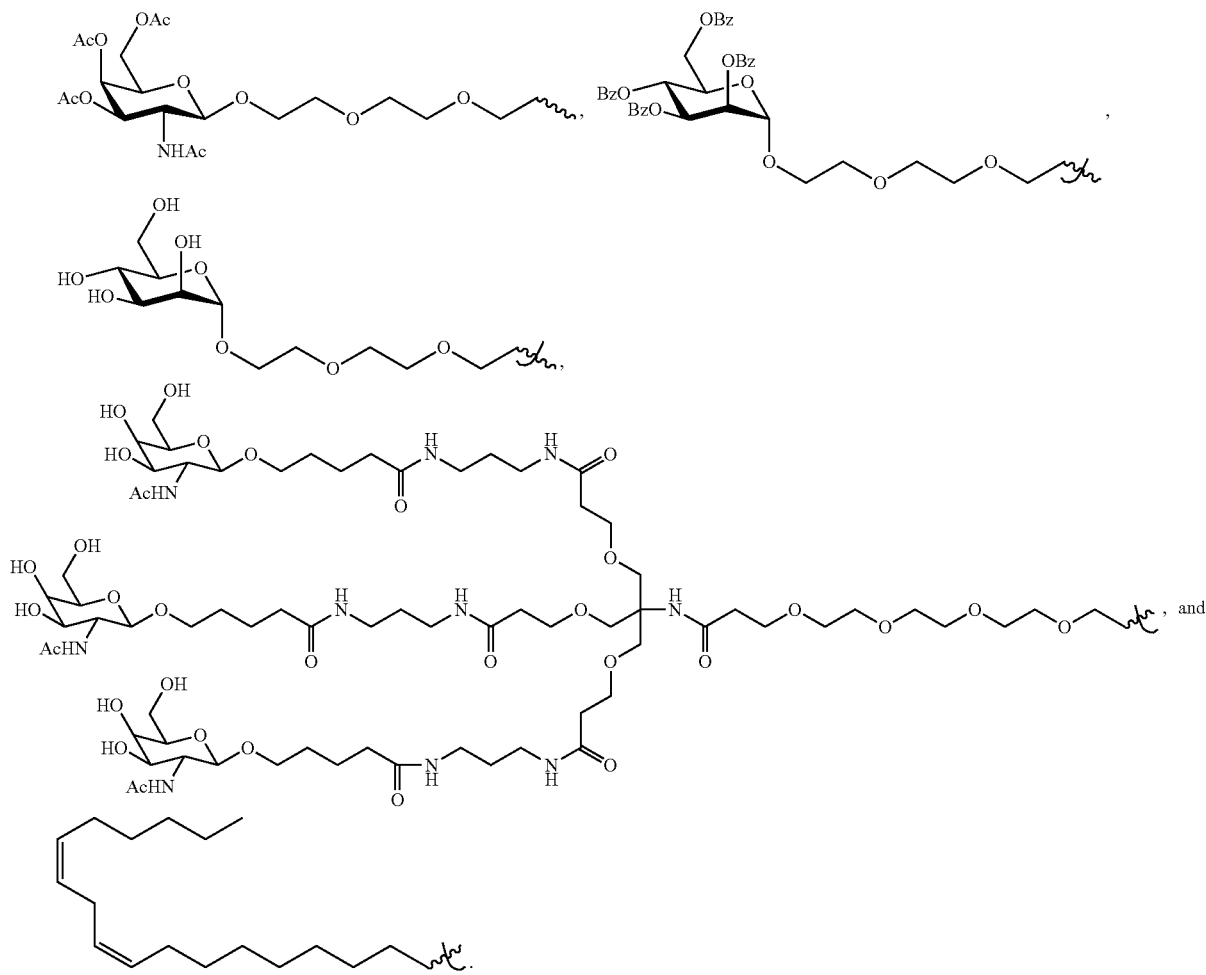

erocyclic; where $R^1$ is hydrogen, acyl, aliphatic or substituted aliphatic. It is further understood that linker can be non-cleavable or cleavable.

In one embodiment, the linker is C1-C30 alkyl, optionally interrupted with at least one O, S, $NR^N$, N(CO)O or combinations thereof.

In one embodiment, the linker is C1-C12 alkyl.

In one embodiment, the linker is represented by structure

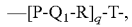

wherein:

P, R and T are each independently for each occurrence absent, CO, NH, O, S, S—S, OC(O), NHC(O), $CH_2$, $CH_2NH$, $CH_2O$; $NHCH(R^a)C(O)$, $-C(O)-CH(R^a)-NH-$, $-C(O)$-(optionally substituted alkyl)-NH—, CH=N—O,

acetal, ketal,

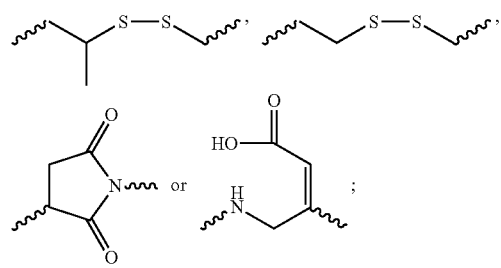

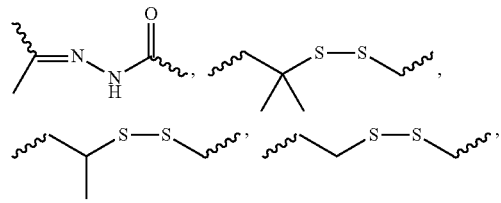

$Q_1$ is independently for each occurrence absent, $-(CH_2)_n-$, $-C(R^{100})(R^{200})(CH_2)_n-$, $-(CH_2)_nC(R^{100})(R^{200})-$, $-(CH_2CH_2O)_mCH_2CH_2-$, or $-(CH_2CH_2O)_mCH_2CH_2NH-$;

$R^a$ is H or an amino acid side chain;

$R^{100}$ and $R^{200}$ are each independently for each occurrence H, $CH_3$, OH, SH or $N(R^X)_2$;

$R^X$ is independently for each occurrence H, methyl, ethyl, propyl, isopropyl, butyl or benzyl;

q is independently for each occurrence 0-20;

n is independently for each occurrence 1-20; and m is independently for each occurrence 0-50.

In one embodiment, the linker has the structure $-[(P-Q_1-R)_q-X-(P'-Q_1'-R')_{q'}]_{q''}-T$, wherein:

P, R, T, P', R' and T' are each independently for each occurrence absent, CO, NH, O, S, OC(O), NHC(O), $CH_2$, $CH_2NH$, $CH_2O$; $NHCH(R^a)C(O)$, $-C(O)-CH(R^a)-NH-$, $-C(O)$-(optionally substituted alkyl)-NH—, acetal, ketal, CH=N—O,

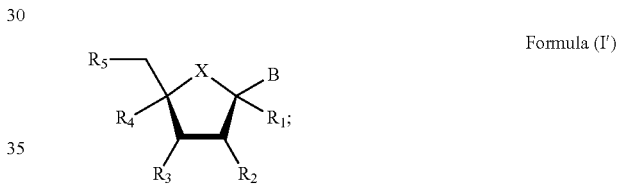

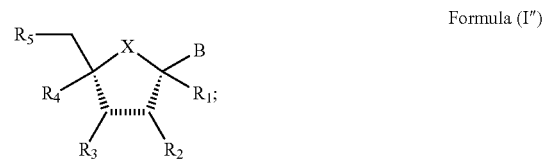

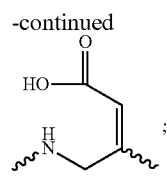

$Q_1$ and $Q_1'$ are each independently for each occurrence absent, $-(CH_2)_n-$, $-C(R^{100})(R^{200})(CH_2)_n-$, $-(CH_2)_nC(R^{100})(R^{200})-$, $-(CH_2CH_2O)_mCH_2CH_2-$, or $-(CH_2CH_2O)_mCH_2CH_2NH-$;

X is a cleavable linker;

$R^a$ is H or an amino acid side chain;

$R^{100}$ and $R^{200}$ are each independently for each occurrence H, $CH_3$, OH, SH or $N(R^X)_2$;

$R^X$ is independently for each occurrence H, methyl, ethyl, propyl, isopropyl, butyl or benzyl;

q, q' and q' are each independently for each occurrence 0-20;

n is independently for each occurrence 1-20; and m is independently for each occurrence 0-50.

In one embodiment, the linker comprises at least one cleavable linker.

In one embodiment, the ribose sugar of formula (I) has the structure shown in formula (I').

![Formula (I')](structure showing pentagonal ring with $R_5$, X, B, $R_4$, $R_1$, $R_3$, $R_2$ substituents)

wherein variable are as defined above for formula (I).

In one embodiment, the ribose sugar of formula (I) has the structure shown in formula (I'').

![Formula (I'')](structure showing pentagonal ring with $R_5$, X, B, $R_4$, $R_1$, $R_3$, $R_2$ substituents with stereochemistry)

wherein variable are as defined above for formula (I).

Cleavable Linker

A cleavable linker is one which is sufficiently stable outside the cell, but which upon entry into a target cell is cleaved to release the two parts the linker is holding together. In a preferred embodiment, the cleavable linker is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linkers are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linker by reduction; esterases; endosomes or agents that can create an acidic environment, e.g., those that result in a pH of five or lower; enzymes that can hydrolyze or degrade an acid cleavable linker by acting as a general acid, peptidases (which can be substrate specific), and phosphatases.

A cleavable linker, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some spacers will have a linker that is cleaved at a preferred pH, thereby releasing the iRNA agent from the carrier oligomer inside the cell, or into the desired compartment of the cell.

A spacer can include a linker that is cleavable by a particular enzyme. The type of linker incorporated into a spacer can depend on the cell to be targeted by the iRNA agent. For example, an iRNA agent that targets an mRNA in liver cells can be linked to the carrier oligomer through a spacer that includes an ester group. Liver cells are rich in esterases, and therefore the tether will be cleaved more efficiently in liver cells than in cell types that are not esterase-rich. Cleavage of the spacer releases the iRNA agent from the carrier oligomer, thereby potentially enhancing silencing activity of the iRNA agent. Other cell-types rich in esterases include cells of the lung, renal cortex, and testis.

Spacers that contain peptide bonds can be used when the iRNA agents are targeting cell types rich in peptidases, such as liver cells and synoviocytes. For example, an iRNA agent targeted to synoviocytes, such as for the treatment of an inflammatory disease (e.g., rheumatoid arthritis), can be linked to a carrier oligomer through spacer that comprises a peptide bond.

In general, the suitability of a candidate cleavable linker can be evaluated by testing the ability of a degradative agent (or condition) to cleave the candidate linker. It will also be desirable to also test the candidate cleavable linker for the ability to resist cleavage in the blood or when in contact with other non-target tissue, e.g., tissue the iRNA agent would be exposed to when administered to a subject. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linkers

One class of cleavable linkers are redox cleavable linkers that are cleaved upon reduction or oxidation. An example of reductively cleavable linker is a disulphide linker (—S—S—). To determine if a candidate cleavable linker is a suitable "reductively cleavable linker," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linkers

Phosphate-based linkers are cleaved by agents that degrade or hydrolyze the phosphate group. An example of an agent that cleaves phosphate groups in cells are enzymes such as phosphatases in cells. Examples of phosphate-based linkers are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linkers

Acid cleavable linkers are linkers that are cleaved under acidic conditions. In preferred embodiments acid cleavable linkers are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linkers. Examples of acid cleavable linkers include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linkers

Ester-based linkers are cleaved by enzymes such as esterases and amidases in cells. Examples of ester-based cleavable linkers include but are not limited to esters of alkylene, alkenylene and alkynylene groups. Ester cleavable linkers have the general formula —C(O)O—, or —OC(O)—. These candidates can be evaluated using methods analogous to those described above.

Peptide-Based Cleaving Groups

Peptide-based linkers are cleaved by enzymes such as peptidases and proteases in cells.

Peptide-based cleavable linkers are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide cleavable linkers have the general formula —NHCHR$^1$C(O) NHCHR$^2$C(O)—, where R$^1$ and R$^2$ are the R groups of the two adjacent amino acids. These candidates can be evaluated using methods analogous to those described above.

"Click" Reaction

The synthesis methods of the present invention utilize click chemistry to conjugate the ligand to the click-carrier compound. Click chemistry techniques are described, for example, in the following references, which are incorporated herein by reference in their entirety:

Kolb, H. C.; Finn, M. G. and Sharpless, K. B. *Angew. Chem., Int. Ed.* (2001) 40: 2004-2021.

Kolb, H. C. and Shrapless, K. B. *Drug Disc. Today* (2003) 8: 112-1137.

Rostovtsev, V. V.; Green L. G.; Fokin, V. V. and Shrapless, K. B. *Angew. Chem., Int. Ed.* (2002) 41: 2596-2599.

Tornøe, C. W.; Christensen, C. and Meldal, M. *J. Org. Chem.* (2002) 67: 3057-3064.

Wang, Q. et al., *J. Am. Chem. Soc.* (2003) 125: 3192-3193.

Lee, L. V. et al., *J. Am. Chem. Soc.* (2003) 125: 9588-9589.

Lewis, W. G. et al., *Angew. Chem., Int. Ed.* (2002) 41: 1053-1057.

Manetsch, R. et al., *J. Am. Chem. Soc.* (2004) 126: 12809-12818.

Mocharla, V. P. et al., *Angew. Chem., Int. Ed.* (2005) 44: 116-120.

Although other click chemistry functional groups can be utilized, such as those described in the above references, the use of cycloaddition reactions is preferred, particularly the reaction of azides with alkynyl groups. In the presence of Cu(I) salts, terminal alkynes and azides undergo 1,3-dipolar cycloaddition forming 1,4-disubstituted 1,2,3-triazoles. In the presence of Ru(II) salts (e.g. Cu*RuCl(PPh$_3$)$_2$), terminal alkynes and azides under go 1,3-dipolar cycloaddition forming 1,5-disubstituted 1,2,3-triazoles (Folkin, V. V. et al., *Org. Lett.* (2005) 127: 15998-15999). Alternatively, a 1,5-disubstituted 1,2,3-triazole can be formed using azide and alkynyl reagents (Kraniski, A.; Fokin, V. V. and Sharpless, K. B. *Org. Lett.* (2004) 6: 1237-1240. Hetero-Diels-Alder reactions or 1,3-dipolar cycloaddition reaction could also be used (see for example Padwa, A. 1,3-*Dipolar Cycloaddition Chemistry: Volume* 1, John Wiley, New York, (1984) 1-176; Jorgensen, K. A. *Angew. Chem., Int. Ed.* (2000) 39: 3558-3588 and Tietze, L. F. and Kettschau, G. *Top. Curr. Chem.* (1997) 189: 1-120)

The choice of azides and alkynes as coupling partners is particularly advantageous as they are essentially non-reactive towards each other (in the absence of copper) and are extremely tolerant of other functional groups and reaction conditions. This chemical compatibility helps ensure that many different types of azides and alkynes may be coupled with each other with a minimal amount of side reactions.

The required copper(I) species are added directly as cuprous salts, for example CuI, CuOTf.C$_6$H$_6$ or [Cu (CH$_3$CN)$_4$][PF$_6$], usually with stabilizing ligands (see for example Tornøe, C. W.; Christensen, C. and Meldal, M. *J. Org. Chem.* (2002) 67: 3057-3064; Chan, T. R. et al., *Org. Lett.* (2004) 6: 2853-2855; Lewis, W. G. et al., *J. Am. Chem. Soc.* (2004) 126: 9152-9153; Mantovani, G. et al., *Chem. Comm.* (2005) 2089-2091; Diez-Gonzalez, S. et al., *Chem. Eur. J.* (2006) 12: 7558-7564 and Candelon, N. et al., *Chem. Comm.* (2008) 741-743), or more often generated from copper (II) salts with reducing agents (Rostovtsev, V. V. et al., *Angew. Chem.* (2002) 114: 2708-2711 and *Angew. Chem., Int. Ed.* (2002) 41: 2596-2599). Metallic copper (for example see Himo, F. et al., *J. Am. Chem. Soc.* (2005) 127: 210-216) or clusters (for example see Pachon, L. D. et al., *Adv. Synth. Catal.* (2005) 347: 811-815 and Molteni, G. et al., *New J. Chem* (2006) 30: 1137-1139) can also be employed. Chassaing et al., recently reported copper(I) zeolites as catalysts for the azide-alkyne cycloaddition (*Chem. Eur. J.* (2008) 14: 6713-6721). As copper(I) salts are prone to redox process, nitrogen- or phosphorous-based ligands must be added to protect and stabilize the active copper catalyst during the cycloaddition reaction.

The reaction is extremely straightforward. The azide and alkyne are usually mixed together in water and a co-solvent such as tert-butanol, THF, DMSO, toluene or DMF. The water/co-solvent are usually in a 1:1 to 1:9 ratio. The reactions are usually run overnight although mild heating shortens reaction times (Sharpless, W. D.; Wu, P.; Hansen, T. V.; and Li, J. G. *J. Chem. Ed.* (2005) 82: 1833). Aqueous systems can also use copper(I) species directly such that a reducing agent is not needed. The reactions conditions then usually require acetonitrile as a co-solvent (although not essential (Chan, T. R.; Hilgraf, R.; Shrapless, K. B. and Fokin, V. V. *Org. Lett.* (2004) 6: 2853)) and a nitrogen base, such as triethylamine, 2,6-lutidine, pyridine and diisopropylamine. In this case copper(I) species is supplied as CuI, CuOTf.C$_6$H$_6$, or [Cu(CH$_3$CN)$_4$][PF$_6$](Rostoctsev, V. V.; Green L. G.; Fokin, V. V. and Shrapless, K. B. *Angew. Chem., Int. Ed.* (2002) 41: 2596-2599).

Although the water-based methods are attractive for many applications, solvent based azide-alkyne cycloaddition methods have found utility in situations when solubility and/or other problems arise, for example see:

Malkoch, M. et al., *Macromolecules* (2005) 38: 3663.

Gujadhur, R.; Venkataraman, D. and J. T. Kintigh. J. T. *Tet. Lett.* (2001) 42: 4791.

Laurent, B. A. and Grayson, S. M. *J. Am. Chem. Soc.* (2006) 128: 4238.

Opsteen, J. A.; van Hest, J. C. M. *Chem. Commun.* (2005) 57.

Tsarevsky, N. V.; Sumerlin, B. S. and Matyjaszewski, K. *Macromolecules* (2005) 38: 3558.

Johnson, J. A. et al., *J. Am. Chem. Soc.* (2006) 128: 6564.

Sumerlin, B. S. et al., *Macromolecules* (2005) 38: 7540.

Gao, H. F. and Matyjaszewski, K. *Macromolecules* (2006) 39: 4960.

Gao, H. et al, *Macromolecules* (2005) 38: 8979.

Vogt, A. P. and Sumerlin, B. S. *Macromolecules* (2006) 39: 5286.

Lutz, J. F.; Borner, H. G. and Weichenhan, K. *Macromol. Rapid Comm.* (2005) 26: 514.

Mantovani, G.; Ladmiral, V.; Tao, L. and Haddleton, D. M. *Chem. Comm.* (2005) 2089.

The click reaction may be performed thermally. In one aspect, the click reaction is performed at slightly elevated temperatures between 25° C. and 100° C. In one aspect, the reaction may be performed between 25° C. and 75° C., or between 25° C. and 65° C., or between 25° C. and 50° C. In one embodiment, the reaction is performed at room temperature. In another aspect, the click reaction may also be performed using a microwave oven. The microwave assisted click reaction may be carried out in the presence or absence of copper.

In one aspect, the invention provides a method for coupling a click-carrier compound to a ligand through a click reaction. In a preferred embodiment, the click reaction is a cycloaddition reaction of azide with alkynyl group and catalyzed by copper. In one embodiment the equal molar amount of alkyne and azide are mixed together in DCM/MeOH (10:1 to 1:1 ratio v/v) and 0.05-0.5 mol % each of [Cu(CH$_3$CN)$_4$][PF$_6$] and copper are added the reaction. In one embodiment DCM/MeOH ratio is 5:1 to 1:1. In a preferred embodiment, DCM/MeOH ratio is 4:1. In one embodiment, equal molar amounts of [Cu(CH$_3$CN)$_4$][PF$_6$] and copper are added. In a preferred embodiment, 0.05-0.25 mol % each of [Cu(CH$_3$CN)$_4$][PF$_6$] and copper are added to the reaction. In a more preferred embodiment, 0.05 mol %, 0.1 mol %, 0.15 mol %, 0.2 mol % or 0.25 mol % each of [Cu(CH$_3$CN)$_4$][PF$_6$] and copper are added to the reaction.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the oligomeric compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

Ligands

A wide variety of entities can be coupled to the oligonucleotide, e.g. the iRNA agent, using the "click" reaction. Preferred entities can be coupled to the oligonucleotide at various places, for example, 3'-end, 5'-end, and/or at internal positions.

In preferred embodiments, the ligand is attached to the iRNA agent via an intervening linker. The ligand may be present on a compound when said compound is incorporated into the growing strand. In some embodiments, the ligand may be incorporated via coupling to a "precursor" compound after said "precursor" compound has been incorporated into the growing strand. For example, a compound having, e.g., an azide terminated linker (i.e., having no associated ligand), e.g., -linker-N$_3$ may be incorporated into a growing sense or antisense strand. In a subsequent operation, i.e., after incorporation of the precursor compound into the strand, a ligand having an alkyne, e.g. terminal acetylene, e.g. ligand-C≡CH, can subsequently be attached to the precursor compound by the "click" reaction. Alternatively, the compound linker comprises an alkyne, e.g. terminal acetylene; and the ligand comprises an azide functionality for the "click" reaction to take place. The azide or alkyne functionalities can be incorporated into the ligand by methods known in the art. For example, moieties carrying azide or alkyne functionalities can be linked to the ligand or a functional group on the ligand can be transformed into an azide or alkyne. In one embodiment, the conjugation of the ligand to the precursor compound takes place while the oligonucleotide is still attached to the solid support. In one embodiment, the precursor carrying oligonucleotide is first deprotected but not purified before the ligand conjugation takes place. In one embodiment, the precursor compound carrying oligonucleotide is first deprotected and purified before the ligand conjugation takes place. In certain embodiments, the "click" reaction is carried out under microwave.

In preferred embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Preferred ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In certain embodiments, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In certain embodiments, the endosomolytic component may contain a chemical group (e.g., an amino acid) which will undergo a change in charge or protonation in response to a change in pH. The endosomolytic component may be linear or branched. Exemplary primary sequences of peptide based endosomolytic ligands are shown in table 1.

TABLE 1

List of peptides with endosomolytic activity.

| Name | Sequence (N to C) | Ref. | SEQ ID NO: |
|---|---|---|---|
| GALA | AALEALAEALEALAEALEALAEAAAAGGC | 1 | 1 |
| EALA | AALAEALAEALAEALAEALAEALAAAAGGC | 2 | 2 |
|  | ALEALAEALEALAEA | 3 | 3 |
| INF-7 | GLFEAIEGFIENGWEGMIWDYG | 4 | 4 |
| Inf HA-2 | GLFGAIAGFIENGWEGMIDGWYG | 5 | 5 |
| diINF-7 | GLF EAI EGFI ENGW EGMI DGWYGC GLF EAI EGFI ENGW EGMI DGWYGC | 5 | 6 6 |
| diINF3 | GLF EAI EGFI ENGW EGMI DGGC GLF EAI EGFI ENGW EGMI DGGC | 6 | 7 7 |
| GLF | GLFGALAEALAEALAEHLAEALAEALEALAAGGSC | 6 | 8 |
| GALA-INF3 | GLFEAIEGFIENGWEGLAEALAEALEALAAGGSC | 6 | 9 |

TABLE 1-continued

List of peptides with endosomolytic activity.

| Name | Sequence (N to C) | Ref. | SEQ ID NO: |
|---|---|---|---|
| INF-5 | GLF EAI EGFI ENGW EGnI DG K | 4 | 10 |
| | GLF EAI EGFI ENGW EGnI DG | | 11 | n, norleucine
References
1 Subbarao et al. (1987) Biochemistry 26: 2964-2972.
2 Vogel, et al. (1996)J. Am. Chem. Soc. 118: 1581-1586
3 Turk, et al. (2002) Biochim. Biophys. Acta 1559: 56-68.
4 Plank, et al. (1994) J. Biol. Chem. 269: 12918-12924.
5 Mastrobattista, et al. (2002) J. Biol. Chem. 277: 27135-43.
6 Oberhauser, et al. (1995) Deliv. Strategies Antisense Oligonucleotide Ther. 247-66.

Preferred ligands can improve transport, hybridization, and specificity properties and may also improve nuclease resistance of the resultant natural or modified oligoribonucleotide, or a polymeric molecule comprising any combination of compounds described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 2 shows some examples of targeting ligands and their associated receptors.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

TABLE 2

Liver targeting Ligands and their associated receptors

| Liver Cells | Ligand | Receptor |
|---|---|---|
| 1) Parenchymal Cell (PC) (Hepatocytes) | Galactose | ASGP-R (Asiologlycoprotein receptor) |
| | Gal NAc (n-acetyl-galactosamine) | ASPG-R (GalNAc Receptor) |
| | Lactose | |
| | Asialofetuin | ASPG-r |
| 2) Sinusoidal Endothelial Cell (SEC) | Hyaluronan | Hyaluronan receptor |
| | Procollagen | Procollagen receptor |
| | Negatively charged molecules | Scavenger receptors |
| | Mannose | Mannose receptors |
| | N-acetyl Glucosamine | Scavenger receptors |
| | Immunoglobulins | Fc Receptor |
| | LPS | CD14 Receptor |
| | Insulin | Receptor mediated transcytosis |
| | Transferrin | Receptor mediated transcytosis |
| | Albumins | Non-specific |
| | Sugar-Albumin conjugates | |
| | Mannose-6-phosphate | Mannose-6-phosphate receptor |
| 3) Kupffer Cell (KC) | Mannose | Mannose receptors |
| | Fucose | Fucose receptors |
| | Albumins | Non-specific |
| | Mannose-albumin conjugates | |

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent fucose, or aptamers. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the iRNA agent into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver.

Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells.

Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long (see Table 3, for example).

TABLE 3

Exemplary Cell Permeation Peptides

| Cell Permeation Peptide | Amino acid Sequence | SEQ ID NO: | Reference |
|---|---|---|---|
| Penetratin | RQIKIWFQNRRMKWKK | 12 | Derossi et al., J. Biol. Chem. 269: 10444, 1994 |
| Tat fragment (48-60) | GRKKRRQRRRPPQ | 13 | Vives et al., J. Biol. Chem., 272: 16010, 1997 |
| Signal Sequence-based peptide | GALFLGWLGAAGSTMGAWSQP KKKRKV | 14 | Chaloin et al., Biochem. Biophys. Res. Commun., 243: 601, 1998 |
| PVEC | LLIILRRRIRKQAHAHSK | 15 | Elmquist et al., Exp. Cell Res., 269: 237, 2001 |
| Transportan | GWTLNSAGYLLKINLKALAALA KKIL | 16 | Pooga et al., FASEB J., 12: 67, 1998 |
| Amphiphilic model peptide | KLALKLALKALKAALKLA | 17 | Oehlke et al., Mol. Ther., 2: 339, 2000 |
| Arg$_9$ | RRRRRRRRR | 18 | Mitchell et al., J. Pept. Res., 56: 318, 2000 |
| Bacterial cell wall permeating | KFFKFFKFFK | 19 | |
| LL-37 | LLGDFFRKSKEKIGKEFKRIVQRI KDFLRNLVPRTES | 20 | |
| Cecropin P1 | SWLSKTAKKLENSAKKRISEGIAI AIQGGPR | 21 | |
| α-defensin | ACYCRIPACIAGERRYGTCIYQGR LWAFCC | 22 | |
| b-defensin | DHYNCVSSGGQCLYSACPIFTKIQ GTCYRGKAKCCK ) | 23 | |
| Bactenecin | RKCRIVVIRVCR | 24 | |
| PR-39 | RRRPRPPYLPRPRPPPFPPRLPPR IPPGFPPRFPPRFPGKR-NH$_2$ | 25 | |
| Indolicidin | ILPWKWPWWPWRR-NH$_2$ | 26 | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 27). An RFGF analogue (e.g., amino acid sequence AALLPVLLAAP (SEQ ID NO: 28)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 13)) and the *Drosophila* Antennapedia protein (RQIKIWFQNRRMKWKK (SEQ ID NO: 29)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated compound unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001).

Peptides that target markers enriched in proliferating cells can be used. E.g., RGD containing peptides and peptidomimetics can target cancer cells, in particular cells that exhibit an $I_v\theta_3$ integrin. Thus, one could use RGD peptides, cyclic peptides containing RGD, RGD peptides that include D-amino acids, as well as synthetic RGD mimics. In addition to RGD, one can use other moieties that target the $I_v$-$\theta_3$ integrin ligand. Generally, such ligands can be used to control proliferating cells and angiogeneis. Preferred conjugates of this type ligands that targets PECAM-1, VEGF, or other cancer gene, e.g., a cancer gene described herein.

TABLE 4

Azide modified peptides (SEQ ID NOS 30, 30, 31, 31, 18, and 18, respectively, in order of appearance).

| | |
|---|---|
| NB12675 | $N_3$-$(CH_2)_5$-CO-Tyr-Gly-Arg-Lys-Lys-Arg-Arg-Gln-Arg-Arg-Arg-Pro-Pro-Gln-$NH_2$ |
| NB12707 | $N_3$-$(CH_2)_{15}$-CO-Tyr-Gly-Arg-Lys-Lys-Arg-Arg-Gln-Arg-Arg-Arg-Pro-Pro-Gln-$NH_2$ |
| NB12676 | cyclo-[Phe-Arg-Gly-Asp-Lys($N_3$-$(CH_2)_5$-COOH)] |
| NB12708 | cyclo-[Phe-Arg-Gly-Asp-Lys($N_3$-$(CH_2)_{15}$-COOH)] |

TABLE 4-continued

Azide modified peptides (SEQ ID NOS 30, 30, 31, 31, 18, and 18, respectively, in order of appearance).

| | |
|---|---|
| NB12709 | $N_3$-$(CH2)_5$-CO-Arg-Arg-Arg-Arg-Arg-Arg-Arg-Arg-$NH_2$ |
| NB12710 | $N_3$-$(CH2)_{15}$-CO-Arg-Arg-Arg-Arg-Arg-Arg-Arg-Arg-$NH_2$ |

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide tethered to an iRNA agent and/or the carrier oligomer can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, $H_2A$ peptides, *Xenopus* peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic compoundic units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, $GalNAc_3$, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycaboxylates, polyacations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Exemplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as ligands (e.g. as PK modulating ligands).

In addition, aptamers that bind serum components (e.g. serum proteins) are also amenable to the present invention as PK modulating ligands.

Other ligands amenable to the invention are described in copending applications U.S. Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

The compound comprising the ligand, e.g. the click-carrier compound, can be present in any position of an oligonucleotide, e.g. an iRNA agent. In some embodiments, click-carrier compound can be present at the terminus such as a 5' or 3' terminal of the iRNA agent. Click-carrier compounds can also present at an internal position of the iRNA agent. For double-stranded iRNA agents, click-carrier compounds can be incorporated into one or both strands. In some embodiments, the sense strand of the double-stranded iRNA agent comprises the click-carrier compound. In other embodiments, the antisense strand of the double-stranded iRNA agent comprises the click-carrier compound.

In some embodiments, ligands can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligomeric compounds. Generally, an oligomeric compound is attached to a conjugate moiety by contacting a reactive group (e.g., OH, SH, amine, carboxyl, aldehyde, and the like) on the oligomeric compound with a reactive group on the conjugate moiety. In some embodiments, one reactive group is electrophilic and the other is nucleophilic.

For example, an electrophilic group can be a carbonyl-containing functionality and a nucleophilic group can be an amine or thiol. Methods for conjugation of nucleic acids and related oligomeric compounds with and without linkers are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

Representative United States patents that teach the preparation of oligonucleotide conjugates include, but are not limited to, U.S. Pat. Nos. 4,828,979; 4,948,882; 5,218, 105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254, 469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559,279; each of which is herein incorporated by reference.

Oligonucleotide

The term "oligonucleotide" as used herein refers to an unmodified RNA, modified RNA, or nucleoside surrogate, all of which are defined herein. Although the modifications are described in context of an iRNA agent, it is understood that these modifications are also applicable to other oligonucleotides of the invention such as antisense, antagomir, aptamer, ribozyme and decoy oligonucleotides. While numerous modified RNAs and nucleoside surrogates are described, preferred examples include those which have greater resistance to nuclease degradation than do unmodified RNAs. Preferred examples include those which have a 2' sugar modification, a modification in a single strand overhang, preferably a 3' single strand overhang, or, particularly if single stranded, a 5' modification which includes one or more phosphate groups or one or more analogs of a phosphate group.

An "iRNA agent" as used herein, is an RNA agent which can, or which can be cleaved into an RNA agent which can, down regulate the expression of a target gene, preferably an endogenous or pathogen target RNA. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand or can include more than one strands, e.g., it can be a double stranded iRNA agent. If the iRNA agent is a single strand it is particularly preferred that it include a 5' modification which includes one or more phosphate groups or one or more analogs of a phosphate group. If the iRNA agent is double stranded the double stranded region can include more than two or more strands, e.g., two strands, e.g. three strands, in the double stranded region.

The iRNA agent should include a region of sufficient homology to the target gene, and be of sufficient length in terms of nucleotides, such that the iRNA agent, or a fragment thereof, can mediate down regulation of the target gene. (For ease of exposition the term nucleotide or ribonucleotide is sometimes used herein in reference to one or more compoundic subunits of an RNA agent. It will be understood herein that the usage of the term "ribonucleotide" or "nucleotide", herein can, in the case of a modified RNA or nucleotide surrogate, also refer to a modified nucleotide, or surrogate replacement moiety at one or more positions.) Thus, the iRNA agent is or includes a region which is at least partially, and in some embodiments fully, complementary to the target RNA. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA.

An iRNA agent will often be modified or include nucleoside surrogates in addition to the click-carrier compound. Single stranded regions of an iRNA agent will often be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an iRNA agent, e.g., against exonucleases, or to favor the antisense sRNA agent to enter into RISC are also favored. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

A "single strand iRNA agent" as used herein, is an iRNA agent which is made up of a single molecule. It may include a duplexed region, formed by intra-strand pairing, e.g., it may be, or include, a hairpin or pan-handle structure. Single strand iRNA agents are preferably antisense with regard to the target molecule. In preferred embodiments single strand iRNA agents are 5'-phosphorylated or include a phosphoryl analog at the 5'-terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g. RP(OH)(O)—O-5'-, (OH)$_2$(O)P-5'-CH$_2$—), 5'-alkyletherphosphonates (R=alkylether=methoxymethyl (MeOCH$_2$—), ethoxymethyl, etc., e.g. RP(OH)(O)—O-5'-). (These modifications can also be used with the antisense strand of a multi-strand iRNA agent.)

A "multi-strand iRNA agent" as used herein, is an iRNA agent which comprises two or more strands, for example a double-stranded iRNA agent. The strands form duplexed regions and may include a hairpin, pan-handle structure, loop or bulges. At least one strand of the iRNA agent is preferably antisense with regard to the target molecule.

It may be desirable to modify only one, only two or all strands of a multi-strand iRNA agent. In some cases they will have the same modification or the same class of modification but in other cases the different strand will have different modifications, e.g., in some cases it is desirable to modify only one strand. It may be desirable to modify only some strands, e.g., to inactivate them, e.g., strands can be modified in order to inactivate them and prevent formation of an active iRNA/protein or RISC. This can be accomplished by a modification which prevents 5'-phosphorylation of the strands, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage, though this may be less desirable as phosphodiesterases can cleave such a linkage and release a functional iRNA 5'-end. Antisense strand modifications include 5'-phosphorylation as well as any of the other 5' modifications discussed herein, particularly the 5' modifications discussed above in the section on single stranded iRNA molecules.

In some cases, the different strands will include different modifications. Multiple different modifications can be included on each of the strands. The modifications on a given strand may differ from each other, and may also differ from the various modifications on other strands. For example, one strand may have a modification, e.g., a modification described herein, and a different strand may have a different modification, e.g., a different modification described herein. In other cases, one strand may have two or more different modifications, and the another strand may include a modification that differs from the at least two modifications on the other strand.

It is preferred that the strands be chosen such that the iRNA agent includes a single strand or unpaired region at one or both ends of the molecule. Thus, an iRNA agent contains two or more strands, preferable paired to contain an overhang, e.g., one or two 5' or 3' overhangs but preferably a 3' overhang of 2-3 nucleotides. Most embodiments will have a 3' overhang. Preferred iRNA agents will have single-stranded overhangs, preferably 3' overhangs, of 1 or preferably 2 or 3 nucleotides in length at each end. The overhangs can be the result of one strand being longer than the other, or the result of two strands of the same length being staggered.

Preferred lengths for the duplexed regions between the strands are between 6 and 30 nucleotides in length. The preferred duplexed regions are between 15 and 30, most preferably 18, 19, 20, 21, 22, and 23 nucleotides in length. Other preferred duplexed regions are between 6 and 20 nucleotides, most preferably 6, 7, 8, 9, 10, 11 and 12 nucleotides in length. In multi-strand iRNA agents different duplexes formed may have different lengths, e.g. duplexed region formed between strand A and B may have a different length than duplexed region formed between strand A and C.

In iRNA agents comprising more than two strands duplexed agents can resemble in length and structure the natural Dicer processed products from long dsRNAs. Embodiments in which the two or more strands of the iRNA agent are linked, e.g., covalently linked are also included. Hairpins or other single strand structures which provide the required double stranded region, and preferably a 3' overhang are also within the invention.

As nucleic acids are polymers of subunits or compounds, many of the modifications described below occur at a position which is repeated within a nucleic acid, e.g., a modification of a base, or a phosphate moiety, or the non-bridging oxygen of a phosphate moiety. In some cases the modification will occur at all of the subject positions in the nucleic acid but in many, and in fact in most cases it will not. By way of example, a modification may only occur at a 3' or 5' terminal position, may only occur in the internal unpaired region, may only occur in a terminal regions, e.g. at a position on a terminal nucleotide or in the last 2, 3, 4, 5, or 10 nucleotides of a strand. A modification may occur in a double strand region, a single strand region, or in both. A modification may occur only in the double strand region of an RNA agent or may only occur in a single strand region of an RNA agent. E.g., a phosphorothioate modification at a non-bridging oxygen position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

In some embodiments it is particularly preferred, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Specific modifications are discussed in more detail below. Although, the modifications herein are described in context of an iRNA agent, these modifications are also amenable in modifying the carrier oligonucleotides of the invention.

The Phosphate Group

The phosphate group is a negatively charged species. The charge is distributed equally over the two non-bridging oxygen atoms. However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-bridging oxygens replaced by sulfur. The phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both non-bridging oxygens, which eliminate the chiral center, e.g. phosphorodithioate formation, may be desirable in that they cannot produce diastereomer mixtures. Thus, the non-bridging oxygens can be independently any one of S, Se, B, C, H, N, or OR (R is alkyl or aryl). Replacement of the non-bridging oxygens with sulfur is preferred.

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. When the bridging oxygen is the 3'-oxygen of a nucleoside, replacement with carbon is preferred. When the bridging oxygen is the 5'-oxygen of a nucleoside, replacement with nitrogen is preferred.

Replacement of the Phosphate Group

The phosphate group can be replaced by non-phosphorus containing connectors. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Modified phosphate linkages where at least one of the oxygens linked to the phosphate has been replaced or the phosphate group has been replaced by a non-phosphorous group, are also referred to as "non phosphodiester backbone linkage."

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morphilino, cyclobutyl, pyrrolidine and peptide nucleic acid (PNA) nucleoside surrogates. A preferred surrogate is a PNA surrogate.

Sugar Modifications

A modified RNA can include modification of all or some of the sugar groups of the ribonucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)CH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thioalkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH3, 2'-O-allyl, 2'-C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNAs can also include "abasic" sugars, which lack a nucleobase at C-1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

The modification can also entail the wholesale replacement of a ribose structure with another entity at one or more sites in the iRNA agent.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —$(CH_2)_n$—, —$(CH_2)_nN$—, —$(CH_2)_nO$—, —$(CH_2)_nS$—, $O(CH_2CH_2O)_nCH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents. When a spacer/phosphate-functional molecular entity-spacer/phosphate array is interposed between two strands of iRNA agents, this array can substitute for a hairpin RNA loop in a hairpin-type RNA agent. The 3' end can be an —OH group. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Terminal modifications useful for modulating activity include modification of the 5' end with phosphate or phosphate analogs. E.g., in preferred embodiments iRNA agents, especially antisense strands, are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5');
5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-).

Terminal modifications can also be useful for monitoring distribution, and in such cases the preferred groups to be added include fluorophores, e.g., fluorscein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

Nucleobases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases", "modified bases", "non-natural bases" and "universal bases" described herein, can be employed. Examples include without limitation 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Generally, base changes are less preferred for promoting stability, but they can be useful for other reasons, e.g., some, e.g., 2,6-diaminopurine and 2 amino purine, are fluorescent. Modified bases can reduce target specificity. This should be taken into consideration in the design of iRNA agents.

Cationic Groups

Modifications can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=NH$_2$; alkylamino, dialkylamino, heterocyclyl, arylamino, diaryl amino, heteroaryl amino, or diheteroaryl amino, ethylene diamine, polyamino); aminoalkoxy, e.g., O(CH$_2$)$_n$AMINE, (e.g., AMINE=NH$_2$; alkylamino, dialkylamino, heterocyclyl, arylamino, diaryl amino, heteroaryl amino, or diheteroaryl amino, ethylene diamine, polyamino); amino (e.g. NH$_2$; alkylamino, dialkylamino, heterocyclyl, arylamino, diaryl amino, heteroaryl amino, diheteroaryl amino, or amino acid); or NH(CH$_2$CH$_2$NH)CH$_2$CH$_2$-AMINE (AMINE=NH$_2$; alkylamino, dialkylamino, heterocyclyl, arylamino, diaryl amino, heteroaryl amino, or diheteroaryl amino).

Exemplary Modifications and Placement within an iRNA Agent

Some modifications may preferably be included on an iRNA agent at a particular location, e.g., at an internal position of a strand, or on the 5' or 3' end of a strand of an iRNA agent. A preferred location of a modification on an iRNA agent, may confer preferred properties on the agent. For example, preferred locations of particular modifications may confer optimum gene silencing properties, or increased resistance to endonuclease or exonuclease activity. A modification described herein and below may be the sole modification, or the sole type of modification included on multiple ribonucleotides, or a modification can be combined with one or more other modifications described herein and below. For example, a modification on one strand of a multi-strand iRNA agent can be different than a modification on another strand of the multi-strand iRNA agent. Similarly, two different modifications on one strand can differ from a modification on a different strand of the iRNA agent. Other additional unique modifications, without limitation, can be incorporates into strands of the iRNA agent.

An iRNA agent may include a backbone modification to any nucleotide on an iRNA strand. For example, an iRNA agent may include a phosphorothioate linkage or P-alkyl modification in the linkages between one or more nucleotides of an iRNA agent. The nucleotides can be terminal nucleotides, e.g., nucleotides at the last position of a sense or antisense strand, or internal nucleotides.

An iRNA agent can include a sugar modification, e.g., a 2' or 3' sugar modification. Exemplary sugar modifications include, for example, a 2'-O-methylated nucleotide, a 2'-deoxy nucleotide, (e.g., a 2'-deoxyfluoro nucleotide), a 2'-O-methoxyethyl nucleotide, a 2'-O-NMA, a 2'-DMAEOE, a 2'-aminopropyl, 2'-hydroxy, or a 2'-ara-fluoro or a locked nucleic acid (LNA), extended nucleic acid (ENA), hexose nucleic acid (HNA), or cyclohexene nucleic acid (CeNA). A 2' modification is preferably 2'-OMe, and more preferably, 2'-deoxyfluoro. When the modification is 2'-OMe, the modification is preferably on the sense strands. When the modification is a 2'-fluoro, and the modification may be on any strand of the iRNA agent. A 2'-ara-fluoro modification will preferably be on the sense strands of the iRNA agent. An iRNA agent may include a 3' sugar modification, e.g., a 3'-OMe modification. Preferably a 3'-OMe modification is on the sense strand of the iRNA agent.

An iRNA agent may include a 5'-methyl-pyrimidine (e.g., a 5'-methyl-uridine modification or a 5'-methyl-cytodine) modification.

The modifications described herein can be combined onto a single iRNA agent. For example, an iRNA agent may have a phosphorothioate linkage and a 2' sugar modification, e.g., a 2'-OMe or 2'-F modification. In another example, an iRNA agent may include at least one 5-Me-pyrimidine and a 2'-sugar modification, e.g., a 2'-F or 2'-OMe modification.

An iRNA agent may include a nucleobase modification, such as a cationic modification, such as a 3'-abasic cationic modification. The cationic modification can be e.g., an alkylamino-dT (e.g., a C6 amino-dT), an allylamino conjugate, a pyrrolidine conjugate, a pthalamido, a porphyrin, or a hydroxyprolinol conjugate, on one or more of the terminal nucleotides of the iRNA agent. When an alkylamino-dT conjugate is attached to the terminal nucleotide of an iRNA agent, the conjugate is preferably attached to the 3' end of the sense or antisense strand of an iRNA agent. When a pyrrolidine linker is attached to the terminal nucleotide of an iRNA agent, the linker is preferably attached to the 3'- or 5'-end of the sense strand, or the 3'-end of the antisense strand. When a pyrrolidine linker is attached to the terminal nucleotide of an iRNA agent, the linker is preferably on the 3'- or 5'-end of the sense strand, and not on the 5'-end of the antisense strand.

An iRNA agent may include at least one conjugate, such as a lipophile, a terpene, a protein binding agent, a vitamin, a carbohydrate, or a peptide. For example, the conjugate can be naproxen, nitroindole (or another conjugate that contributes to stacking interactions), folate, ibuprofen, or a C5 pyrimidine linker. The conjugate can also be a glyceride lipid conjugate (e.g., a dialkyl glyceride derivatives), vitamin E conjugate, or a thio-cholesterol. In generally, and except where noted to the contrary below, when a conjugate is on the terminal nucleotide of a sense or antisense strand, the conjugate is preferably on the 5' or 3' end of the sense strand or on the 5' end of the antisense strand, and preferably the conjugate is not on the 3' end of the antisense strand.

When the conjugate is naproxen, and the conjugate is on the terminal nucleotide of a sense or antisense strand, the conjugate is preferably on the 5' or 3' end of the sense or antisense strands. When the conjugate is cholesterol, and the conjugate is on the terminal nucleotide of a sense or antisense strand, the cholesterol conjugate is preferably on the 5' or 3' end of the sense strand and preferably not present on the antisense strand. Cholesterol may be conjugated to the iRNA agent by a pyrrolidine linker, serinol linker, hydroxyprolinol linker, or disulfide linkage. A dU-cholesterol conjugate may also be conjugated to the iRNA agent by a disulfide linkage. When the conjugate is cholanic acid, and the conjugate is on the terminal nucleotide of a sense or antisense strand, the cholanic acid is preferably attached to the 5' or 3' end of the sense strand, or the 3' end of the antisense strand. In one embodiment, the cholanic acid is attached to the 3' end of the sense strand and the 3' end of the antisense strand.

One or more nucleotides of an iRNA agent may have a 2'-5' linkage. Preferably, the 2'-5' linkage is on the sense strand. When the 2'-5' linkage is on the terminal nucleotide of an iRNA agent, the 2'-5' linkage occurs on the 5' end of the sense strand.

The iRNA agent may include an L-sugar, preferably on the sense strand, and not on the antisense strand.

The iRNA agent may include a methylphosphonate modification. When the methylphosphonate is on the terminal nucleotide of an iRNA agent, the methylphosphonate is at the 3' end of the sense or antisense strands of the iRNA agent.

An iRNA agent may be modified by replacing one or more ribonucleotides with deoxyribonucleotides. Preferably, adjacent deoxyribonucleotides are joined by phosphorothioate linkages, and the iRNA agent does not include more than four consecutive deoxyribonucleotides on the sense or the antisense strands.

An iRNA agent may include a difluorotoluyl (DFT) modification, e.g., 2,4-difluorotoluyl uracil, or a guanidine to inosine substitution.

The iRNA agent may include at least one 5'-uridine-adenine-3' (5'-UA-3') dinucleotide wherein the uridine is a 2'-modified nucleotide, or a terminal 5'-uridine-guanine-3' (5'-UG-3') dinucleotide, wherein the 5'-uridine is a 2'-modified nucleotide, or a terminal 5'-cytidine-adenine-3' (5'-CA-3') dinucleotide, wherein the 5'-cytidine is a 2'-modified nucleotide, or a terminal 5'-uridine-uridine-3' (5'-UU-3') dinucleotide, wherein the 5'-uridine is a 2'-modified nucleotide, or a terminal 5'-cytidine-cytidine-3' (5'-CC-3') dinucleotide, wherein the 5'-cytidine is a 2'-modified nucleotide, or a terminal 5'-cytidine-uridine-3' (5'-CU-3') dinucleotide, wherein the 5'-cytidine is a 2'-modified nucleotide, or a terminal 5'-uridine-cytidine-3' (5'-UC-3') dinucleotide, wherein the 5'-uridine is a 2'-modified nucleotide. The chemically modified nucleotide in the iRNA agent may be a 2'-O-methylated nucleotide. In some embodiments, the modified nucleotide can be a 2'-deoxy nucleotide, a 2'-deoxyfluoro nucleotide, a 2'-O-methoxyethyl nucleotide, a 2'-O-NMA, a 2'-DMAEOE, a 2'-aminopropyl, 2'-hydroxy, or a 2'-ara-fluoro, or a locked nucleic acid (LNA), extended nucleic acid (ENA), hexose nucleic acid (HNA), or cyclohexene nucleic acid (CeNA). The iRNA agents including these modifications are particularly stabilized against exonuclease activity, when the modified dinucleotide occurs on a terminal end of the sense or antisense strand of an iRNA agent, and are otherwise particularly stabilized against endonuclease activity.

An iRNA agent may have a single overhang, e.g., one end of the iRNA agent has a 3' or 5' overhang and the other end of the iRNA agent is a blunt end, or the iRNA agent may have a double overhang, e.g., both ends of the iRNA agent have a 3' or 5' overhang, such as a dinucleotide overhang. In another alternative, both ends of the iRNA agent may have blunt ends. The unpaired nucleotides may have at least one phosphorothioate dinucleotide linkage, and at least one of the unpaired nucleotides may be chemically modified in the 2'-position. The doublestrand region of the iRNA agent may include phosphorothioate dinucleotide linkages on one or both of the sense and antisense strands. Various strands of the multi-strand iRNA agent may be connected with a linker, e.g., a chemical linker such as hexaethylene glycol linker, a poly-(oxyphosphinico-oxy-1,3-propandiol) linker, an allyl linker, or a polyethylene glycol linker.

Nuclease Resistant Compounds

An iRNA agent can include compounds which have been modified so as to inhibit degradation, e.g., by nucleases, e.g., endonucleases or exonucleases, found in the body of a subject. These compounds are referred to herein as NRMs, or nuclease resistance promoting compounds or modifications. In many cases these modifications will modulate other properties of the iRNA agent as well, e.g., the ability to interact with a protein, e.g., a transport protein, e.g., serum albumin, or a member of the RISC (RNA-induced Silencing Complex), or the ability of the first and second sequences to form a duplex with one another or to form a duplex with another sequence, e.g., a target molecule.

While not wishing to be bound by theory, it is believed that modifications of the sugar, base, and/or phosphate backbone in an iRNA agent can enhance endonuclease and exonuclease resistance, and can enhance interactions with transporter proteins and one or more of the functional components of the RISC complex. Preferred modifications are those that increase exonuclease and endonuclease resistance and thus prolong the half-life of the iRNA agent prior to interaction with the RISC complex, but at the same time do not render the iRNA agent resistant to endonuclease activity in the RISC complex. Again, while not wishing to be bound by any theory, it is believed that placement of the modifications at or near the 3' and/or 5' end of antisense strands can result in iRNA agents that meet the preferred nuclease resistance criteria delineated above. Again, still while not wishing to be bound by any theory, it is believed that placement of the modifications at e.g., the middle of a sense strand can result in iRNA agents that are relatively less likely to undergo off-targeting.

Modifications described herein can be incorporated into any RNA and RNA-like molecule described herein, e.g., an iRNA agent, a carrier oligonucleotide. An iRNA agent may include a duplex comprising a hybridized sense and antisense strand, in which the antisense strand and/or the sense strand may include one or more of the modifications described herein. The anti sense strand may include modifications at the 3' end and/or the 5' end and/or at one or more positions that occur 1-6 (e.g., 1-5, 1-4, 1-3, 1-2) nucleotides from either end of the strand. The sense strand may include modifications at the 3' end and/or the 5' end and/or at any one of the intervening positions between the two ends of the strand. The iRNA agent may also include a duplex comprising two hybridized antisense strands. The first and/or the second antisense strand may include one or more of the modifications described herein. Thus, one and/or both anti-sense strands may include modifications at the 3' end and/or the 5' end and/or at one or more positions that occur 1-6 (e.g., 1-5, 1-4, 1-3, 1-2) nucleotides from either end of the strand. Particular configurations are discussed below.

Modifications that can be useful for producing iRNA agents that meet the preferred nuclease resistance criteria delineated above can include one or more of the following chemical and/or stereochemical modifications of the sugar, base, and/or phosphate backbone:

(i) chiral ($S_P$) thioates. Thus, preferred NRMs include nucleotide dimers with an enriched or pure for a particular chiral form of a modified phosphate group containing a heteroatom at the nonbridging position, e.g., Sp or Rp, where this is the position normally occupied by the oxygen. The heteroatom can be S, Se, $NR_2$, or $BR_3$. When the heteroatom is S, enriched or chirally pure Sp linkage is preferred. Enriched means at least 70, 80, 90, 95, or 99% of the preferred form. Such NRMs are discussed in more detail below;

(ii) attachment of one or more cationic groups to the sugar, base, and/or the phosphorus atom of a phosphate or modified phosphate backbone moiety. Thus, preferred NRMs include compounds at the terminal position derivatized at a cationic group. As the 5' end of an antisense sequence should have a terminal —OH or phosphate group this NRM is preferably not used at the 5' end of an anti-sense sequence. The group should be attached at a position on the base which minimizes interference with H bond formation and hybridization, e.g., away form the face which interacts with the complementary base on the other strand, e.g, at the 5' position of a pyrimidine or a 7-position of a purine. These are discussed in more detail below;

(iii) nonphosphate linkages at the termini. Thus, preferred NRMs include Non-phosphate linkages, e.g., a linkage of 4 atoms which confers greater resistance to cleavage than does a phosphate bond. Examples include 3' $CH_2$—$NCH_3$—O—$CH_2$-5' and 3' $CH_2$—NH—(O=C)—$CH_2$-5';

(iv) 3'-bridging thiophosphates and 5'-bridging thiophosphates. Thus, preferred NRM's can included these structures;

(v) L-RNA, 2'-5' linkages, inverted linkages, a-nucleosides. Thus, other preferred NRM's include: L nucleosides and dimeric nucleotides derived from L-nucleosides; 2'-5' phosphate, non-phosphate and modified phosphate linkages (e.g., thiophosphates, phosphoramidates and boronophosphates); dimers having inverted linkages, e.g., 3'-3' or 5'-5' linkages; compounds having an alpha linkage at the 1' site on the sugar, e.g., the structures described herein having an alpha linkage;

(vi) conjugate groups. Thus, preferred NRM's can include e.g., a targeting moiety or a conjugated ligand described herein conjugated with the compound, e.g., through the sugar, base, or backbone;

(vii) abasic linkages. Thus, preferred NRM's can include an abasic compound, e.g., an abasic compound as described herein (e.g., a nucleobaseless compound); an aromatic or heterocyclic or polyheterocyclic aromatic compound as described herein; and (viii) 5'-phosphonates and 5'-phosphate prodrugs. Thus, preferred NRM's include compounds, preferably at the terminal position, e.g., the 5' position, in which one or more atoms of the phosphate group is derivatized with a protecting group, which protecting group or groups, are removed as a result of the action of a component in the subject's body, e.g, a carboxyesterase or an enzyme present in the subject's body. E.g., a phosphate prodrug in which a carboxy esterase cleaves the protected molecule resulting in the production of a thioate anion which attacks a carbon adjacent to the O of a phosphate and resulting in the production of an unprotected phosphate.

One or more different NRM modifications can be introduced into an iRNA agent or into a sequence of an iRNA agent. An NRM modification can be used more than once in a sequence or in an iRNA agent. As some NRM's interfere with hybridization the total number incorporated, should be such that acceptable levels of iRNA agent duplex formation are maintained.

In some embodiments NRM modifications are introduced into the terminal the cleavage site or in the cleavage region of a sequence (a sense strand or sequence) which does not target a desired sequence or gene in the subject. This can reduce off-target silencing.

REFERENCES

General References

The oligoribonucleotides and oligoribonucleosides used in accordance with this invention may be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotides: synthesis and applications, Chapter 4, Phosphorothioate oligonucleotides, Chapter 5, Synthesis of oligonucleotide phosphorodithioates, Chapter 6, Synthesis of oligo-2'- deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta*, 1995, 78, 486-504; Beaucage, S. L. and Iyer, R. P., *Tetrahedron*, 1992, 48, 2223-2311 and Beaucage, S. L. and Iyer, R. P., *Tetrahedron*, 1993, 49, 6123-6194, or references referred to therein.

Modification described in WO 00/44895, WO01/75164, or WO02/44321 can be used herein.

The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. No. 5,256,775 or U.S. Pat. No. 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Sugar Group References

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.*, 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489, 677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc.* *Perkin Trans.* 1 1972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. *Antisense and Nucleic Acid Drug Development* 12, 103-128 (2002) and references therein.

Bases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references are disclosed in the above section on base modifications.

Oligonucleotide Production

The oligonucleotide compounds of the invention can be prepared using solution-phase or solid-phase organic synthesis. Organic synthesis offers the advantage that the oligonucleotide strands comprising non-natural or modified nucleotides can be easily prepared. Any other means for such synthesis known in the art may additionally or alternatively be employed. It is also known to use similar techniques to prepare other oligonucleotides, such as the phosphorothioates, phosphorodithioates and alkylated derivatives. The double-stranded oligonucleotide compounds of the invention may be prepared using a two-step procedure. First, the individual strands of the double-stranded molecule are prepared separately. Then, the component strands are annealed.

Regardless of the method of synthesis, the oligonucleotide can be prepared in a solution (e.g., an aqueous and/or organic solution) that is appropriate for formulation. For example, the iRNA preparation can be precipitated and redissolved in pure double-distilled water, and lyophilized. The dried iRNA can then be resuspended in a solution appropriate for the intended formulation process.

Teachings regarding the synthesis of particular modified oligonucleotides may be found in the following U.S. patents or pending patent applications: U.S. Pat. Nos. 5,138,045 and 5,218,105, drawn to polyamine conjugated oligonucleotides; U.S. Pat. No. 5,212,295, drawn to compounds for the preparation of oligonucleotides having chiral phosphorus linkages; U.S. Pat. Nos. 5,378,825 and 5,541,307, drawn to oligonucleotides having modified backbones; U.S. Pat. No.

5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having .beta.-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

It is not necessary for all positions in a given compound to be uniformly modified, and in fact more than one type of modification may be incorporated in a single oligonucleotide compound or even in a single nucleotide thereof.

Routes of Delivery

For ease of exposition the formulations, compositions and methods in this section are discussed largely with regard to unmodified iRNA agents. It should be understood, however, that these formulations, compositions and methods can be practiced with other oligonucleotide of the invention, e.g., modified iRNA agents, antisense, antagomirs, apatamers, ribozymes, and such practice is within the invention. A composition that includes an iRNA can be delivered to a subject by a variety of routes. Exemplary routes include: intravenous, topical, rectal, anal, vaginal, nasal, pulmonary, ocular.

The iRNA molecules of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water, syrups, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers.

Topical Delivery

For ease of exposition the formulations, compositions and methods in this section are discussed largely with regard to unmodified iRNA agents. It should be understood, however, that these formulations, compositions and methods can be practiced with other oligonucleotides of the invention, e.g., modified iRNA agents, antisense, apatamer, antagomir and ribozyme, and such practice is within the invention. In a preferred embodiment, an iRNA agent is delivered to a subject via topical administration. "Topical administration" refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

The term "skin," as used herein, refers to the epidermis and/or dermis of an animal. Mammalian skin consists of two major, distinct layers. The outer layer of the skin is called the epidermis. The epidermis is comprised of the stratum corneum, the stratum granulosum, the stratum spinosum, and the stratum basale, with the stratum corneum being at the surface of the skin and the stratum basale being the deepest portion of the epidermis. The epidermis is between 50 µm and 0.2 mm thick, depending on its location on the body.

Beneath the epidermis is the dermis, which is significantly thicker than the epidermis. The dermis is primarily composed of collagen in the form of fibrous bundles. The collagenous bundles provide support for, inter alia, blood vessels, lymph capillaries, glands, nerve endings and immunologically active cells.

One of the major functions of the skin as an organ is to regulate the entry of substances into the body. The principal permeability barrier of the skin is provided by the stratum corneum, which is formed from many layers of cells in various states of differentiation. The spaces between cells in the stratum corneum is filled with different lipids arranged in lattice-like formations that provide seals to further enhance the skins permeability barrier.

The permeability barrier provided by the skin is such that it is largely impermeable to molecules having molecular weight greater than about 750 Da. For larger molecules to cross the skin's permeability barrier, mechanisms other than normal osmosis must be used.

Several factors determine the permeability of the skin to administered agents. These factors include the characteristics of the treated skin, the characteristics of the delivery agent, interactions between both the drug and delivery agent and the drug and skin, the dosage of the drug applied, the form of treatment, and the post treatment regimen. To selectively target the epidermis and dermis, it is sometimes possible to formulate a composition that comprises one or more penetration enhancers that will enable penetration of the drug to a preselected stratum.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy.

In addition, iontophoresis (transfer of ionic solutes through biological membranes under the influence of an electric field) (Lee et al., Critical Reviews in Therapeutic Drug Carrier Systems, 1991, p. 163), phonophoresis or sonophoresis (use of ultrasound to enhance the absorption of various therapeutic agents across biological membranes, notably the skin and the cornea) (Lee et al., Critical Reviews in Therapeutic Drug Carrier Systems, 1991, p. 166), and optimization of vehicle characteristics relative to dose position and retention at the site of administration (Lee et al., Critical Reviews in Therapeutic Drug Carrier Systems, 1991, p. 168) may be useful methods for enhancing the transport of topically applied compositions across skin and mucosal sites.

The compositions and methods provided may also be used to examine the function of various proteins and genes in vitro in cultured or preserved dermal tissues and in animals. The invention can be thus applied to examine the function of any gene. The methods of the invention can also be used therapeutically or prophylactically. For example, for the treatment of animals that are known or suspected to suffer from diseases such as psoriasis, lichen planus, toxic epidermal necrolysis, ertythema multiforme, basal cell carcinoma, squamous cell carcinoma, malignant melanoma, Paget's disease, Kaposi's sarcoma, pulmonary fibrosis, Lyme disease and viral, fungal and bacterial infections of the skin.

Pulmonary Delivery

For ease of exposition the formulations, compositions and methods in this section are discussed largely with regard to unmodified iRNA agents. It should be understood, however, that these formulations, compositions and methods can be practiced with other oligonucleotides of the invention, e.g., modified iRNA agents, antisense, apatamer, antagomir and ribozyme, and such practice is within the invention. A composition that includes an iRNA agent, e.g., a double-stranded iRNA agent, can be administered to a subject by pulmonary delivery. Pulmonary delivery compositions can be delivered by inhalation by the patient of a dispersion so that the composition, preferably iRNA, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. An iRNA composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 µm in diameter preferably with a relatively uniform spheroidal shape distribution. More preferably the diameter is less than about 7.5 µm and most preferably less than about 5.0 µm. Usually the particle size distribution is between about 0.1 µm and about 5 µm in diameter, particularly about 0.3 µm to about 5 µm.

The term "dry" means that the composition has a moisture content below about 10% by weight (% w) water, usually below about 5% w and preferably less it than about 3% w. A dry composition can be such that the particles are readily dispersible in an inhalation device to form an aerosol.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Additives, which are minor components of the composition of this invention, may be included for conformational stability during spray drying and for improving dispersibility of the powder. These additives include hydrophobic amino acids such as tryptophan, tyrosine, leucine, phenylalanine, and the like.

Suitable pH adjusters or buffers include organic salts prepared from organic acids and bases, such as sodium citrate, sodium ascorbate, and the like; sodium citrate is preferred.

Pulmonary administration of a micellar iRNA formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Oral or Nasal Delivery

For ease of exposition the formulations, compositions and methods in this section are discussed largely with regard to unmodified iRNA agents. It should be understood, however, that these formulations, compositions and methods can be practiced with other oligonucleotides of the invention, e.g., modified iRNA agents, antisense, apatamer, antagomir and ribozyme, and such practice is within the invention. Both the oral and nasal membranes offer advantages over other routes of administration. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many drugs. Further, the sublingual mucosa is convenient, acceptable and easily accessible.

The ability of molecules to permeate through the oral mucosa appears to be related to molecular size, lipid solubility and peptide protein ionization. Small molecules, less than 1000 daltons appear to cross mucosa rapidly. As molecular size increases, the permeability decreases rapidly. Lipid soluble compounds are more permeable than non-lipid soluble molecules. Maximum absorption occurs when molecules are un-ionized or neutral in electrical charges. Therefore charged molecules present the biggest challenges to absorption through the oral mucosae.

A pharmaceutical composition of iRNA may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Devices

For ease of exposition the devices, formulations, compositions and methods in this section are discussed largely with regard to unmodified iRNA agents. It should be understood, however, that these formulations, compositions and methods can be practiced with other oligonucleotides of the invention, e.g., modified iRNA agents, antisense, apatamer, antagomir and ribozyme, and such practice is within the invention. An iRNA agent, e.g., a double-stranded iRNA agent, or sRNA agent, (e.g., a precursor, e.g., a larger iRNA agent which can be processed into a sRNA agent, or a DNA which encodes an iRNA agent, e.g., a double-stranded iRNA agent, or sRNA agent, or precursor thereof) can be disposed on or in a device, e.g., a device which implanted or otherwise placed in a subject. Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to a iRNA, e.g., a device can release insulin.

Other devices include artificial joints, e.g., hip joints, and other orthopedic implants.

In one embodiment, unit doses or measured doses of a composition that includes iRNA are dispensed by an implanted device. The device can include a sensor that monitors a parameter within a subject. For example, the device can include pump, e.g., and, optionally, associated electronics.

Tissue, e.g., cells or organs, such as the kidney, can be treated with an iRNA agent ex vivo and then administered or implanted in a subject.

The tissue can be autologous, allogeneic, or xenogeneic tissue. For example, tissue (e.g., kidney) can be treated to reduce graft v. host disease. In other embodiments, the tissue is allogeneic and the tissue is treated to treat a disorder characterized by unwanted gene expression in that tissue, such as in the kidney. In another example, tissue containing hematopoietic cells, e.g., bone marrow hematopoietic cells, can be treated to inhibit unwanted cell proliferation.

Introduction of treated tissue, whether autologous or transplant, can be combined with other therapies.

In some implementations, the iRNA treated cells are insulated from other cells, e.g., by a semi-permeable porous barrier that prevents the cells from leaving the implant, but enables molecules from the body to reach the cells and molecules produced by the cells to enter the body. In one embodiment, the porous barrier is formed from alginate.

In one embodiment, a contraceptive device is coated with or contains an iRNA agent. Exemplary devices include condoms, diaphragms, IUD (implantable uterine devices, sponges, vaginal sheaths, and birth control devices. In one embodiment, the iRNA is chosen to inactive sperm or egg. In another embodiment, the iRNA is chosen to be complementary to a viral or pathogen RNA, e.g., an RNA of an STD. In some instances, the iRNA composition can include a spermicidal agent.

Formulations

The iRNA agents described herein can be formulated for administration to a subject. For ease of exposition the formulations, compositions and methods in this section are discussed largely with regard to unmodified iRNA agents. It should be understood, however, that these formulations, compositions and methods can be practiced with other oligonucleotides of the invention, e.g., modified iRNA agents, antisense, apatamer, antagomir and ribozyme, and such practice is within the invention.

A formulated iRNA composition can assume a variety of states. In some examples, the composition is at least partially crystalline, uniformly crystalline, and/or anhydrous (e.g., less than 80, 50, 30, 20, or 10% water). In another example, the iRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the iRNA composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An iRNA preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA preparation includes another iRNA agent, e.g., a second iRNA that can mediated RNAi with respect to a second gene, or with respect to the same gene. Still other preparation can include at least 3, 5, ten, twenty, fifty, or a hundred or more different iRNA species. Such iRNAs can mediated RNAi with respect to a similar number of different genes.

In one embodiment, the iRNA preparation includes at least a second therapeutic agent (e.g., an agent other than a RNA or a DNA). For example, an iRNA composition for the treatment of a viral disease, e.g. HIV, might include a known antiviral agent (e.g., a protease inhibitor or reverse transcriptase inhibitor). In another example, an iRNA composition for the treatment of a cancer might further comprise a chemotherapeutic agent.

Other formulations amenable to the present invention are described in U.S. provisional application Ser. No. 61/018, 616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Pharmaceutical Compositions

In one embodiment, the invention relates to a pharmaceutical composition containing an oligonucleotide of the invention e.g. an iRNA agent, as described in the preceding sections, and a pharmaceutically acceptable carrier, as described below. A pharmaceutical composition including the modified iRNA agent is useful for treating a disease caused by expression of a target gene. In this aspect of the invention, the iRNA agent of the invention is formulated as described below. The pharmaceutical composition is administered in a dosage sufficient to inhibit expression of the target gene.

The pharmaceutical compositions of the present invention are administered in dosages sufficient to inhibit the expression or activity of the target gene. Compositions containing the iRNA agent of the invention can be administered at surprisingly low dosages. A maximum dosage of 5 mg iRNA agent per kilogram body weight per day may be sufficient to inhibit or completely suppress the expression or activity of the target gene.

In general, a suitable dose of modified iRNA agent will be in the range of 0.001 to 500 milligrams per kilogram body weight of the recipient per day (e.g., about 1 microgram per kilogram to about 500 milligrams per kilogram, about 100 micrograms per kilogram to about 100 milligrams per kilogram, about 1 milligrams per kilogram to about 75 milligrams per kilogram, about 10 micrograms per kilogram to about 50 milligrams per kilogram, or about 1 microgram per kilogram to about 50 micrograms per kilogram). The pharmaceutical composition may be administered once per day, or the iRNA agent may be administered as two, three, four, five, six or more sub-doses at appropriate intervals throughout the day. In that case, the iRNA agent contained in each sub-dose must be correspondingly smaller in order to achieve the total daily dosage. The dosage unit can also be compounded for delivery over several days, e.g., using a conventional sustained release formulation which provides sustained release of the iRNA agent over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the infection or disease, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNA agent encompassed by the invention can be made using conventional methodologies or on the basis of in vivo testing using an appropriate animal model, as described elsewhere herein.

Advances in mouse genetics have generated a number of mouse models for the study of various human diseases. For example, mouse repositories can be found at The Jackson Laboratory, Charles River Laboratories, Taconic, Harlan, Mutant Mouse Regional Resource Centers (MMRRC) National Network and at the European Mouse Mutant Archive. Such models may be used for in vivo testing of iRNA agent, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), ocular, rectal, vaginal and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

For oral administration, the iRNA agent useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of iRNA agent in the cells that harbor the target gene or virus. Such substances include, for example, micellar structures, such as liposomes or capsids, as described below. Although microinjection, lipofection, viruses, viroids, capsids, capsoids, or other auxiliary agents are required to introduce iRNA agent into cell cultures, surprisingly these methods and agents are not necessary for uptake of iRNA agent in vivo. The iRNA agent of the present invention are particularly advantageous in that they do not require the use of an auxiliary agent to mediate uptake of the iRNA agent into the cell, many of which agents are toxic or associated with deleterious side effects. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions can also include encapsulated formulations to protect the iRNA agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

Toxicity and therapeutic efficacy of iRNA agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. iRNA agents that exhibit high therapeutic indices are preferred.

The data obtained from cell culture assays and animal studies can be used in formulating a range of dosage for use in humans. The dosages of compositions of the invention are preferably within a range of circulating concentrations that include the ED50 with little or no toxicity. The dosage may vary within this range depending upon the dosage form employed and the route of administration utilized. For any iRNA agent used in the method of the invention, the therapeutically effective dose can be estimated initially from cell culture assays. A dose may be formulated in animal models to achieve a circulating plasma concentration range of the iRNA agent or, when appropriate, of the polypeptide product of a target sequence (e.g., achieving a decreased concentration of the polypeptide) that includes the IC50 (i.e., the concentration of the test iRNA agent which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, iRNA agents relating to the invention can be administered in combination with other known agents effective in treating viral infections and diseases. In any event, the administering physician can adjust the amount and timing of iRNA agent administration on the basis of results observed using standard measures of efficacy known in the art or described herein.

Combination Therapy

In one aspect, composition of the invention can be used in combination therapy. The term "combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g, MET, RON, SEA, SEX); insulin receptor (e.g. IGFI-R); Eph (e.g. CEK5, CEK8, EBK, ECK, EEK, EHK-I, EHK-2, ELK, EPH, ERK, HEK, MDK2, MDK5, SEK); AxI (e.g. Mer/Nyk, Rse); RET; and platelet-derived growth factor receptor (PDGFR) (e.g. PDGFα-R, PDGFβ-R, CSFl-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43$^{abl}$, ARG); BTK (e.g. ITK/EMT, TEC); CSK, FAK, FPS, JAK, SRC, BMX, FER, CDK and SYK.

In another aspect of the invention, the subject compounds may be administered in combination with one or more agents that modulate non-kinase biological targets or processes. Such targets include histone deacetylases (HDAC), DNA methyltransferase (DNMT), heat shock proteins (e.g. HSP90), and proteosomes.

In one embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affmitak, Avastin, Herceptin, Erbitux, AG24322, PD325901, ZD6474, PD 184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplasties such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA). In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a respectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more adjunctive therapeutic agents. Examples of suitable agents for adjunctive therapy include steroids, such as corticosteroids (amcinonide, betamethasone, betamethasone dipropionate, betamethasone valerate, budesonide, clobetasol, clobetasol acetate, clobetasol butyrate, clobetasol 17-propionate, cortisone, deflazacort, desoximetasone, diflucortolone valerate, dexamethasone, dexamethasone sodium phosphate, desonide, furoate, fluocinonide, fluocinolone acetonide, halcinonide, hydrocortisone, hydrocortisone butyrate, hydrocortisone sodium succinate, hydrocortisone valerate, methyl prednisolone, mometasone, prednicarbate, prednisolone, triamcinolone, triamcinolone acetonide, and halobetasol proprionate); a 5HTi agonist, such as a triptan (e.g. sumatriptan or naratriptan); an adenosine Al agonist; an EP ligand; an NMDA modulator, such as a glycine antagonist; a sodium channel blocker (e.g. lamotrigine); a substance P antagonist (e.g. an NKi antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor c; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an H2-antagonist (e.g. ranitidine); a proton pump inhibitor (e.g. omeprazole); an antacid (e.g. aluminium or magnesium hydroxide); an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

Methods for Inhibiting Expression of a Target Gene

In yet another aspect, the invention relates to a method for inhibiting the expression of a target gene in a cell or organism. In one embodiment, the method includes administering the inventive oligonucleotide, e.g. antisense, aptamer, antagomir, or an iRNA agent; or a pharmaceutical composition containing the said oligonucleotide to a cell or an organism, such as a mammal, such that expression of the target gene is silenced. Compositions and methods for inhibiting the expression of a target gene using the inventive oligonucleotide, e.g. an iRNA agent, can be performed as described in the preceding sections.

In this embodiment, a pharmaceutical composition containing the inventive oligonucleotide may be administered by any means known in the art including, but not limited to oral or parenteral routes, including intravenous, intramuscular, intraperitoneal, subcutaneous, transdermal, airway (aerosol), ocular, rectal, vaginal, and topical (including buccal and sublingual) administration. In preferred embodiments, the pharmaceutical compositions are administered by intravenous or intraparenteral infusion or injection. The pharmaceutical compositions can also be administered intraparenchymally, intrathecally, and/or by stereotactic injection.

The methods for inhibiting the expression of a target gene can be applied to any gene one wishes to silence, thereby specifically inhibiting its expression, provided the cell or organism in which the target gene is expressed includes the cellular machinery which effects RNA interference. Examples of genes which can be targeted for silencing include, without limitation, developmental genes including but not limited to adhesion molecules, cyclin kinase inhibitors, Wnt family members, Pax family members, Winged helix family members, Hox family members, cytokines/lymphokines and their receptors, growth/differentiation factors and their receptors, and neurotransmitters and their receptors; (2) oncogenes including but not limited to ABLI, BCL1, BCL2, BCL6, CBFA2, CBL, CSFIR, ERBA, ERBB, EBRB2, ETS1, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES; (3) tumor suppresser genes including but not limited to APC, BRCA1, BRCA2, MADH4, MCC, NF1, NF2, RB1, TP53 and WT1; and (4) enzymes including but not limited to ACP desaturases and hydroxylases, ADP-glucose pyrophorylases, ATPases, alcohol dehydrogenases, amylases, amyloglucosidases, catalases, cellulases, cyclooxygenases, decarboxylases, dextrinases, DNA and RNA polymerases, galactosidases, glucanases, glucose oxidases, GTPases, helicases, hemicellulases, integrases, invertases, isomerases, kinases, lactases, lipases, lipoxygenases, lysozymes, pectinesterases, peroxidases, phosphatases, phospholipases, phosphorylases, polygalacturonases, proteinases and peptideases, pullanases, recombinases, reverse transcriptases, topoisomerases, and xylanases.

In addition to in vivo gene inhibition, the skilled artisan will appreciate that the inventive oligonucleotides, e.g. iRNA agent, of the present invention are useful in a wide variety of in vitro applications. Such in vitro applications, include, for example, scientific and commercial research (e.g., elucidation of physiological pathways, drug discovery and development), and medical and veterinary diagnostics. In general, the method involves the introduction of the oligonucleotide, e.g. an iRNA agent, into a cell using known techniques (e.g., absorption through cellular processes, or by auxiliary agents or devices, such as electroporation and lipofection), then maintaining the cell for a time sufficient to obtain degradation of an mRNA transcript of the target gene.

DEFINITIONS

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines, for example. Aliphatic groups as used herein may optionally include further substitutent groups.

The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_{20}$ indicates that the group may have from 1 to 20 (inclusive) carbon atoms in it. The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino. The term "mercapto" refers to an —SH radical. The term "thioalkoxy" refers to an —S-alkyl radical.

The term "cyclic" as used herein includes a cycloalkyl group and a heterocyclic group. Any suitable ring position of the cyclic group may be covalently linked to the defined chemical structure.

The term "acyclic" may describe any carrier that is branched or unbranched, and does not form a closed ring.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, decalin, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocycloalkyl" and "heterocyclic" can be used interchangeably and refer to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "silyl" as used herein is represented by the formula —$SiA^1A^2A^3$, where $A^1$, $A^2$, and $A^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

The Bases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-aminoadenine, 2-fluoroadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

The term "non-natural" nucleobase refers any one of the following: 2-methyladeninyl, N6-methyladeninyl, 2-methylthio-N6-methyladeninyl, N6-isopentenyladeninyl, 2-methylthio-N6-isopentenyladeninyl, N6-(cis-hydroxyisopentenyl)adeninyl, 2-methylthio-N6-(cis-hydroxyisopentenyl)adeninyl, N6-glycinylcarbamoyladeninyl, N6-threonylcarbamoyladeninyl, 2-methylthio-N6-threonyl carbamoyladeninyl, N6-methyl-N6-threonylcarbamoyladeninyl, N6-hydroxynorvalylcarbamoyladeninyl, 2-methylthio-N6-hydroxynorvalyl carbamoyladeninyl, N6,N6-dimethyladeninyl, 3-methylcytosinyl, 5-methylcytosinyl, 2-thiocytosinyl, 5-formylcytosinyl, N4-methylcytosinyl, 5-hydroxymethylcytosinyl, 1-methylguaninyl, N2-methylguaninyl, 7-methylguaninyl, N2,N2-dimethylguaninyl, N2,7-dimethylguaninyl, N2,N2,7-trimethylguaninyl, 1-methylguaninyl, 7-cyano-7-deazaguaninyl, 7-aminomethyl-7-deazaguaninyl, pseudouracilyl, dihydrouracilyl, 5-methyluracilyl, 1-methylpseudouracilyl, 2-thiouracilyl, 4-thiouracilyl, 2-thiothyminyl 5-methyl-2-thiouracilyl, 3-(3-amino-3-carboxypropyl)uracilyl, 5-hydroxyuracilyl, 5-methoxyuracilyl, uracilyl 5-oxyacetic acid, uracilyl 5-oxyacetic acid methyl ester, 5-(carboxyhydroxymethyl)uracilyl, 5-(carboxyhydroxymethyl)uracilyl methyl ester, 5-methoxycarbonylmethyluracilyl, 5-methoxycarbonylmethyl-2-thiouracilyl, 5-aminomethyl-2-thiouracilyl, 5-methylaminomethyluracilyl, 5-methylaminomethyl-2-thiouracilyl, 5-methylaminomethyl-2-selenouracilyl, 5-carbamoylmethyluracilyl, 5-carboxymethylaminomethyluracilyl, 5-carboxymethylaminomethyl-2-thiouracilyl, 3-methyluracilyl, 1-methyl-3-(3-amino-3-carboxypropyl)pseudouracilyl, 5-carboxymethyluracilyl, 5-methyldihydrouracilyl, 3-methylpseudouracilyl,

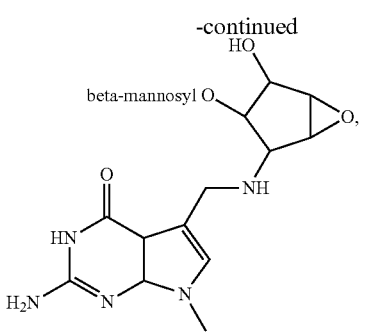

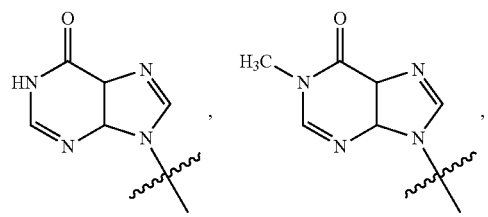

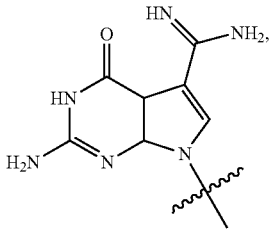

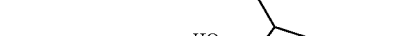

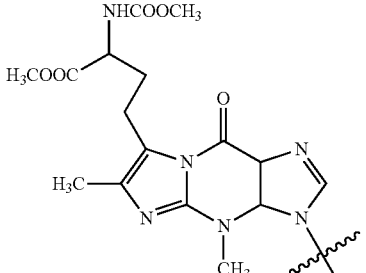

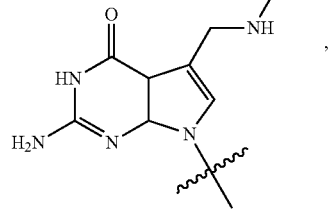

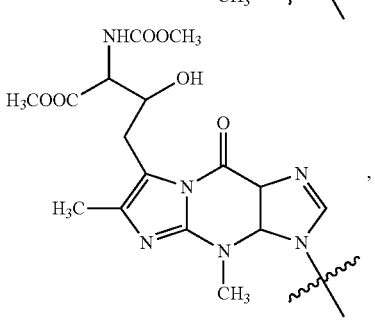

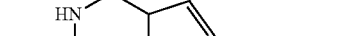

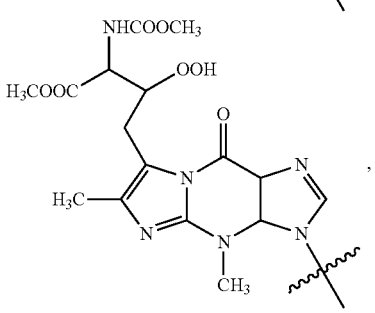

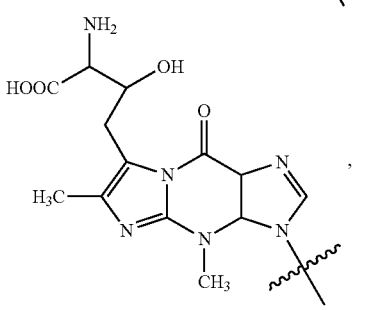

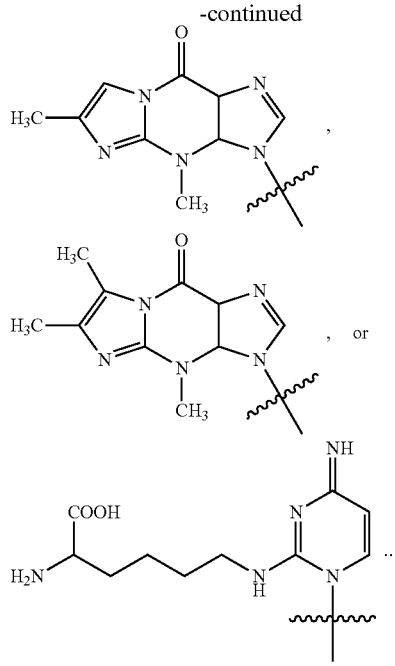

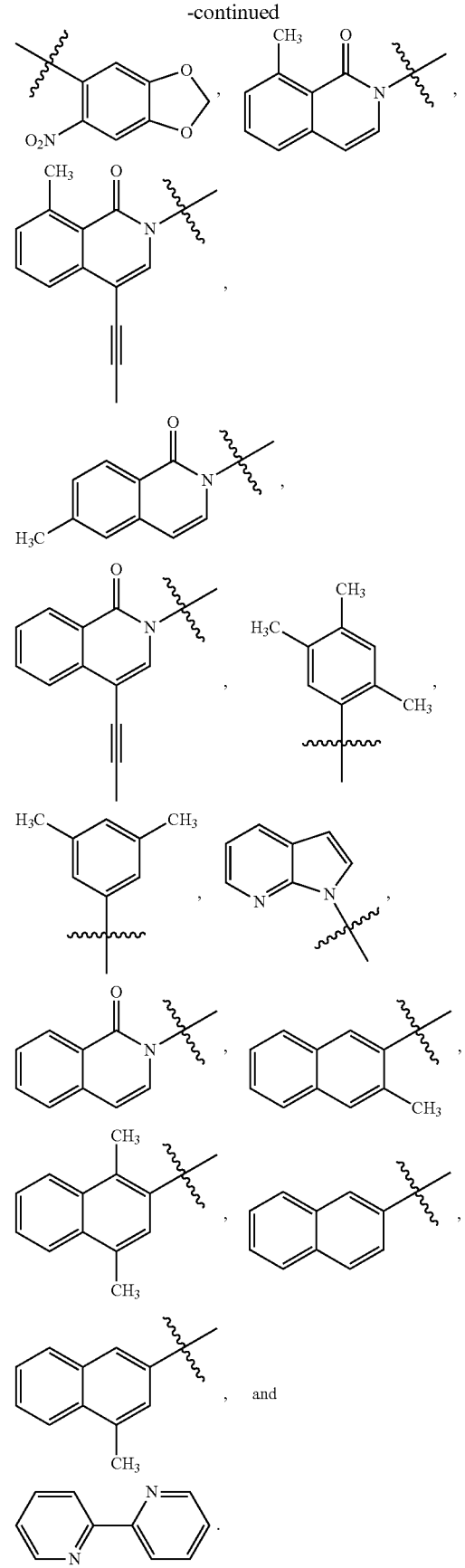

A universal base can form base pairs with each of the natural DNA/RNA bases, exhibiting relatively little discrimination between them. In general, the universal bases are non-hydrogen bonding, hydrophobic, aromatic moieties which can stabilize e.g., duplex RNA or RNA-like molecules, via stacking interactions. A universal base can also include hydrogen bonding substituents. As used herein, a "universal base" can include anthracenes, pyrenes or any one of the following:

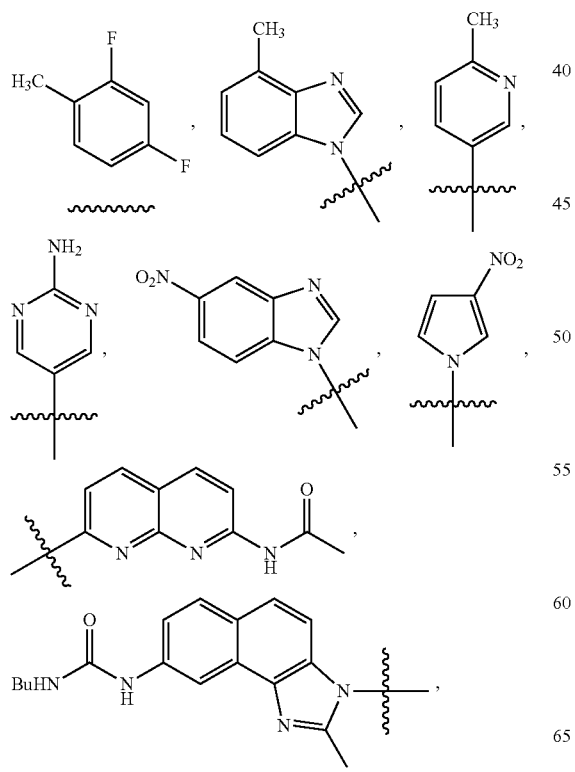

Antagomirs

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. Antagomirs may be used to efficiently silence endogenous miRNAs thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein, in its entirety.

Decoy Oligonucleotides

Because transcription factors can recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to upregulate genes that are suppressed by the binding of a transcription factor. Examples of the utilization of decoy oligonucleotides may be found in Mann et al., J. Clin. Invest., 2000, 106: 1071-1075, which is expressly incorporated by reference herein, in its entirety.

Antisense Oligonucleotides

Antisense oligonucleotides are single strands of DNA or RNA that are at least partially complementary to a chosen sequence. In the case of antisense RNA, they prevent translation of complementary RNA strands by binding to it. Antisense DNA can also be used to target a specific, complementary (coding or non-coding) RNA. If binding takes place, the DNA/RNA hybrid can be degraded by the enzyme RNase H. Examples of the utilization of antisense oligonucleotides may be found in Dias et al., Mol. Cancer Ther., 2002, 1: 347-355, which is expressly incorporated by reference herein, in its entirety.

Aptamers

Aptamers are nucleic acid molecules that bind a specific target molecule or molecules. Aptamers may be RNA or DNA based, and may include a riboswitch. A riboswitch is a part of an mRNA molecule that can directly bind a small target molecule, and whose binding of the target affects the gene's activity. Thus, an mRNA that contains a riboswitch is directly involved in regulating its own activity, depending on the presence or absence of its target molecule.

REFERENCES

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

EXAMPLES

The invention now being generally described, it will be more readily understood by reference to the following examples, which are included merely for purposes of illustration of certain aspects and embodiments of the invention, and are not intended to limit the invention. Thus, the invention should in way be construed as being limited to the following examples, but rather, should be construed to encompass any and all variations which become evident as a result of the teaching provided herein.

SYNTHETIC SCHEMES AND EXAMPLES

Alkyne derivatives for click chemistry (siRNA conjugation)

Example 1

Synthesis of Alkyne Derivative

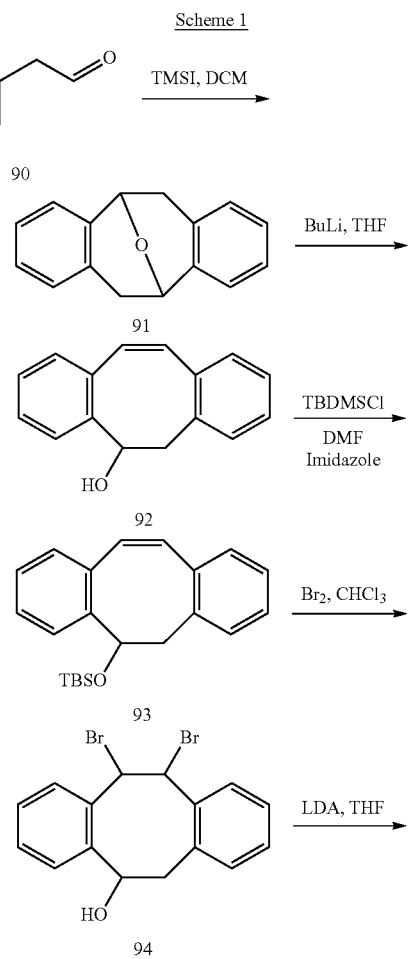

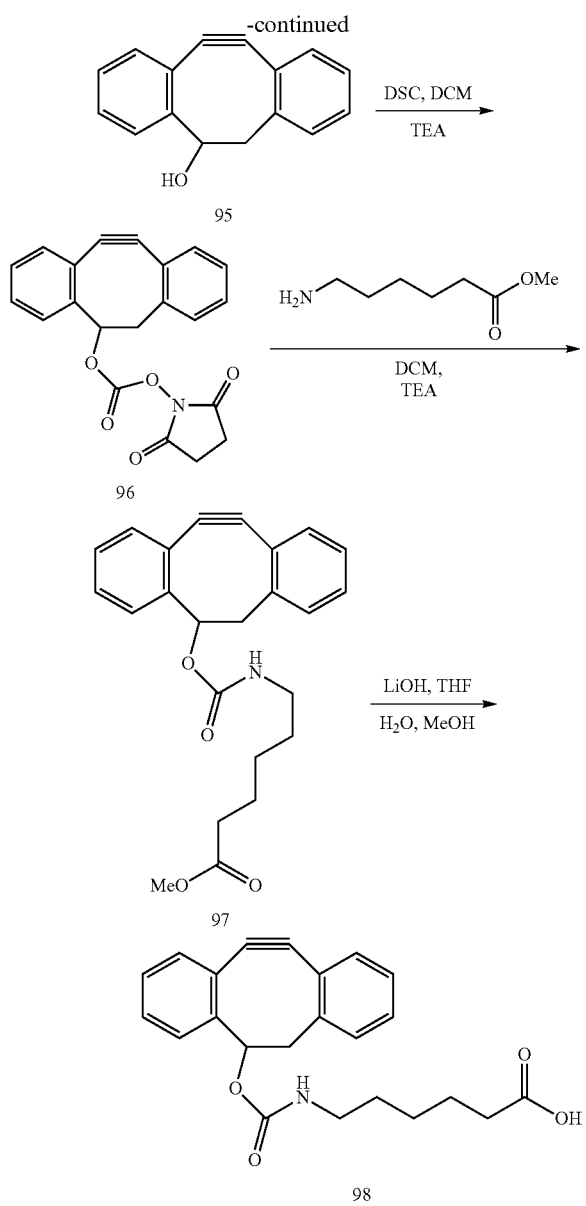

Synthesis of Compound 92:

Compound 91 (66 g, 0.29 mol) was dissolved in THF (600 mL) and cooled to 0-4° C. To the cooled solution was added n-butyl lithium (256 mL, 23% in hexane) drop wise maintaining temperature between 4-10° C. The reaction mass was allowed to reach RT and stirred for 2 hours. The reaction was quenched slowly with 5 ml of water first, later with excess water. The layers were separated and the aqueous layer was extracted with dichloromethane. The combined organic layer was washed with water, followed by brine and dried over sodium sulfate. The organic layer was evaporated at reduced pressure to obtain crude product, which was purified by silica gel chromatography using ethyl acetate/hexane as eluent to get the product as a white solid (43 g, 65%). $^1$H NMR (400 MHz, CDCl$_3$): δ 3.29-3.35 (m, 1H), 3.42-3.47 (m, 1H), 5.26-5.30 (m, 1H) 6.80-6.88 (m, 2H), 7.09-7.25 (m, 7H) and 7.36-7.46 (m, 1H). $^{13}$C NMR (100 MHz, CDCl$_3$): δ 42.52, 69.55, 74.27, 125.78, 126.82, 127.04, 127.28, 129.22, 129.81, 130.47, 131.40, 134.35, 136.12, 136.66 and 140.69. GC-MS: 222.

Synthesis of Compound 93:

To an ice-cooled solution of product 92 (43 g, 0.194 mol) in DMF (430 mL) under argon atmosphere was added imidazole (19.8 g, 0.29 mol) followed by ter-butyldimethylchlorosilane (43.7 g, 0.29 mol). The reaction mass was allowed to reach room temperature and stirred for one hour. The reaction mass was diluted with water (1 L) and extracted with ether. The organic layer was washed with water (700 ml), followed by brine, dried over sodium sulfate and finally evaporated at reduced pressure to obtain crude product, which was purified by silica gel chromatography using ether/hexane as eluent to get the product as yellow viscous liquid (45 g, 70%) $^1$H NMR (400 MHz, CDCl$_3$): δ 0.063 (s, 3H), 0.081 (s, 3H), 0.95 (s, 9H), 3.20-3.24 (m, 1H), 3.50-3.56 (m, 1H), 5.48-5.52 (m, 1H) 6.80-6.88 (m, 2H), 7.09-7.25 (m, 7H) and 7.36-7.46 (m, 1H).

Synthesis of Compound 94:

To an ice-cooled solution of compound 93 (38 g, 0.113 mol) in chloroform (380 mL) was added bromine (21.70 g, 0.135 mol) in chloroform drop wise over a period of 40 minutes at 0-4° C. The reaction was quenched, just after the addition, with saturated sodium thiosulfate and separated the layers. The aqueous layer was extracted with chloroform (1×500 ml). The combined organic layer was washed once with sodium thiosulfate (1×300 ml), followed by water (1×300 ml), dried over sodium sulfate and finally evaporated at reduced pressure to obtain the crude product, which was purified by silica chromatography using ether/hexane as eluent to get the product as pale brown liquid (20.7 g, 48%). $^1$H NMR (400 MHz, CDCl$_3$): δ 2.81-3.10 (m, 1H), 3.55-3.75 (m, 1H), 5.27-5.8 (m, 3H) and 6.86-7.58 (m, 8H).

Synthesis of Compound 95:

To a solution of compound 94 (110 g, 0.28 mol) in THF (3.3 L), was added freshly prepared LDA (92.4 g, 0.86 mol) in THF at room temperature and allowed to stir for half an hour. The reaction was quenched with water and separated the layers. The aqueous layer was extracted with dichloromethane. The combined organic layer was dried over sodium sulfate and evaporated at reduced pressure. The crude product obtained was purified by silica gel chromatography using ethyl acetate/hexane as eluent to get the product as a white solid (50 g, 79%). $^1$H NMR (400 MHz, CDCl$_3$): δ 2.90-3.12 (m, 2H), 4.6 (s, 1H) and 7.29-7.75 (m, 8H).

Synthesis of 97:

To an ice-cooled solution of compound 95 (50 g, 0.22 mol) in dichloromethane (500 mL) was added N,N'-disuc- Synthesis of Compound 91:

To an ice-cooled solution of phenyl acetaldehyde (200 g, 1.662 mol) in dichloromethane (1 L) was added iodotrimethylsilane (475 mL, 3.325 mol) drop-wise. The reaction mass was allowed to reach room temperature and stirred for 16 hours. The reaction was quenched with 1M sodium thiosulfate solution. The layers were separated. The aqueous layer was extracted with dichloromethane (1×500 ml). Combined organic layer was washed with saturated sodium bicarbonate (3×1 L), followed by brine wash. The organic layer was dried and evaporated at reduced pressure to obtain crude product, which was purified by silica gel chromatography using ether/hexane as eluent to get the product (70.23 g, 38%) as a brown solid. $^1$H NMR (400 MHz, CDCl$_3$): δ 2.75-2.79 (d, 2H, J=16 Hz), 3.52-3.58 (dd, 2H, J=6 Hz), 5.30-5.29 (d, 2H, J=6 Hz) and 6.96-7.50 (m, 8H). $^{13}$C NMR (100 MHz, CDCl$_3$): δ 36.11, 69.55, 76.68, 77.00, 77.32, 125.14, 125.95, 126.81, 128.35, 129.07, 131.59 and 137.78. GC-MS: 222 cinimidyl carbonate (116 g, 0.45 mol), followed by triethyl amine (64.4 mL, 0.46 mol) and allowed to reach room temperature under argon atmosphere. The reaction mass was allowed to stir for 14 hours at room temperature. Diluted with dichloromethane and washed with water and brine. Dried over sodium sulfate and removed the solvent. The crude obtained was taken as such to the next stage without isolating the product (82 g). To an ice-cooled solution of DSC derivative in dichloromethane (900 mL) was added methyl 6-aminocaproate (65 g, 0.45 mol) in dichloromethane, followed by triethylamine (65 mL, 0.45 mol) and allowed to reach room temperature. The solvents were evaporated to dryness at reduced pressure to get crude product, which was purified by silica gel chromatography using methanol/dichloromethane as eluent to get the product as a pale yellow liquid (67.3 g, 60%). $^1$H NMR (400 MHz, CDCl$_3$): δ 1.37-1.41 (m, 2H), 1.64-1.67 (m, 2H), 2.30-2.34 (t, 2H, J=18 Hz), 2.87-2.92 (m, 2H), 3.13-3.21 (m, 4H), 3.67 (s, 3H), 4.97 (m, 1H), 5.4 (s, 1H) and 7.26-7.49 (m, 8H).

Synthesis of 98:

To a solution of compound 97 (45 g, 0.11 mol) in methanol and THF was added lithium hydroxide (10.5 g, 0.23 mol) in water at room temperature (480 mL, water: THF:MeOH 2:1:1). The reaction mass was allowed to stir for half an hour. The solvents were evaporated at reduced pressure. The residue obtained was diluted with water and washed with ethyl acetate (3×250 ml) to remove impurities. The aqueous layer then was acidified with 10% hydrochloric acid and extracted with ethyl acetate. The organic layer was dried over sodium sulfate and evaporated at reduced pressure to afford pure product as pale brown solid (43 g, 99%). $^1$H NMR (400 MHz, DMSO-d$_6$): δ 1.24-1.32 (m, 2H), 1.39-1.54 (m, 4H), 2.18-2.22 (t, 2H, J=16 Hz), 2.75-2.79 (dd, 1H, J=9 Hz), 2.96-3.01 (m, 2H), 3.16-3.20 (d, 2H, J=16 Hz), 5.3 (s, 1H) and 7.3-7.6 (m, 8H). $^{13}$C NMR (100 MHz, DMSO-d$_6$): δ 24.10, 25.70, 28.96, 33.52, 40.07, 45.47, 75.16, 109.84, 112.51, 120.29, 122.84, 123.71, 125.68, 126.00, 127.20, 127.25, 128.31, 130.02, 150.81, 152.50, 155.14, 171.87, and 174.30. LC-MS: 376 (M−1)$^+$.

Example 2

Copper Free Click Chemistry with Azido Derivatives

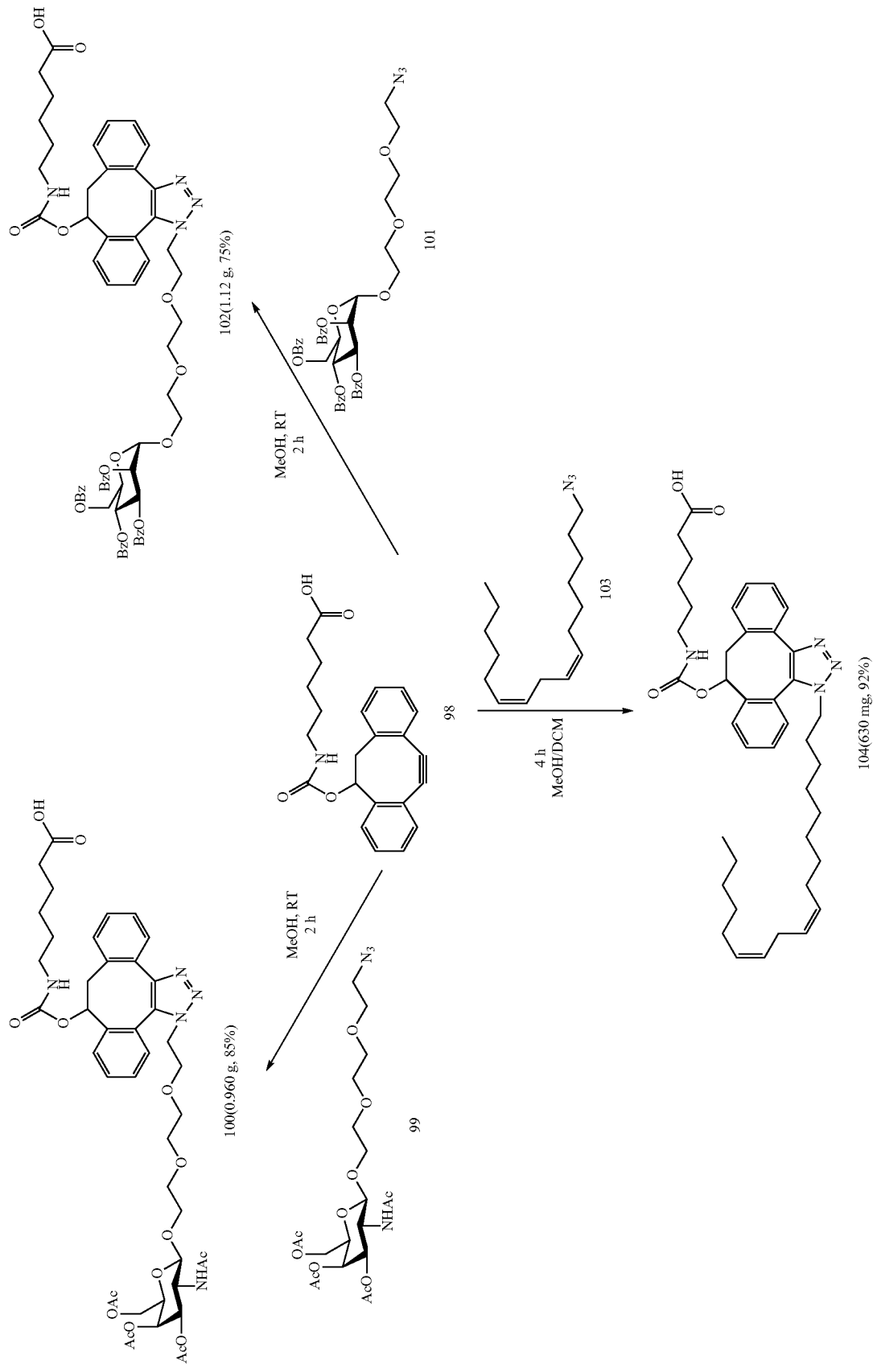

Synthesis of 100:

Compound 98 (0.500 g, 1.32 mmol) and the GalNAc azide 99 (0.668 g, 1.32 mmol) were taken in MeOH (15 mL) and stirred the reaction mixture under argon. Reaction was monitored by TLC, in 2 hrs reaction was complete. Solvent was removed the residue was purified by chromatography (2-5% MeOH/DCM) to get the product as a color less liquid (0.960 g, 85%). 1HNMR (DMSO-d6) d=MS calculated for $C_{43}H_{55}N_5O_{15}$ 881.37. Found 904.36 (M+Na).

Synthesis of 102:

Compound 98 (0.500 g, 1.32 mmol) and the mannose azide 101 (0.994 g, 1.32 mmol) were taken in MeOH (15 mL) and stirred the reaction mixture under argon. Reaction was monitored by TLC, in 3 hrs reaction was complete. Solvent was removed the residue was purified by chromatography (20-60% EtOAc/Hexane) to get the product as a color less liquid (1.12 g, 75%). 1HNMR (DMSO-d6) d=MS calculated for $C_{63}H_{62}N_4O_{16}$ 1130.42. Found 1153.40 (M+Na).

Synthesis of 103:

Compound 98 (0.300 g, 1.015 mmol) and the Linolel azide 103 (0.383 g, 1.015 mmol) were taken in MeOH/DCM (20 mL, 2:1) mixture and stirred the reaction mixture under argon. Reaction was monitored by TLC; in 4 hrs reaction was complete. Solvent was removed the residue was purified by chromatography (30-60% EtOAc/Hexane) to get the product as a color less liquid (0.630 g, 92%). 1HNMR (DMSO-d6) d=MS calculated for $C_{41}H_{56}N_4O_4$ Found: 668.43. Found 669.43 (M+H).

Example 3

Synthesis of Solid Support and Amidite

Scheme 3

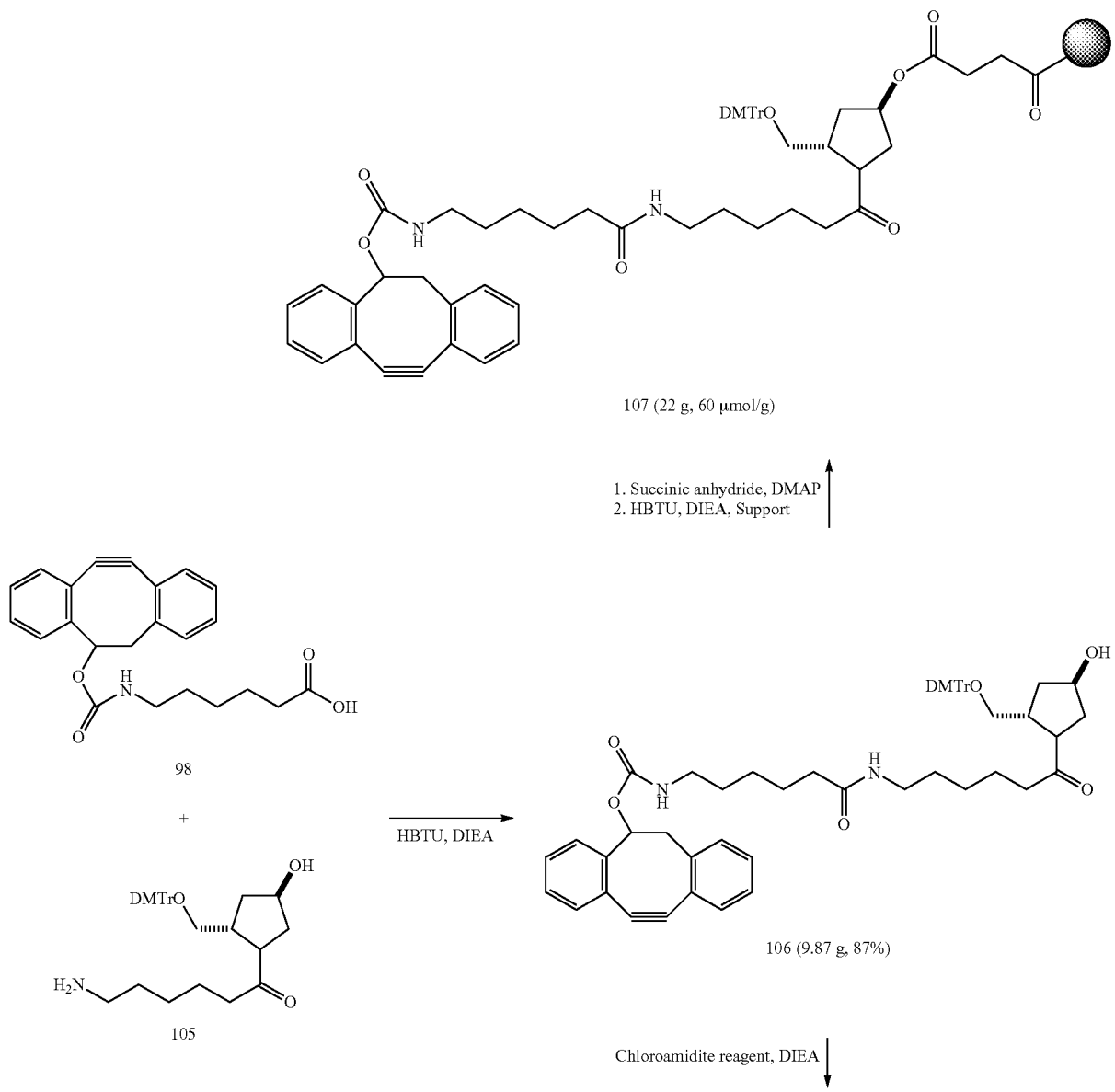

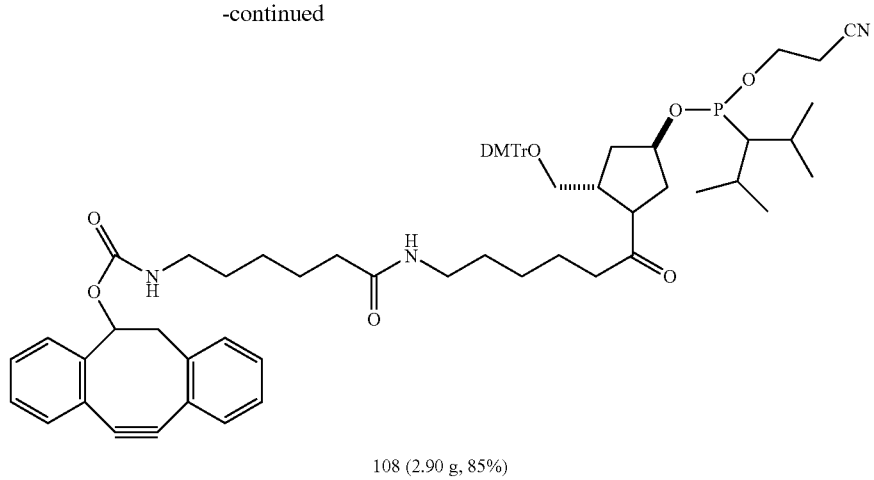

108 (2.90 g, 85%)

Synthesis of Compound 106:

To a stirred solution of compound 98 (5.00 g, 13.24 mmol), 105 (8.45 g, 15.88 mmol) and DIEA (6.90 mL, 3 eq) in DMF (100 mL); HBTU (6.41 g, 1.3 eq) was added and stirred the solution overnight at room temperature. The mixture was poured in to an ice water mixture as extracted with Ethyl acetate. Dried over sodium sulfate and the crude product were purified by chromatography (3-5% MeOH/DCM) to get the product as pale yellow solid (9.87 g, 87%). MS calculated for $C_{55}H_{61}N_3O_8$ 891.45. Found 892.40.

Synthesis of Compound 107:

Compound 106 (2.04 g, 2.280 mmol) was dissolved in DCM (20 mL) to that succinic anhydride (0.459 g, 2 eq.) and DMAP (0.850 g, 3 eq.) were added and stirred the reaction mixture overnight. Solvents were removed and the residue filtered through a small pad of silica gel. Crude product was used for the next reaction. The above compound dissolved in DMF (100 mL) to that HBTU (1.29 g, 1.5 eq) and DIEA (1.19 mL, 3 eq.) were added swirl for few minutes. Solid supports (Alkyl amino CPG, 22 g) was added and shake the mixture for 4 hrs. Filtered, washed with DCM, DCM/MeOH and anhydrous ether. Solid support was capped with acetic anhydride and pyridine. Repeated the same washing process and dried the support under vacuum (23.5 g, 59.50 mol/g).

Synthesis of Compound 108:

Compound 106 (3.00 g, 3.36 mmol) was dissolved in DCM (30 mL) to that DIEA (1.16 mL, 2 eq.) and Chloroamidite reagent were added and stirred the mixture for 30 minutes at room temperature. Reaction was monitored by TLC, reaction mixture was transferred to a separatory funnel washed with water and sodium bicarbonate solution. Crude product was purified by chromatography (EtOAc/Hexane) to get the compound as white fluffy solid (2.93 g, 79%).

Example 4

Synthesis of Single-Stranded RNA Containing Active Alkyne by Solid Phase Method

RNA oligonucleotides containing 3', internal, and 5' alknye (Table 1-4) were synthesized on a DNA synthesizer ABI 394 using standard phosphoramidite chemistry with commercially available 5'-O-(4,4'-dimethoxytrityl)-3'-O-(2-cyanoethyl-N,N-diisopropyl) phosphoramidite monomers of uridine (U), 4-N-benzoylcytidine ($C^{Bz}$), 6-N-benzoyladenosine ($A^{Bz}$) and 2-Nisobutyrylguanosine ($G^{iBu}$) with 2'-O-t-butyldimethylsilyl protected phosphoramidites, and 5'-O-(4,4'-dimethoxytrityl)-2'-deoxythymidine-3'-O-(2-cyanoethyl-N,N-diisopropyl) phosphoramidite (T). Alkyne phosphoramidte (Q99) and alkyne-CPG (L146) used in this study are shown in Table 1 and Table 2. After cleavage and de-protection of part of RNA products, RNA oligonucleotides were purified by reverse phase high-performance liquid chromatography (RP-HPLC) and characterized by LC-MS.

Example 5

Figure 1:
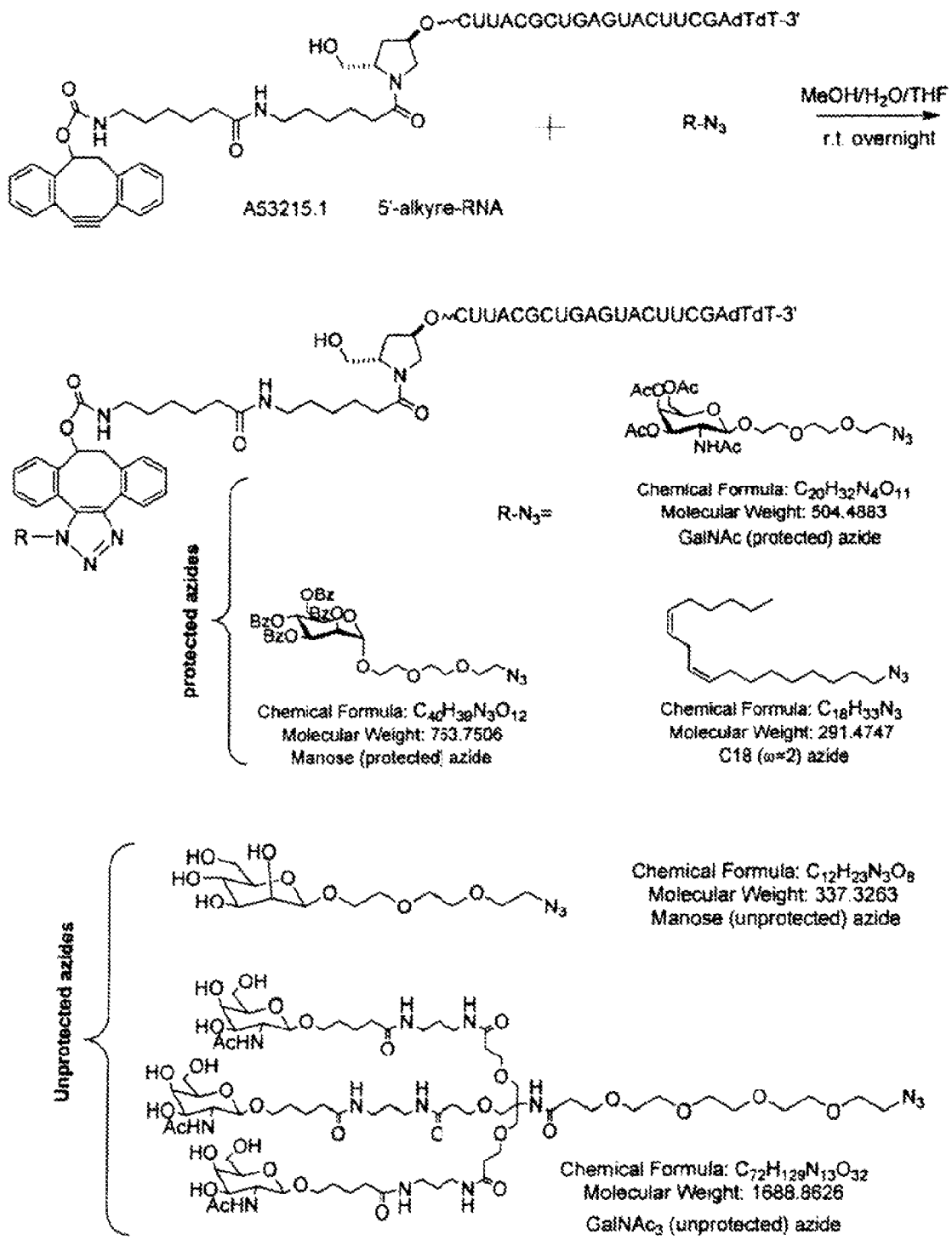
FIG. 1 depicts the click 5'-alkyne-RNA (A53215.1) with different azides (protected and unprotected) in solution phase.

Cu(I)-Free Click Reactions of 5'-alkyne-RNA (A53215.1) with GalNAc (Protected), Mannose (Protected) and C18 Azides in Solution Phase (FIG. 1)

Figure 2:
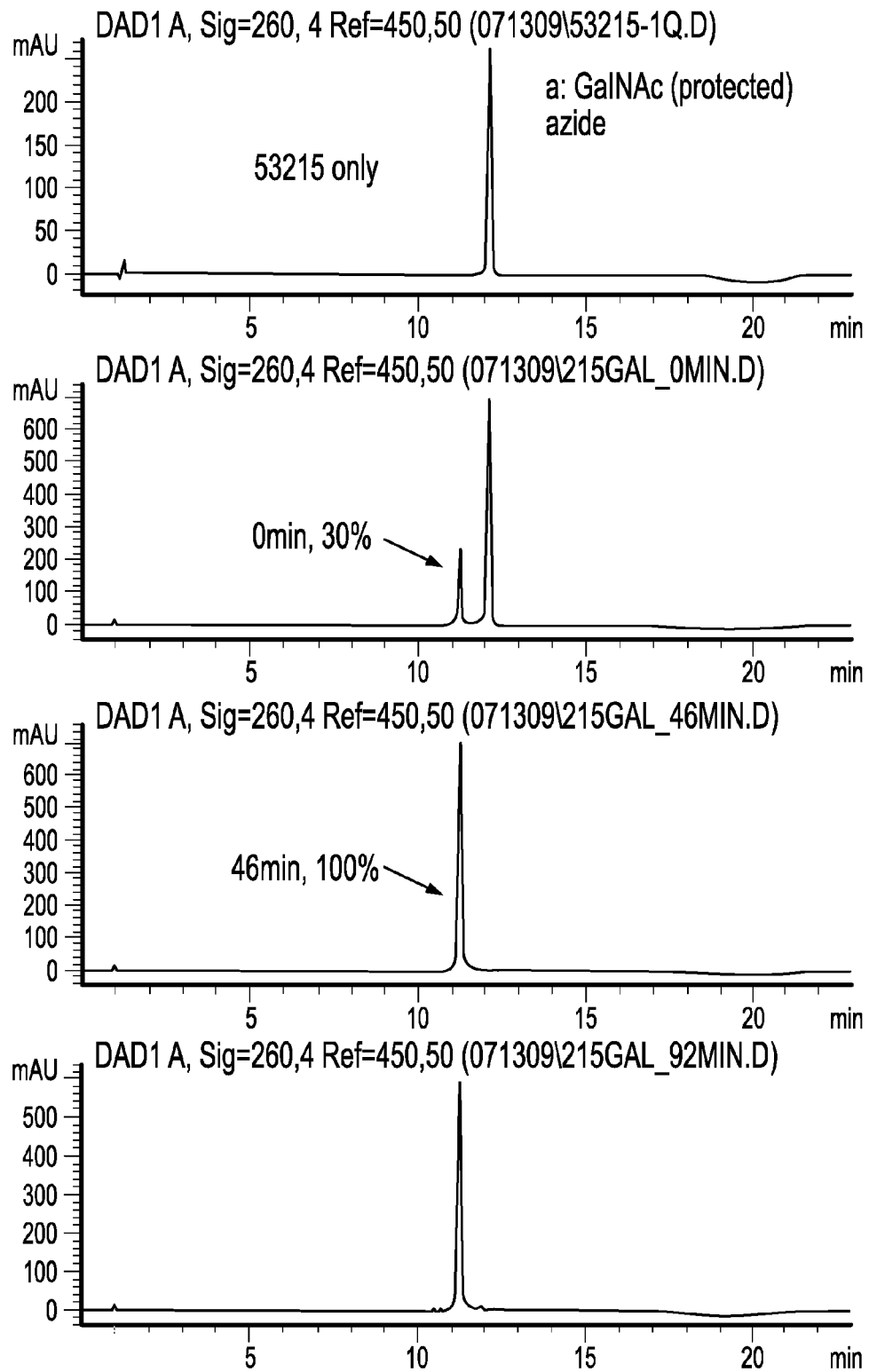
FIG. 2 depicts the monitoring of reaction progress by HPLC analysis: click 5'-alkyne-RNA (A53215.1) with (a) GalNAc (protected) azide, (b) mannose (protected) azide; (c) C18 azide1 in solution phase; and (d) time-course product percentage of click reactions.
Figure 2:
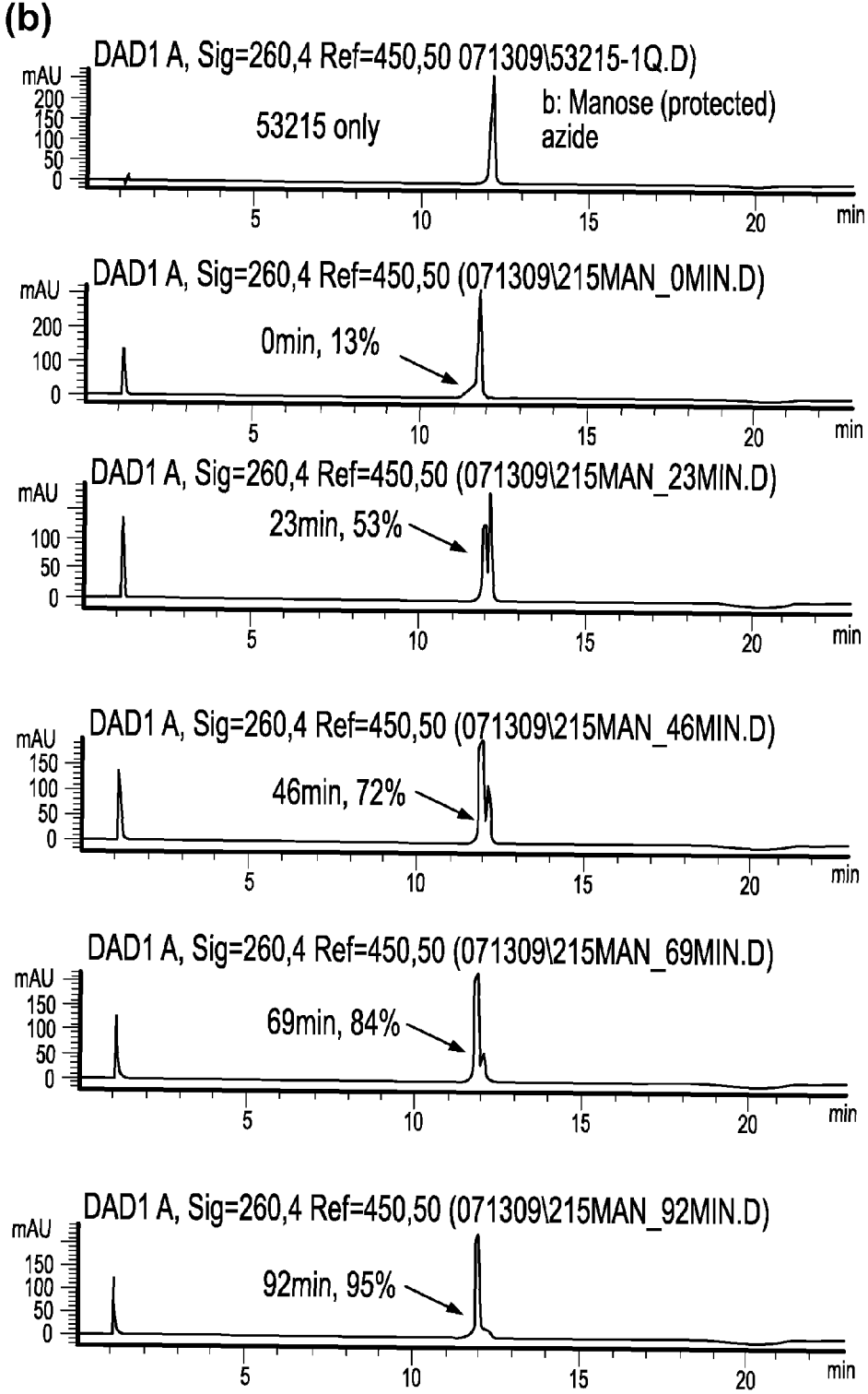
Figure 2:
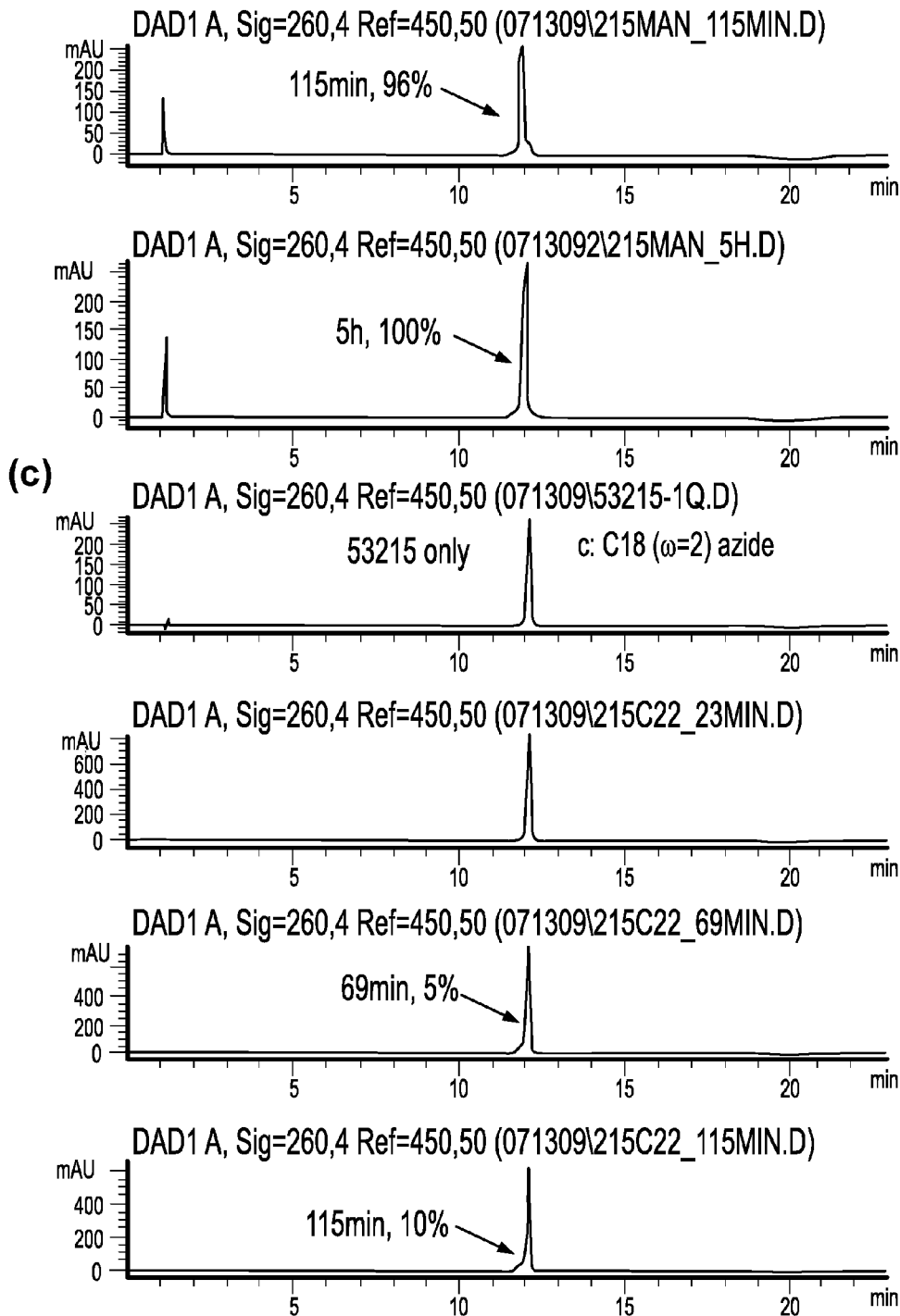
Figure 2:
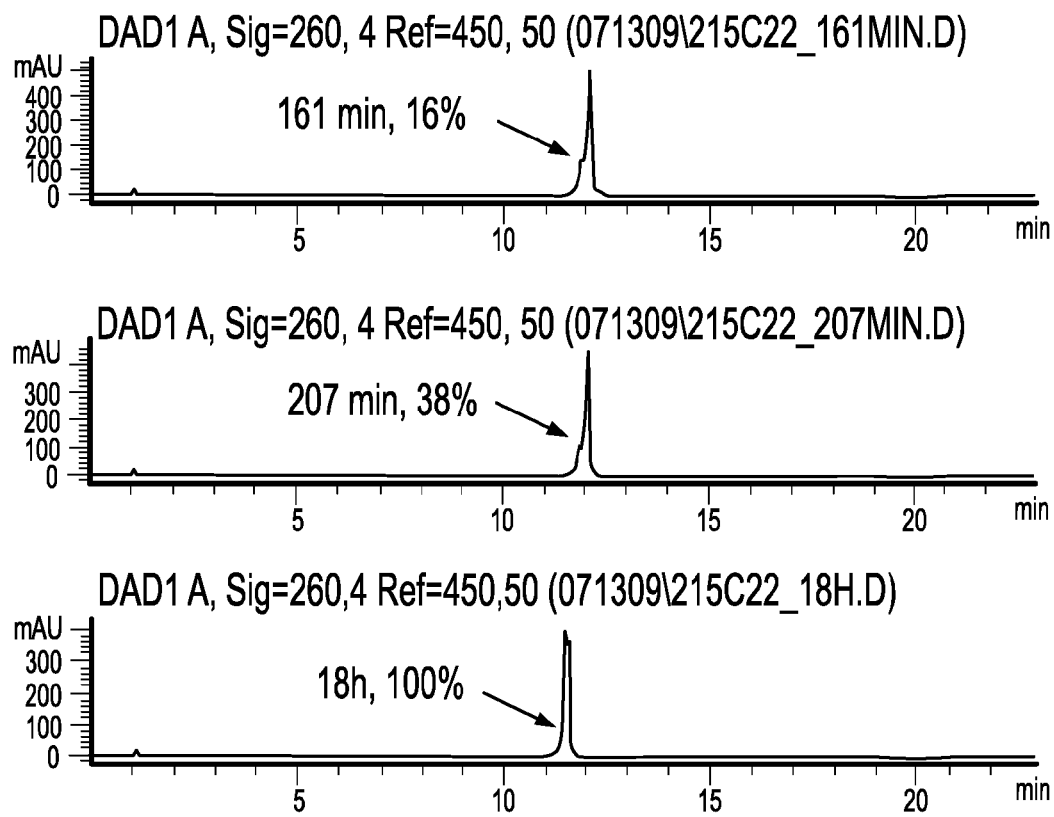
Figure 2:
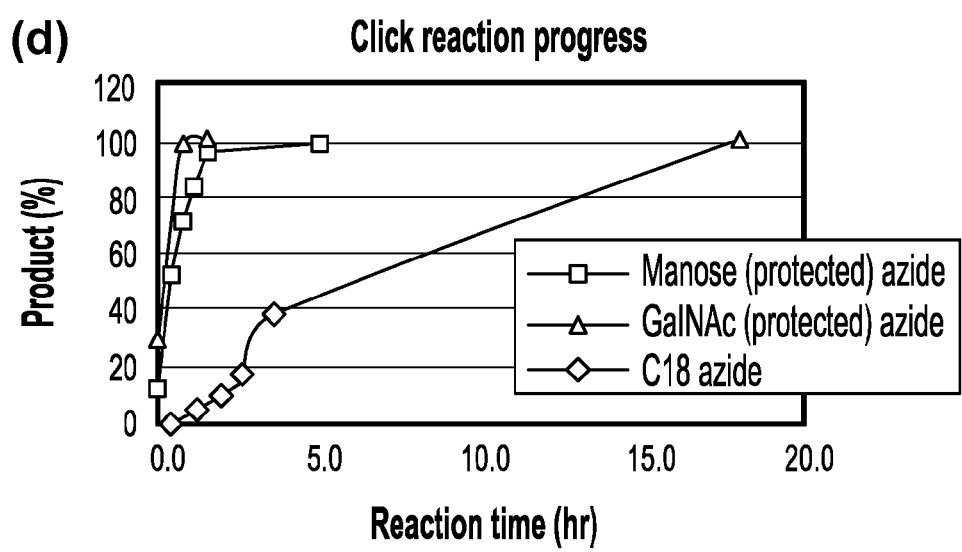

To 5'-alkyne-RNA (A53215.1) (0.05 µmol, 89 µL RNA from 0.56 mM stock solution in water) was added an azide (FIG. 1) (20 equiv by alkyne, 1 µmol, 20 µL azide of a 50 mM solution in methanol for GalNAc (protected) azide and mannose (protected) azide, THF for C18 azide. MeOH was added to obtain a total volume of 200 µL for click reactions with GalNAc (protected) azide. For mannose (protected) azide, MeOH/THF (1:1 v/v) was added to obtain a clear solution of 300 µL. For click reaction with C18 azide, MeOH/THF (1:1 v/v) was added to obtain a clear solution of 200 µL. After mixing, the click reaction was immediately monitored at room temperature by analytical RP-HPLC by directly injecting 1 µL reaction mixture into an Agilent HPLC with DNAPAC™ PA-200 column (4×250 mm) and a gradient of 8-20% buffer B in 16 min at a flowrate of 1 mL/min. Buffer A contains 20 mM Tris HCl pH 8.0, 10 mM $NaClO_4$, 1 mM EDTA and 50% ACN. Buffer B contains 20 mM Tris HCl, pH 8.0, 800 mM $NaClO_4$, 1 mM EDTA and 50% ACN. The HPLC analysis is shown in FIG. 2.

It is shown that click reaction of 5'-alkyne-RNA (A53215.1) with GalNAc (protected) azide is very fast. After one hour, the reaction is completed (FIG. 2a&d). The click reaction of 5'-alkyne-RNA (A53215.1) with mannose (protected) azide is a little slower, but after five hour, the reaction is completed (FIG. 2b&d). The click reaction of 5'-alkyne-RNA (A53215.1) with C18 azide is the slowest. After one hour, there is no reaction detected by RP-HPLC. After 3 hours, there is only 38% product generated. After 20 hours, the reaction is completed (FIG. 2c&d). All click products were confirmed with right molecular weight by LC/MS analysis (Table 1).

Example 6

Cu(I)-Free Click Reactions of 5'-alkyne-RNA (A53215.1) with GalNAc3 (Unprotected) and Mannose (Unprotected) in Solution Phase (FIG. 1)

Figure 3:
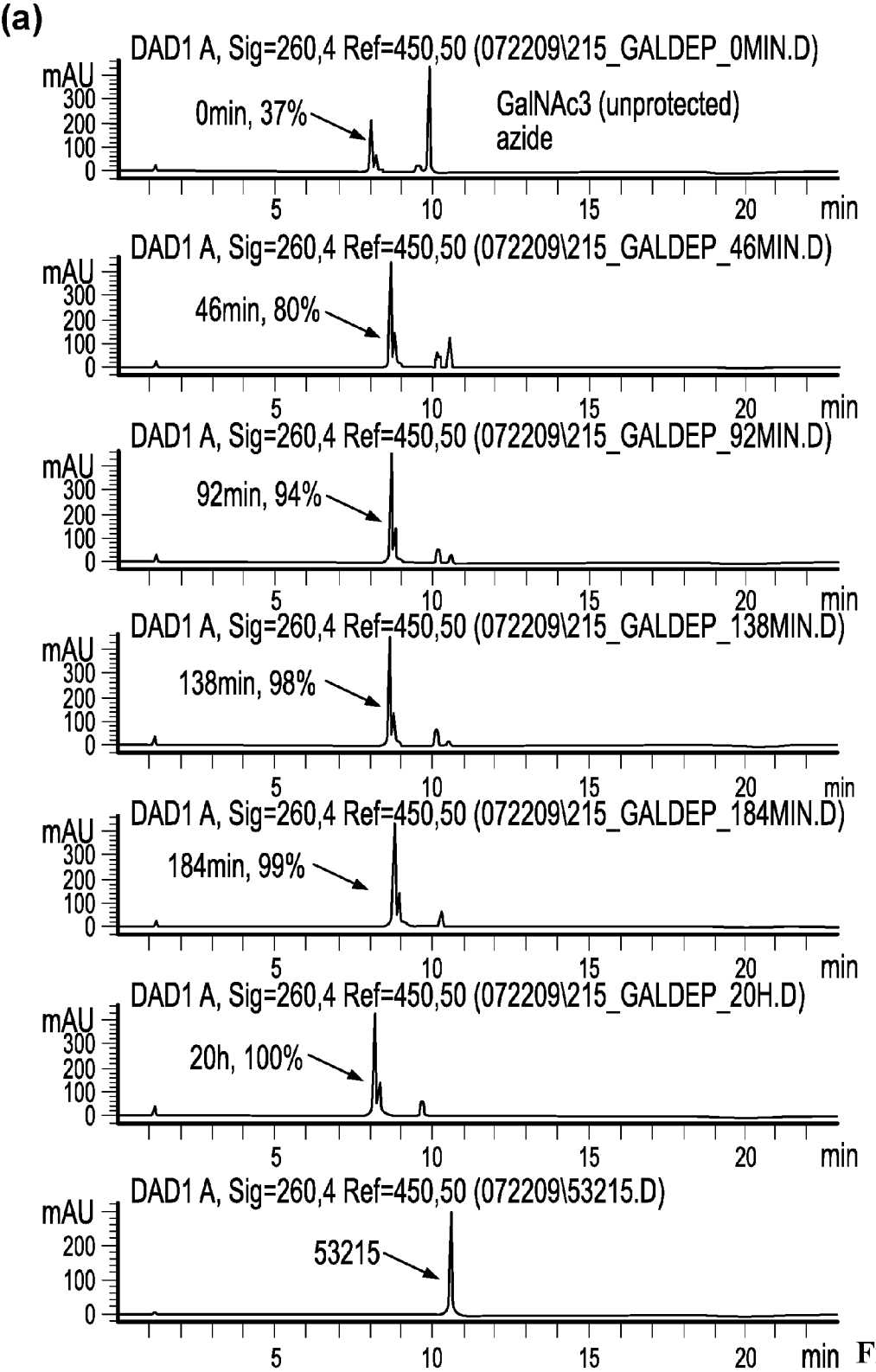
FIG. 3 depicts the monitoring of reaction progress by HPLC analysis: click 5'-alkyne-RNA (A53215.1) with (a) GalNAc3 (unprotected) azide; (b) mannose (unprotected) azide in solution phase; and (c) time-course product percentage of click reactions.
Figure 3:
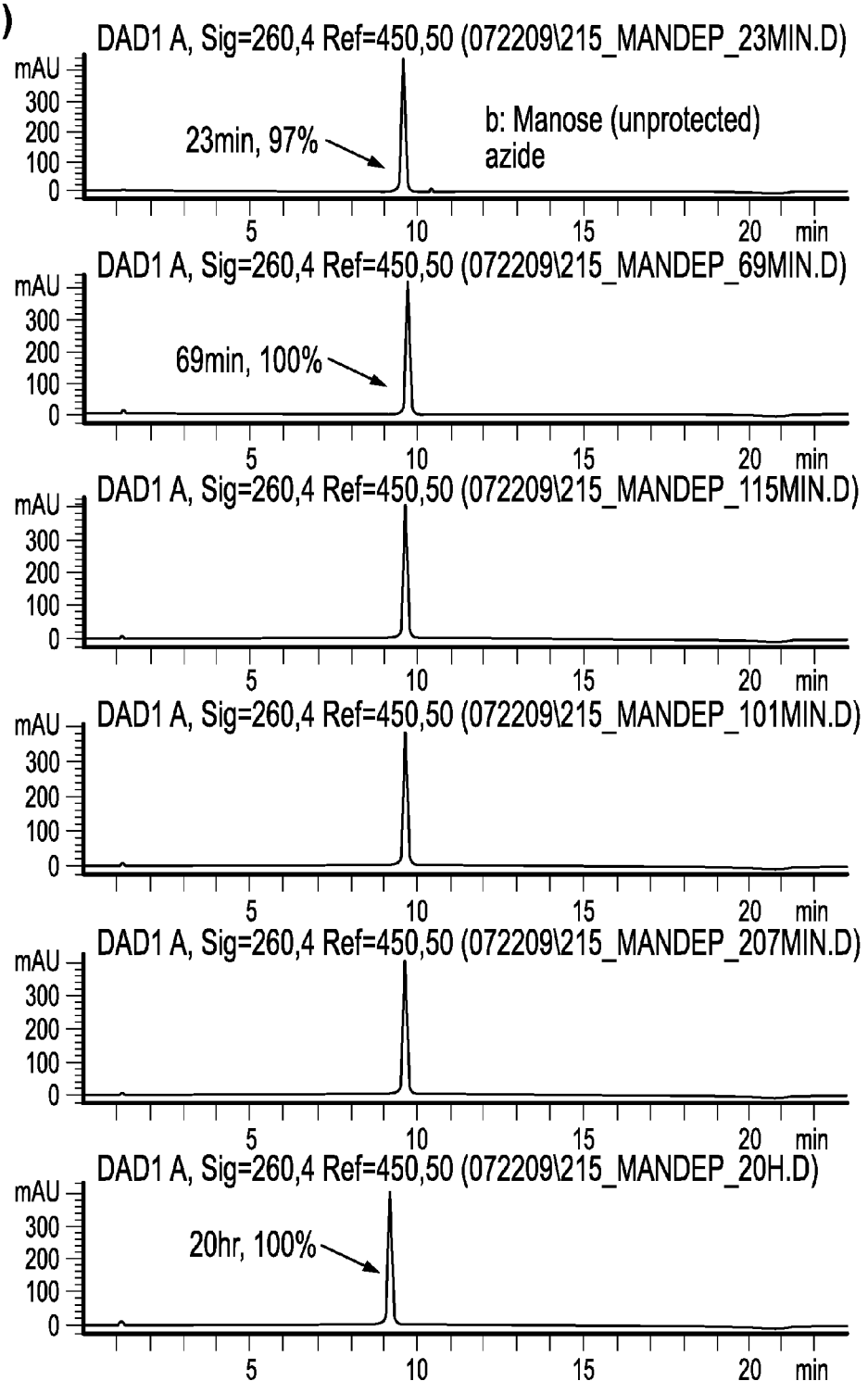
Figure 3:
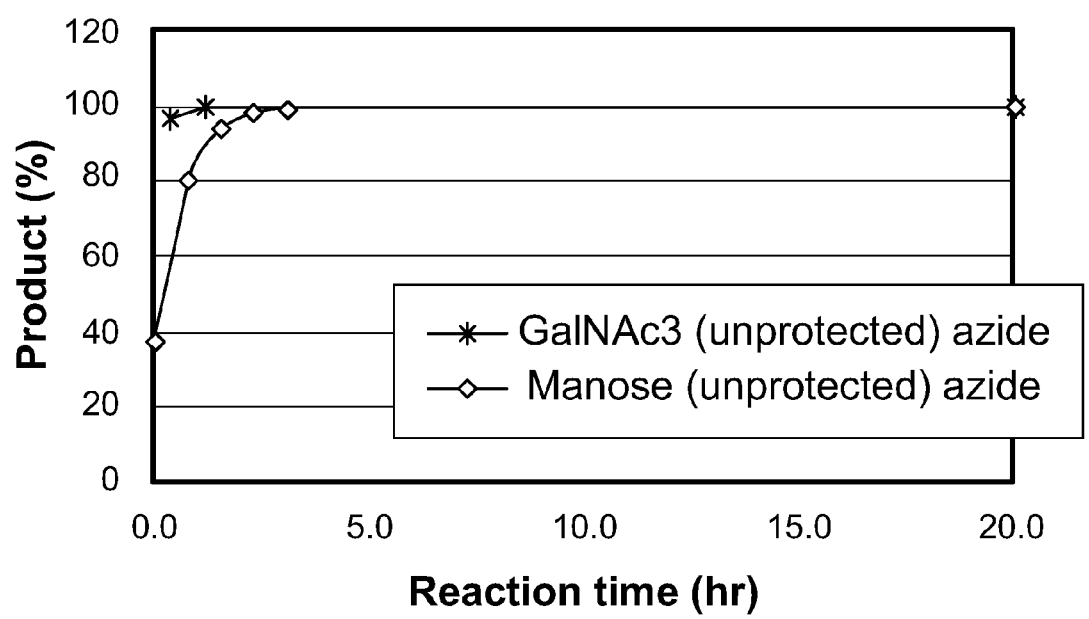

To 5'-alkyne-RNA (A53215.1) (0.05 µmol, 89 µL RNA from 0.56 mM stock solution in water) was added an azide (FIG. 1) (20 equiv by alkyne, 1 µmol, 20 µL azide of a 50 mM solution in methanol for GalNAc3 (unprotected) azide and mannose (unprotected) azide. MeOH was added to obtain a total volume of 200 µL. After mixing, the click reaction was immediately monitored at room temperature by analytical RP-HPLC by directly injecting 1 µL reaction mixture into an Agilent HPLC with DNAPAC™ PA-200 column (4×250 mm) and a gradient of 8-20% buffer B in 16 min at a flowrate of 1 mL/min. Buffer A contains 20 mM Tris HCl pH 8.0, 10 mM NaClO$_4$, 1 mM EDTA and 50% ACN. Buffer B contains 20 mM Tris HCl, pH 8.0, 800 mM NaClO$_4$, 1 mM EDTA and 50% ACN. The HPLC analysis is shown in FIG. 3.

It is shown that click reaction of 5'-alkyne-RNA (A53215.1) with GalNAc3 (unprotected) azide is moderately fast. After one hour, the reaction is more than 80% completed (FIG. 3a&c). After 3 hours, the reaction was almost 100% completed. The click reaction of 5'-alkyne-RNA (A53215.1) with mannose (protected) azide is very fast in this study. After one hour, the reaction is completed (FIG. 3b&c). All click products were confirmed with right molecular weight by LC/MS analysis (Table 1). The impurity peak observed in the click reaction of 5'-alkyne-RNA (A53215.1) with GalNAc3 (unprotected) azide is expected from azide monomer. The major impurity has a mass of 8742.01 (−203 compared with the product mass 8945.57) (data not shown).

Example 7

Figure 4:
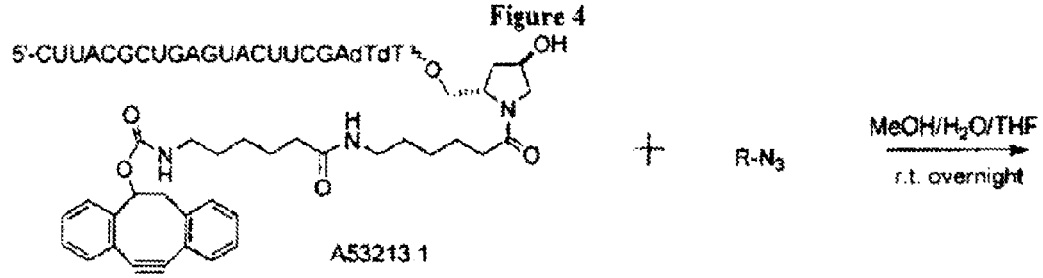
FIG. 4 depicts the click 3'-alkyne-RNA (A53213.1) with different protected azides in solution phase.
Figure 4:
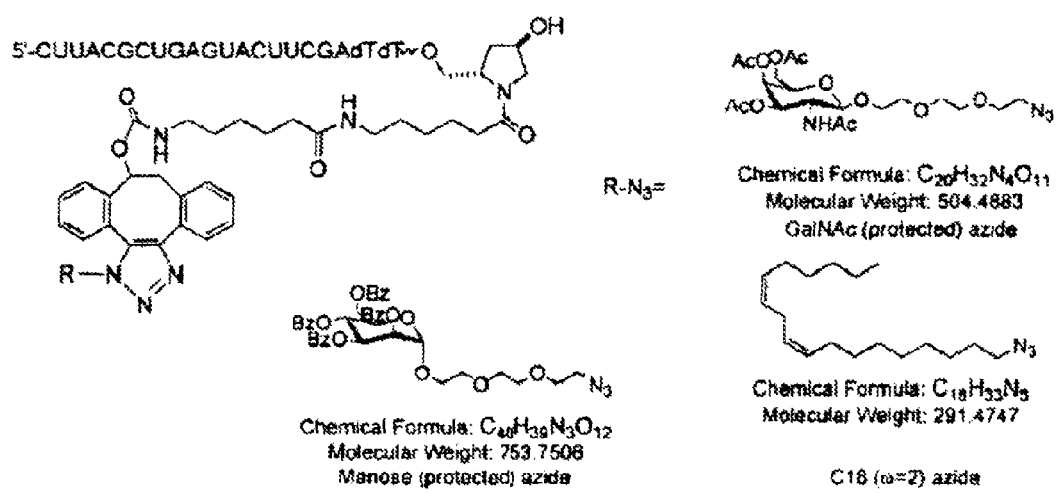

Cu(I)-Free Click Reactions of 3'-alkyne-RNA (A53213.1) with GalNAc (Protected), Mannose (Protected) and C18 Azides in Solution Phase (FIG. 4)

To 3'-alkyne-RNA (A53213.1) (0.05 µmol, 75 µL RNA from 0.67 mM stock solution in water) was added an azide (FIG. 4) (20 equiv by alkyne, 1 µmol, 20 µL azide of a 50 mM solution in methanol for GalNAc (protected) azide and mannose (protected) azide, THF for C18 azide. MeOH was added to obtain a total volume of 200 µL for click reactions with GalNAc (protected) azide. For mannose (protected) azide, MeOH/THF (1:1 v/v) was added to obtain a clear solution of 300 µL. For click reaction with C18 azide, MeOH/THF (1:1 v/v) was added to obtain a clear solution of 200 µL. The reaction was kept at room temperature for 18 hours or 60 hours. The click reaction was monitored by analytical RP-HPLC by injecting 20 µL of 30 fold diluted reaction mixture into an Agilent HPLC with DNAPAC™ PA-200 column (4×250 mm) and a gradient of 8-20% buffer B in 16 min at a flowrate of 1 mL/min. Buffer A contains 20 mM Tris HCl pH 8.0, 10 mM NaClO$_4$, 1 mM EDTA and 50% ACN. Buffer B contains 20 mM Tris HCl, pH 8.0, 800 mM NaClO$_4$, 1 mM EDTA and 50% ACN. The HPLC analysis is shown in FIG. 5.

Figure 5:
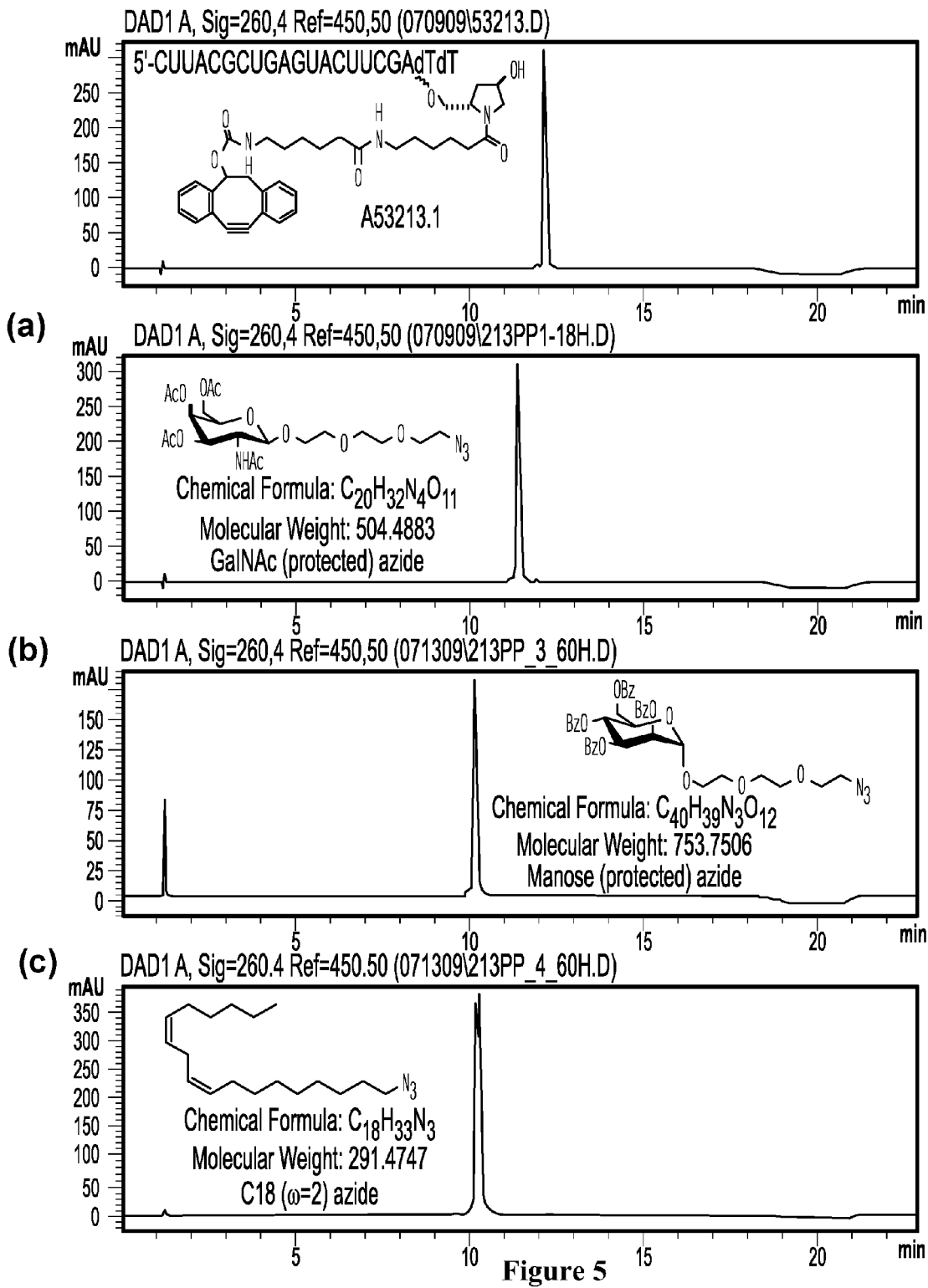
FIG. 5 depicts an HPLC analysis of click reactions of 3'-alkyne-RNA (A53213.1) with (a) GalNAc (protected) azide; (b) mannose (protected) azide; and (c) C18 azide in solution phase.

It is shown that click reactions of 3'-alkyne-RNA (A53213.1) with GalNAc (protected), mannose (protected) azide and C18 azide all went completion in this experiment (FIG. 5). All click products were confirmed with right molecular weight by LC/MS analysis (Table 2).

Example 8

Figure 6:
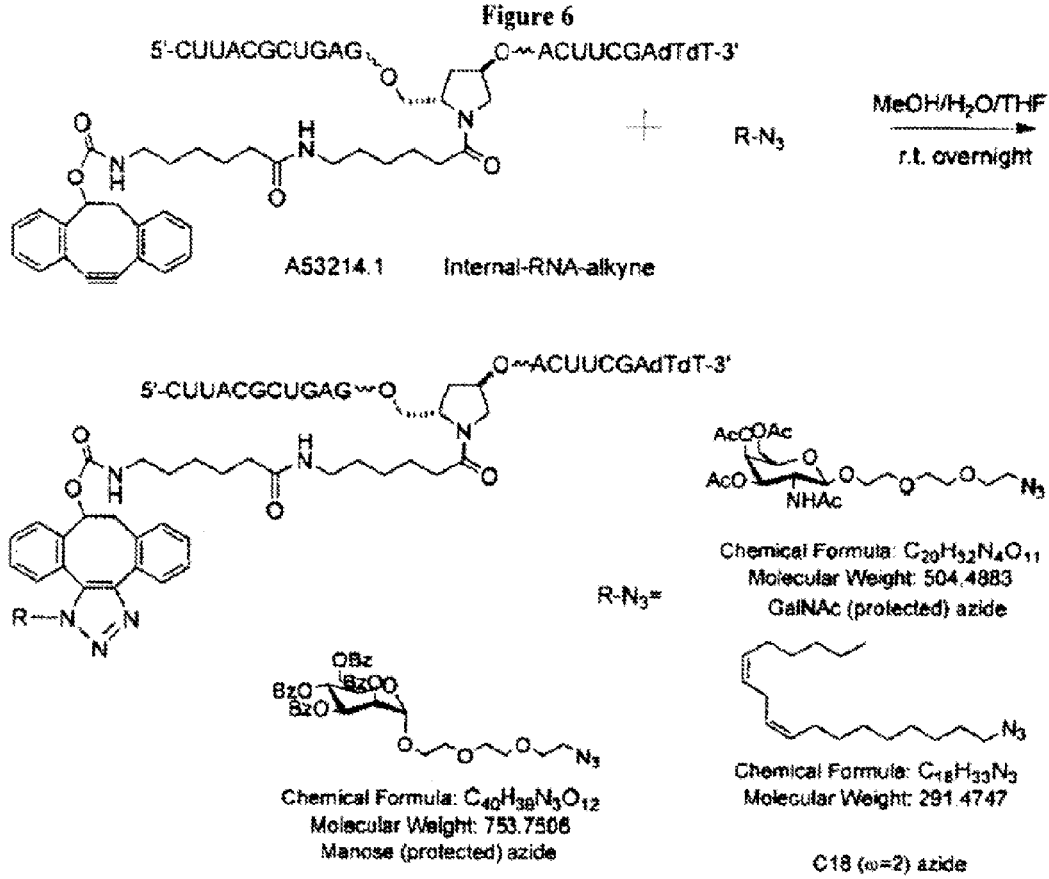
FIG. 6 depicts the click internal-alkyne-RNA (A53214.1) with different protected azides in solution phase.

Cu(I)-Free Click Reactions Of Internal-Alkyne-RNA (A53214.1) with GalNAc (Protected), Mannose (Protected) and C18 Azides in Solution Phase (FIG. 6)

To internal-alkyne-RNA (A53214.1) (0.05 µmol, 33 µL RNA from 1.51 mM stock solution in water) was added an azide (FIG. 6) (20 equiv by alkyne, 1 µmol, 20 µL azide of a 50 mM solution in methanol for GalNAc (protected) azide and mannose (protected) azide, THF for C18 azide. MeOH was added to obtain a total volume of 200 µL for click reactions with GalNAc (protected) azide. For mannose (protected) azide, MeOH/THF (1:1 v/v) was added to obtain a clear solution of 300 µL. For click reaction with C18 azide, MeOH/THF (1:1 v/v) was added to obtain a clear solution of 200 µL. The reaction was kept at room temperature for overnight (18 hours). The click reaction was monitored by analytical RP-HPLC by injecting 20 µL of 30 fold diluted reaction mixture into an Agilent HPLC with DNAPAC™ PA-200 column (4×250 mm) and a gradient of 8-20% buffer B in 16 min at a flowrate of 1 mL/min. Buffer A contains 20 mM Tris HCl pH 8.0, 10 mM NaClO$_4$, 1 mM EDTA and 50% ACN. Buffer B contains 20 mM Tris HCl, pH 8.0, 800 mM NaClO$_4$, 1 mM EDTA and 50% ACN. The HPLC analysis is shown in FIG. 7.

Figure 7:
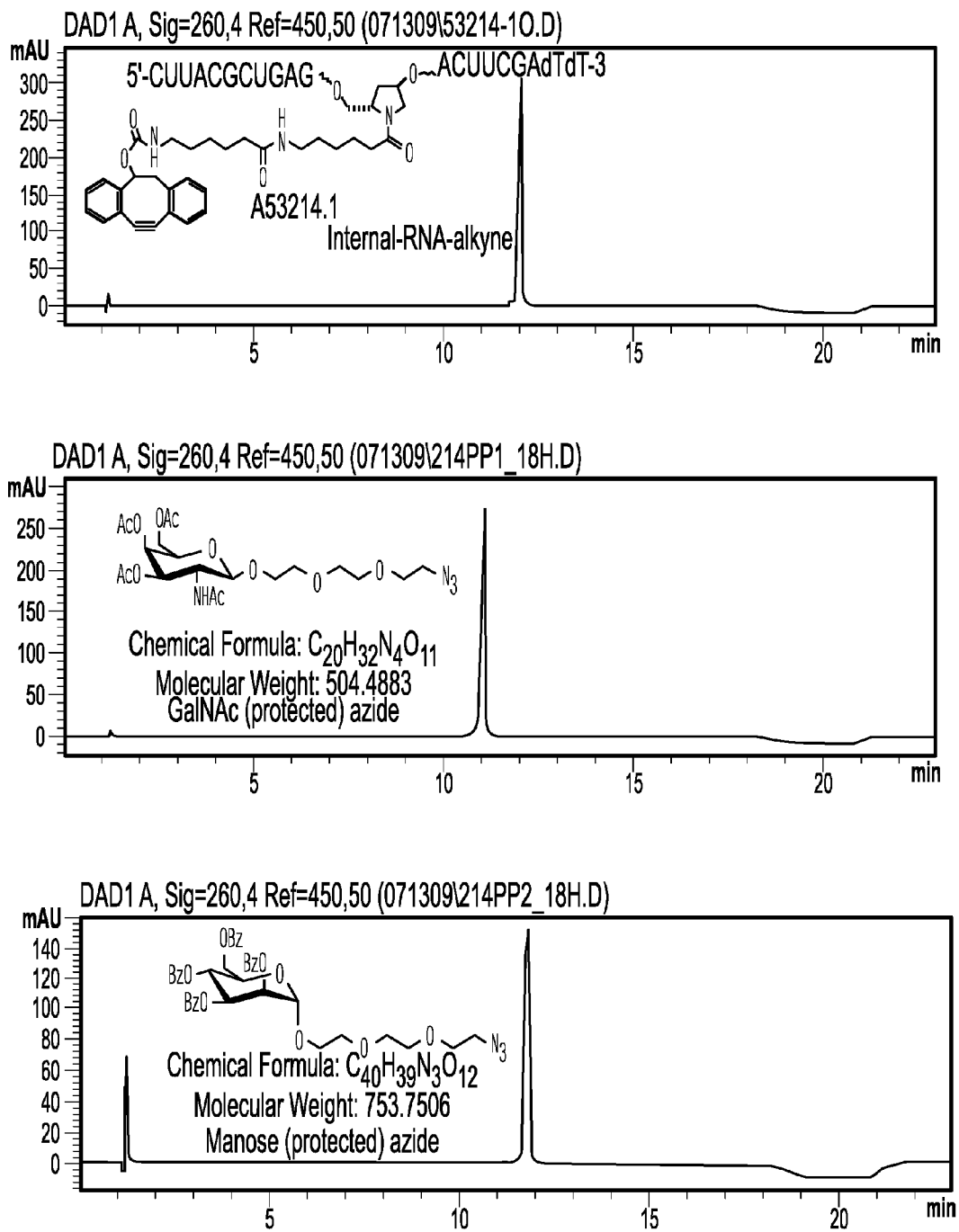
FIG. 7 depicts an HPLC analysis of click reactions of internal-alkyne-RNA (A53214.1) with (a) GalNAc (protected) azide; (b) mannose (protected) azide; and (c) C18 azide in solution phase.
Figure 7:
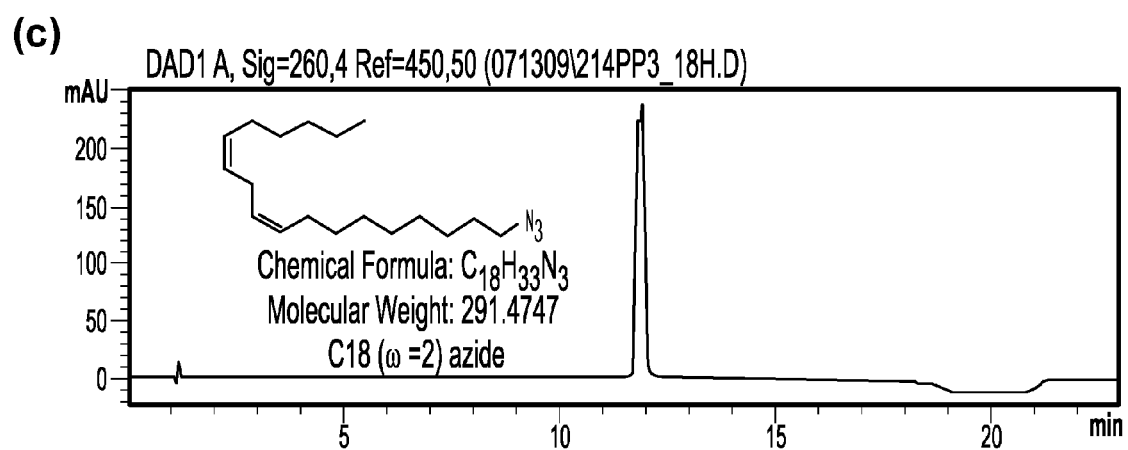

It is shown that click reactions of internal-alkyne-RNA (A53214.1) with GalNAc (protected), mannose (protected) azide and C18 azide all went completion in this experiment (FIG. 7). All click products were confirmed with right molecular weight by LC/MS analysis (Table 3).

Example 9

Figure 8:
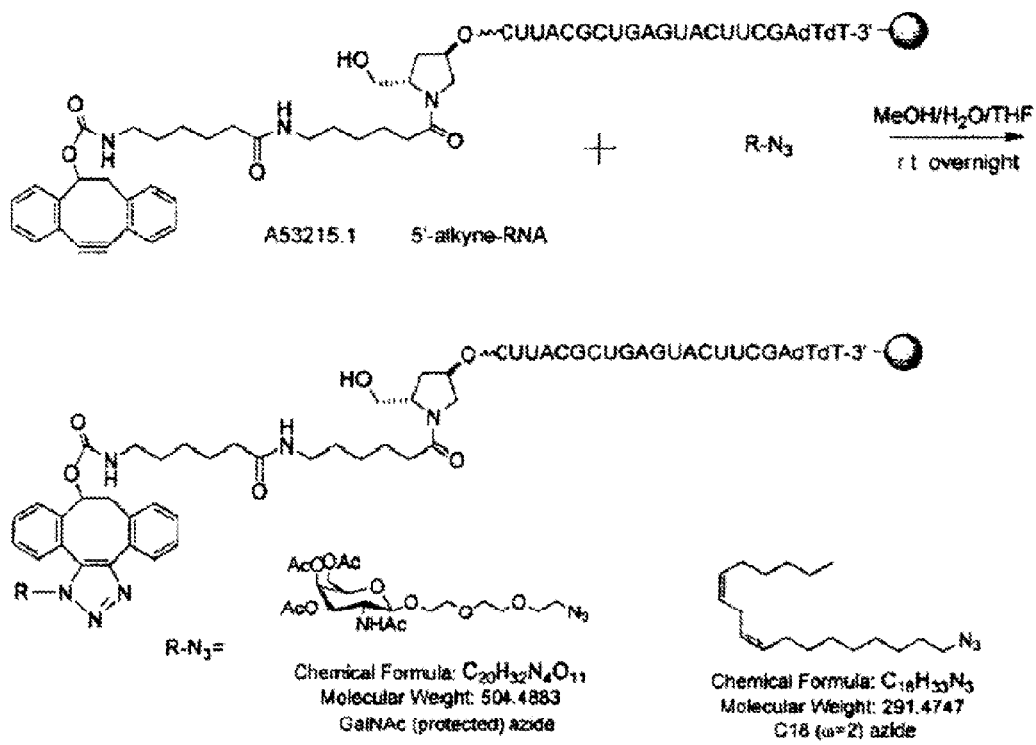
FIG. 8 depicts the click 5'-alkyne-RNA with GalNAc (protected) and C18 azides on CPG.

Cu(I)-Free Click Reactions of 5'-alkyne-RNA (A53215.1) with GalNAc (Protected) and C18 Azides on Solid Support (FIG. 8)

To a solid-supported 5'-alkyne-RNA (A53215.1) in Table 4 (0.646 µmol) was added an azide (15 equiv by alkyne, 10 µmol, 200 µL of a 50 mM solution in methanol for GalNAc (protected) azide and in THF for C18 azide (FIG. 8). The reaction was kept at room temperature for overnight (18 hours). The CPG was filtered, washed and deprotected. The mixture after deprotection was analyzed by RP-HPLC on an Agilent HPLC with DNAPAC™ PA-200 column (4×250 mm) and a gradient of 8-20% buffer B in 16 min at a flowrate of 1 mL/min. Buffer A contains 20 mM Tris HCl pH 8.0, 10 mM NaClO$_4$, 1 mM EDTA and 50% ACN. Buffer B contains 20 mM Tris HCl, pH 8.0, 800 mM NaClO$_4$, 1 mM EDTA and 50% ACN. The HPLC analysis is shown in FIG. 9.

Figure 9:
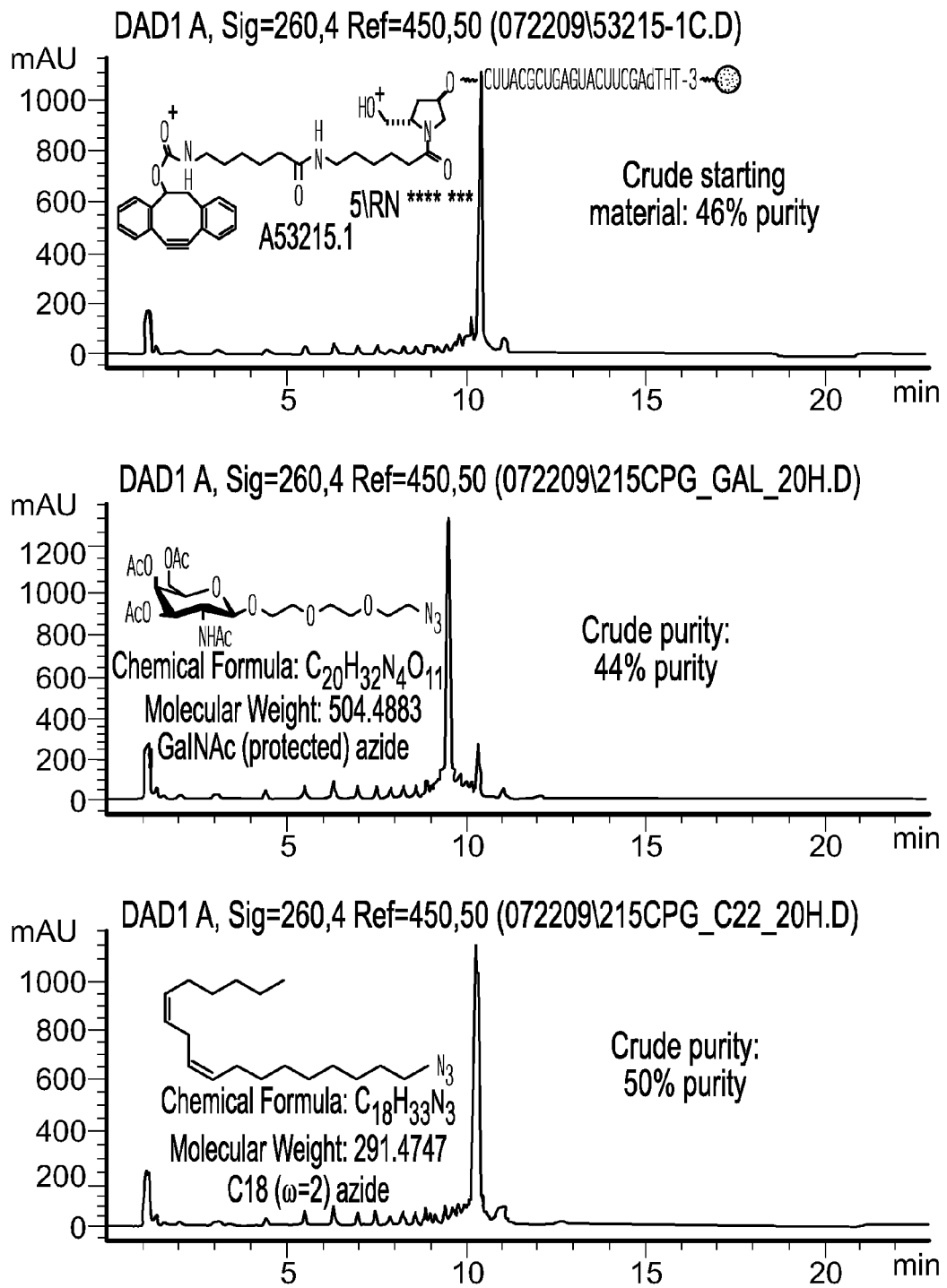
FIG. 9 depicts an HPLC analysis of products from click reactions of 5'-alkyne-RNA (A53215.1 (SEQ ID NO: 32)) with GalNAc (protected) and C18 azides on CPG.
Figure 10:
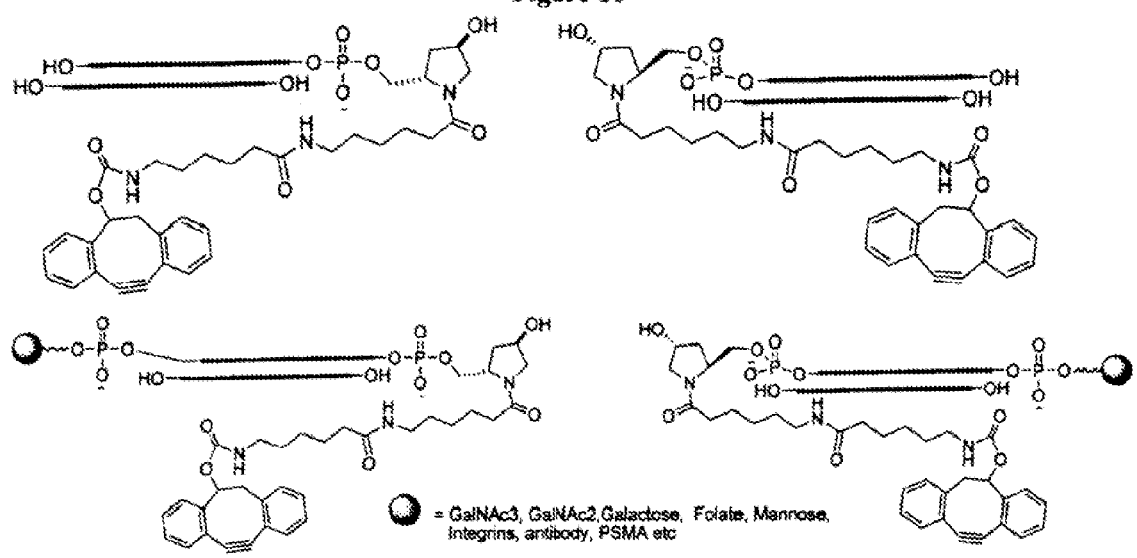
FIG. 10 depicts various 3' and 5' RNA conjugates with alkyne derivatives.

It is shown that click reactions of 5'-alkyne-RNA (A53215.1) with GalNAc (protected), and C18 azide on solid support both went completion in this experiment (FIG. 9). All click products were confirmed with right molecular weight by LC/MS analysis (Table 4).

TABLE 1

Click 5'-alkyne-RNA with azides in solution phase

| Sequence ID | Note | MW Calc. (g/mol) | MW obs. (g/mol) |
|---|---|---|---|
| A53215.1 | 5'-alkyne-RNA, starting material | 7257.67 | 7256.77 |
| A53215_Gal | Click with GalNAc (protected) azide | 7762.16 | 7761.45 |
| A53215_Man | Click with mannose (protected) azide | 8011.42 | 8010.55 |
| A53215_C18 | Click with C18 azide | 7549.14 | 7548.42 |
| A53215_GalDep | Click with GalNAc3 (unprotected) azide | 8945.59 | 8945.57 |
| A53215_ManDep | Click with mannose (unprotected) azide | 7595.03 | 7592.94 |

Note:

A-53215.1 sequence (5'-3') information:

Q99CUUACGCUGAGUACUUCGAdTdT (SEQ ID NO: 32)

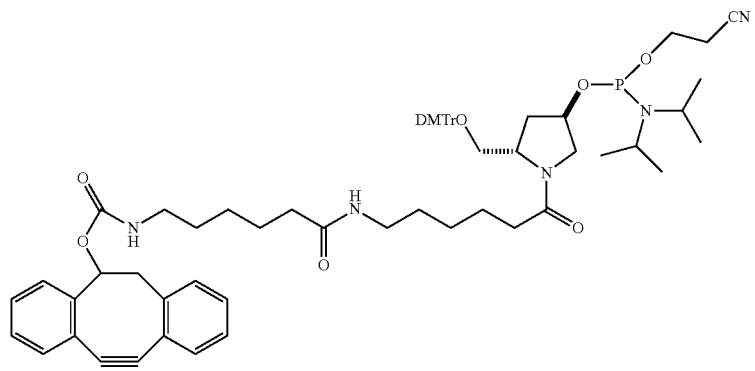

alkyne phosphoramidite
Molecular Weight: 1092.31
Generate 5'- and internal-alkyne-RNA (coded as Q99)

40

TABLE 2

Click 3'-alkyne-RNA with protected azides in solution phase

| Sequence ID | Note | MW Calc. (g/mol) | MW obs. (g/mol) |
|---|---|---|---|
| A53213.1 | 3'-alkyne-RNA, starting material | 7258.68 | 7256.73 |
| A53213_Gal | Click with GalNAc (protected) azide | 7763.17 | 7761.44 |
| A53213_Man | Click with mannose (protected) azide | 8012.43 | 8010.56 |
| A53213_C18 | Click with C18 azide | 7550.15 | 7548.41 |

Note:

A-53213.1 sequence (5'-3') information:

CUUACGCUGAGUACUUCGAdTdTL146 (SEQ ID NO: 33)

TABLE 2-continued

Click 3'-alkyne-RNA with protected azides in solution phase

| Sequence ID | Note | MW Calc. (g/mol) | MW obs. (g/mol) |
|---|---|---|---|

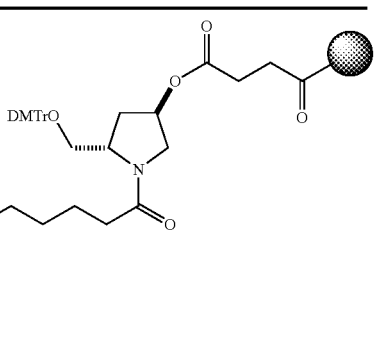

alkyne-CPG
60 µmol/g
Generate 3'-alkyne-RNA (coded as L146)

TABLE 3

Click internal-alkyne-RNA with protected azides in solution phase

| Sequence ID | Note | MW Calc. (g/mol) | MW obs. (g/mol) |
|---|---|---|---|
| A53214.1 | Internal-alkyne-RNA, starting material | 6951.5 | 6950.72 |
| A53214_Gal | Click with GalNAc (protected) azide | 7455.99 | 7455.43 |
| A53214_Man | Click with mannose (protected) azide | 7705.25 | 7704.54 |
| A53214_C18 | Click with C18 azide | 7242.97 | 7242.51 |

Note:
A-53214.1 sequence (5'-3') information:
CUUACGCUGAGQ99ACUUCGAdTdT (SEQ ID NO: 34)
(Q99 refers to Table 3)

TABLE 4

Click 5'-alkyne-RNA-CPG with protected azides on solid support

| Sequence ID | Note | MW Calc. (g/mol) | MW obs. (g/mol) |
|---|---|---|---|
| A53215.1 | 5'-alkyne-RNA, starting material | 7257.67 | 7256.77 |
| 215CPG_Gal | Click with GalNAc (protected) azide on CPG | 7636.08 | 7635.22 |
| 215CPG_C18 | Click with C18 azide on CPG | 7549.14 | 7547.49 |

Note:
A53215.1 sequence (5'-3') information:
Q99CUUACGCUGAGUACUUCGAdTdT-CPG (SEQ ID NO: 32)
(Q99 refers to Table 3)

Synthesis of New Alkyne Derivatives

TABLE 5

Alkyne derivatives

Structure

11 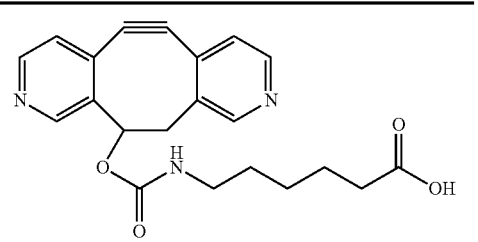

508

22 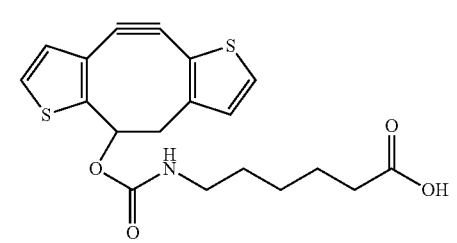

538

33 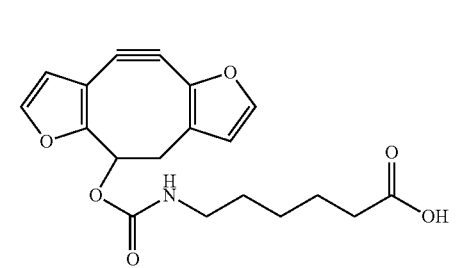

517

TABLE 5-continued
Alkyne derivatives
| | Structure |
|---|---|
| 44 | [structure 547] |
| 55 | [structure 529] |
| 66 | [structure 556] |
| 77 | [structure 565] |
| 88 | [structure 567a] |
| 99 | [structure 567b] |
| 110 | [structure 567c] |
| 111 | [structure 567d] |
| 112 | [structure 567e] |
Example 10
Synthesis Alkyne Derivative 508
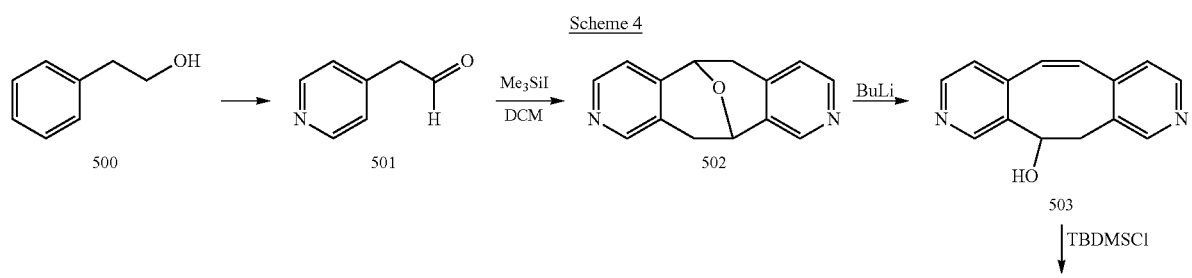
Scheme 4

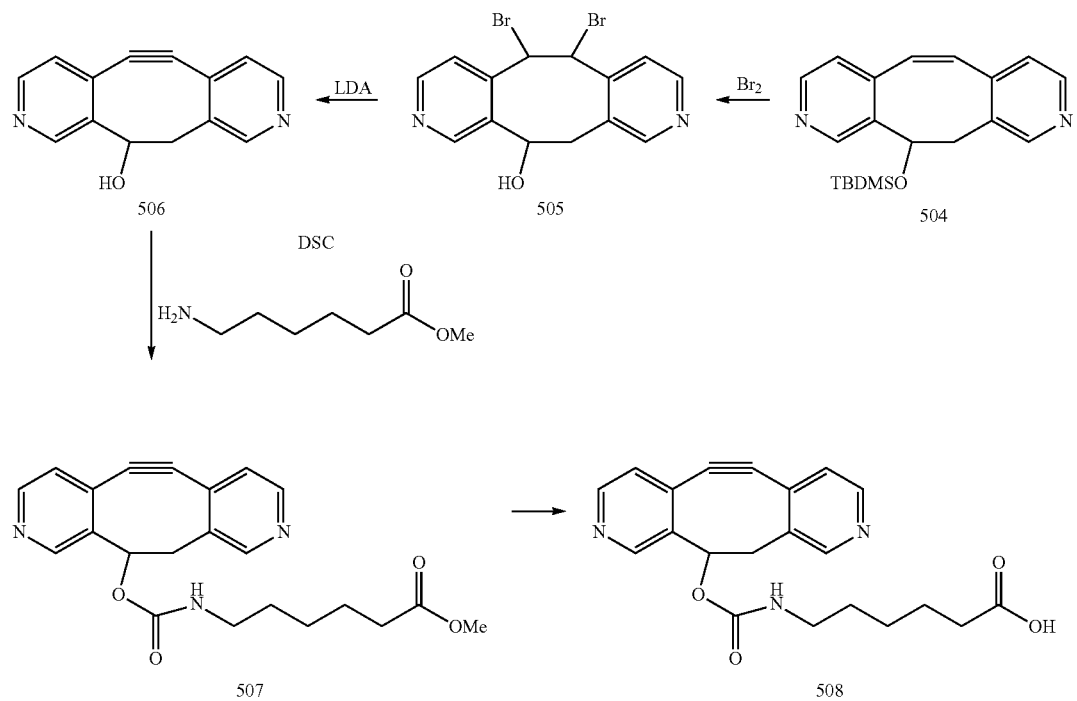
Alkyne derivative 508 is prepared by following the procedure given in scheme 1
Example 11
Synthesis of Alkyne Derivative 517
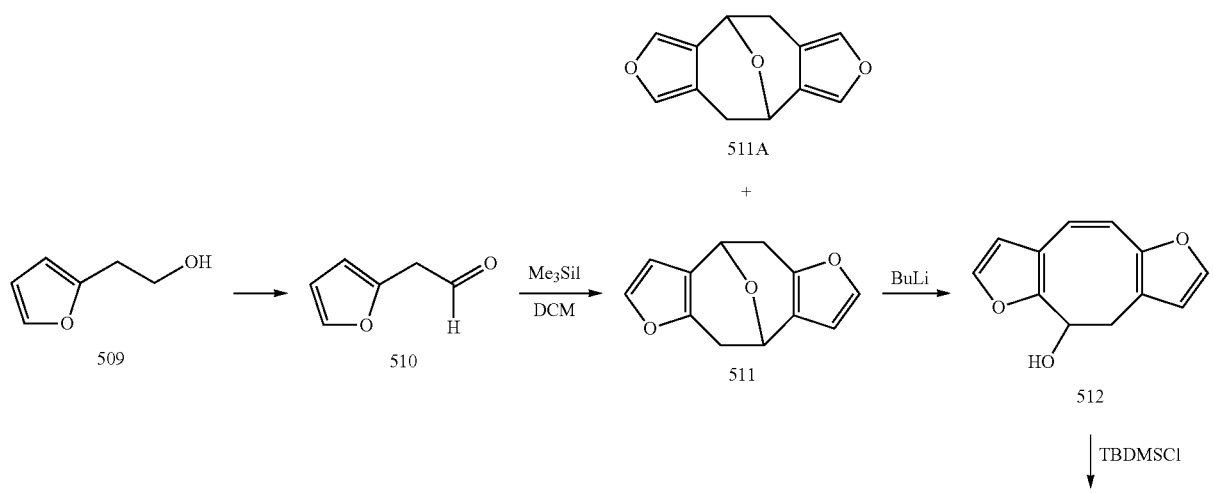

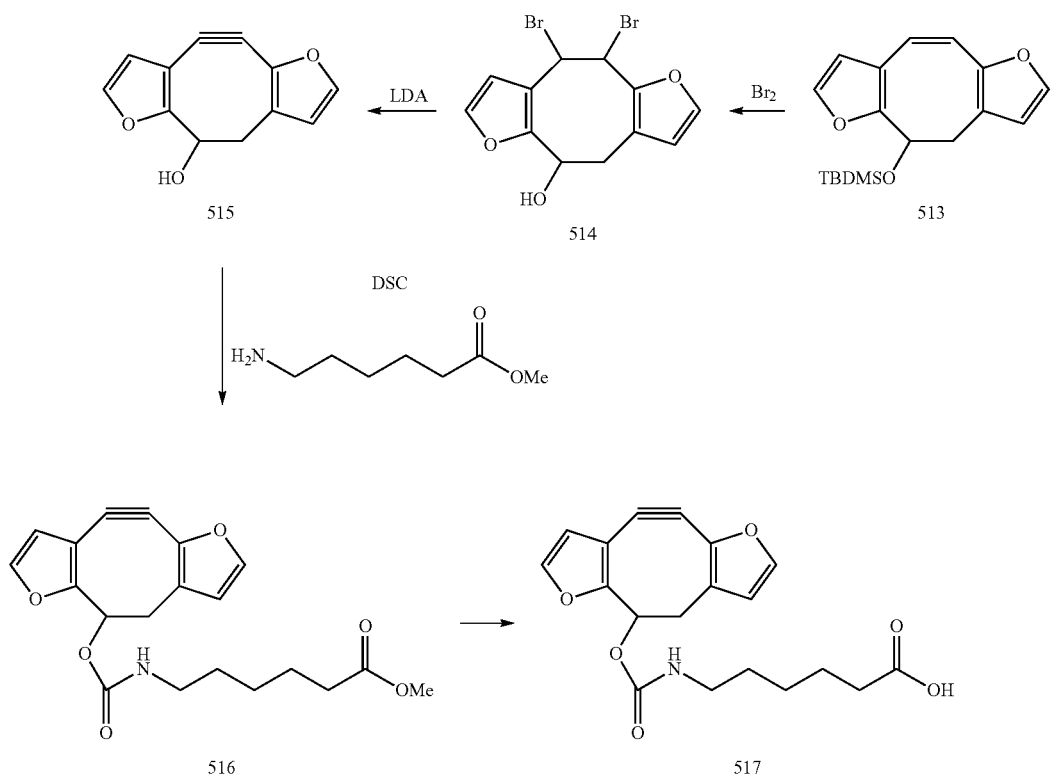
Alkyne derivative 517 is prepared by following the procedure given in scheme 1
Example 12
Synthesis of alkyne derivative 529
Scheme 6
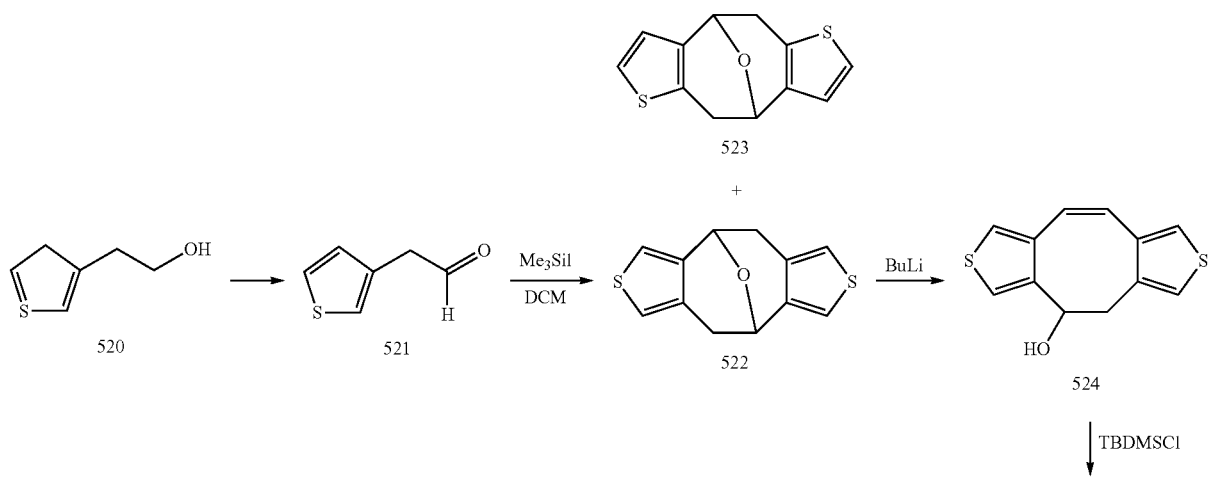

101   102
-continued
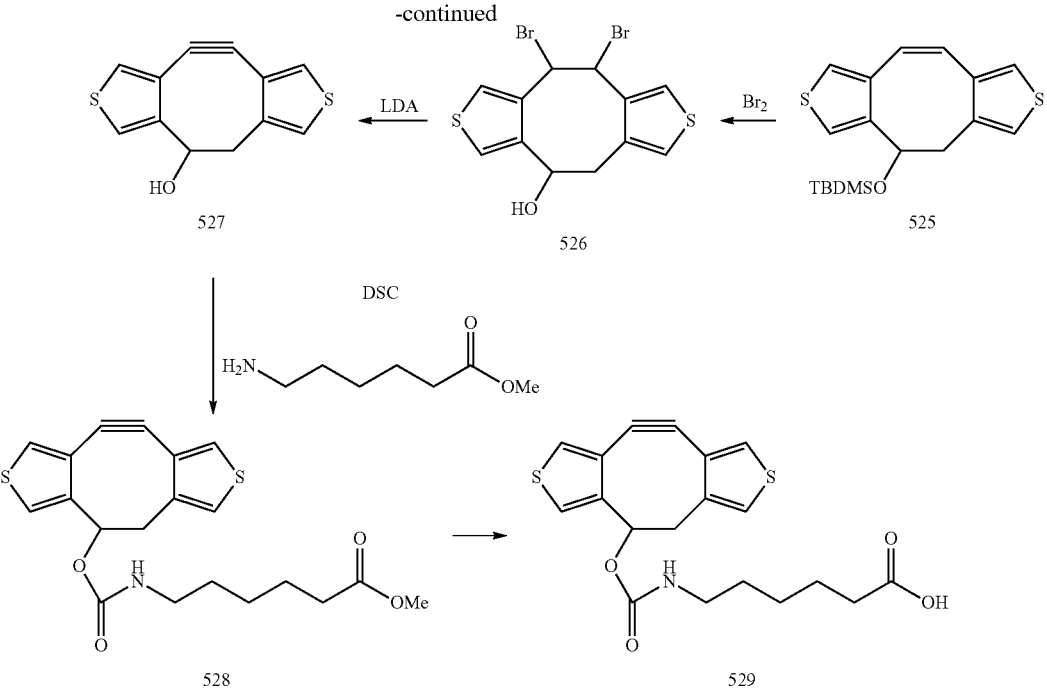
Alkyne derivative 529 is prepared by following the procedure given in scheme 1
Example 13
Synthesis of Alkyne Derivative 538
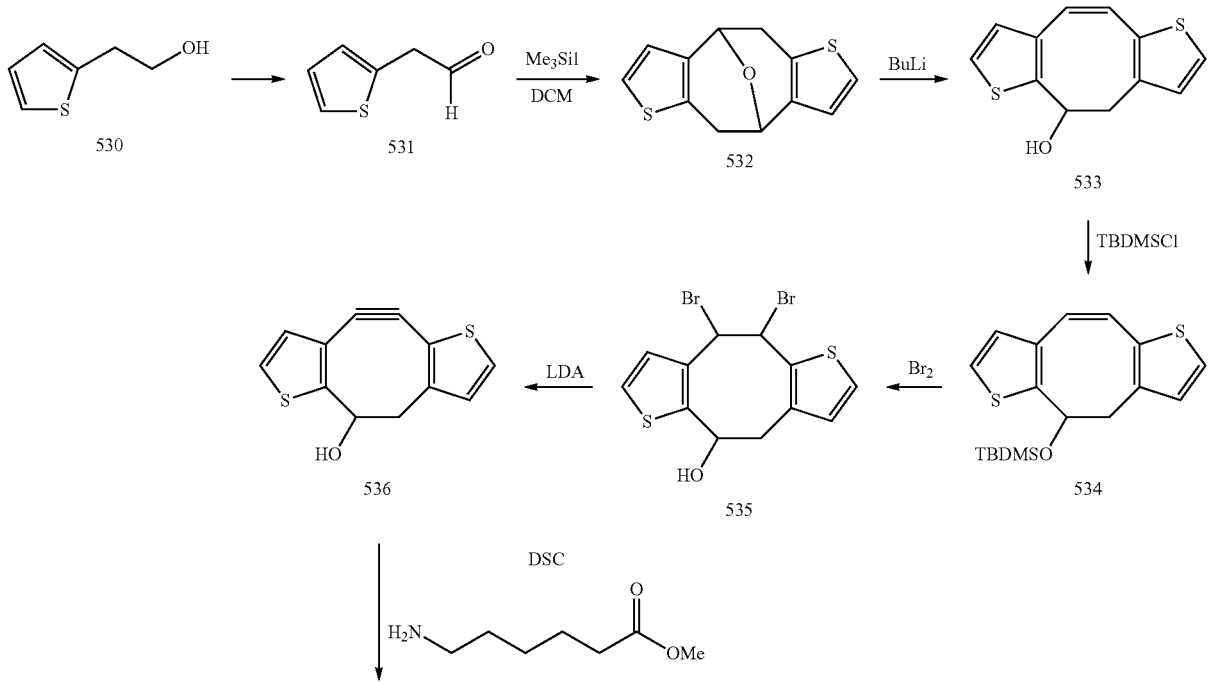

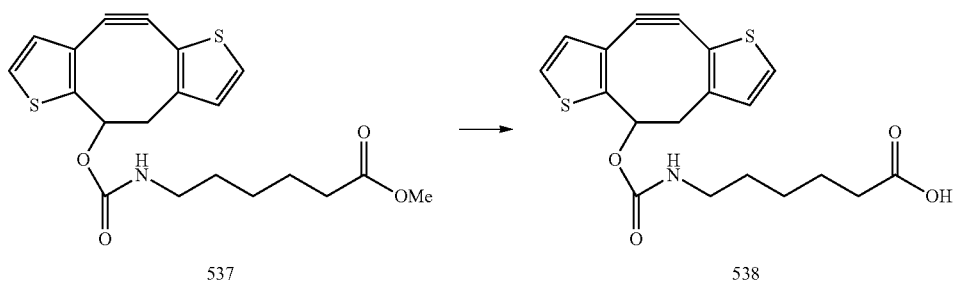
Alkyne derivative 538 is prepared by following the procedure given in scheme 1
Example 14
Synthesis of Alkyne Derivative 547
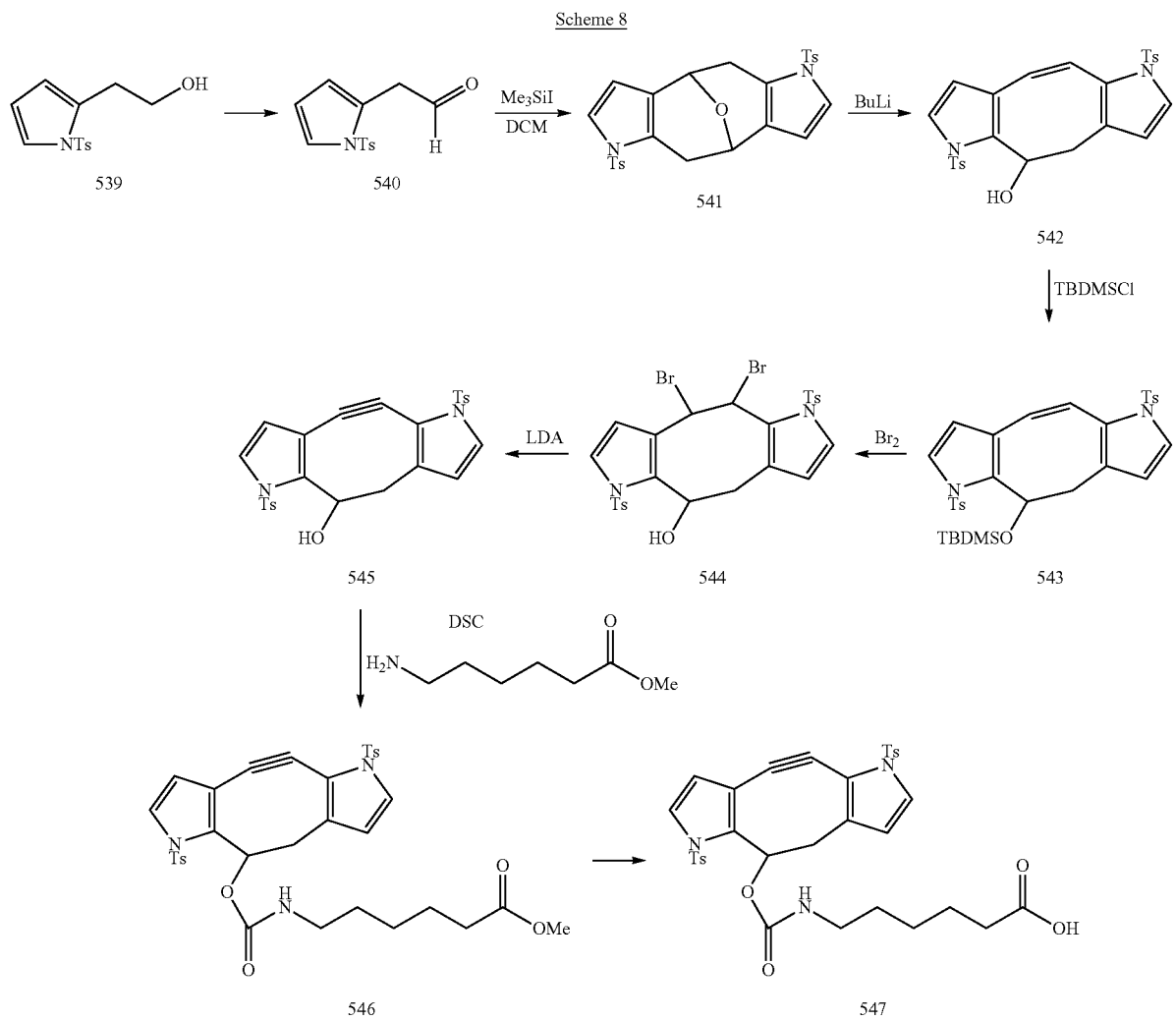

Alkyne derivative 547 is prepared by following the procedure given in scheme 1
Example 15
Synthesis of Alkyne Derivative 556
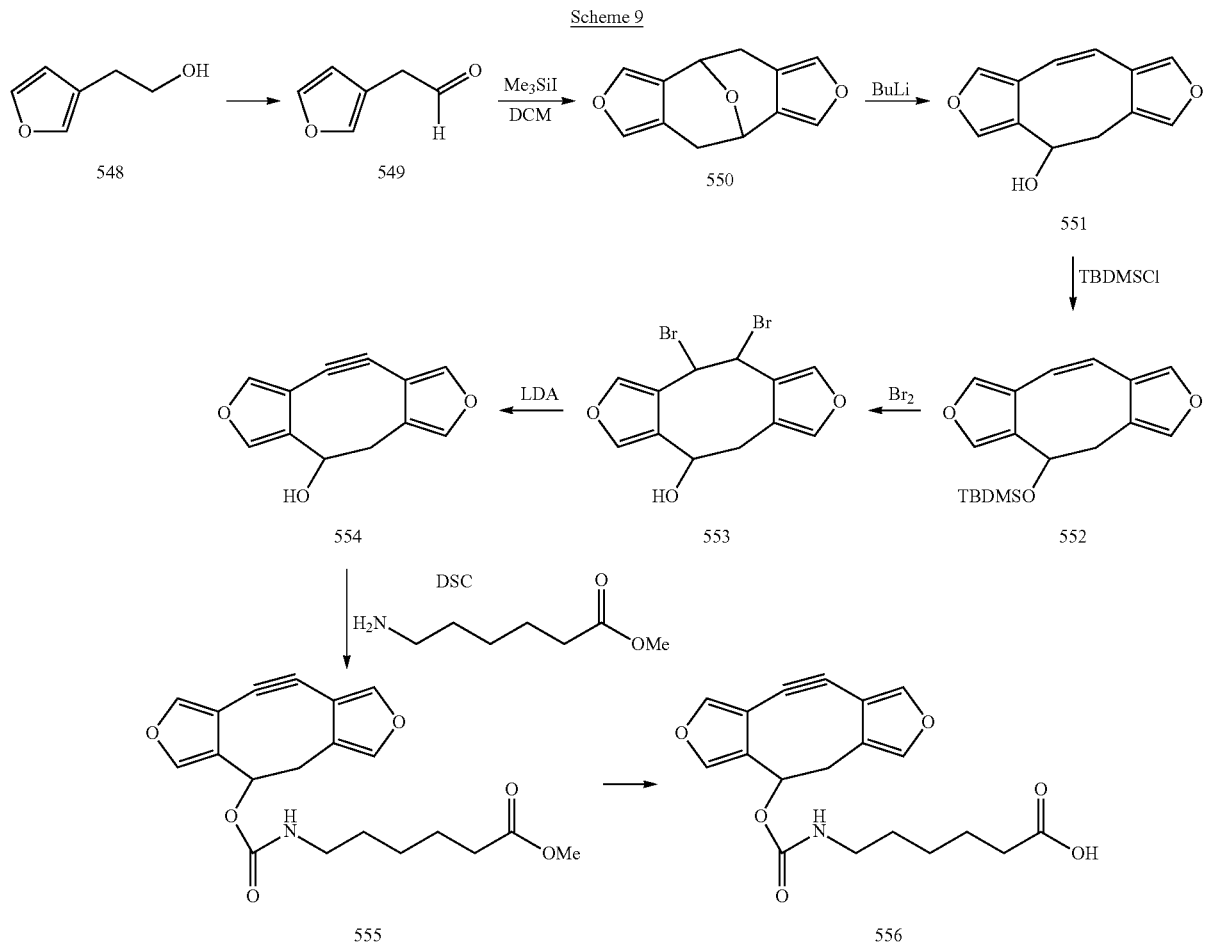
Alkyne derivative 556 is prepared by following the procedure given in scheme 1
Example 16
Synthesis of Alkyne derivative 565
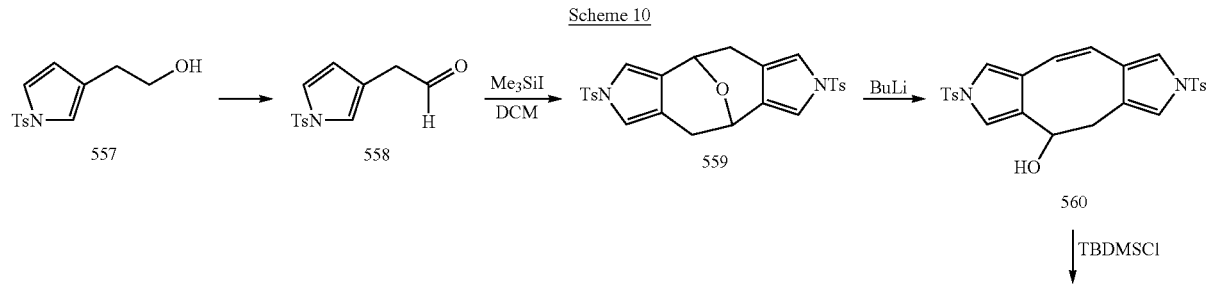

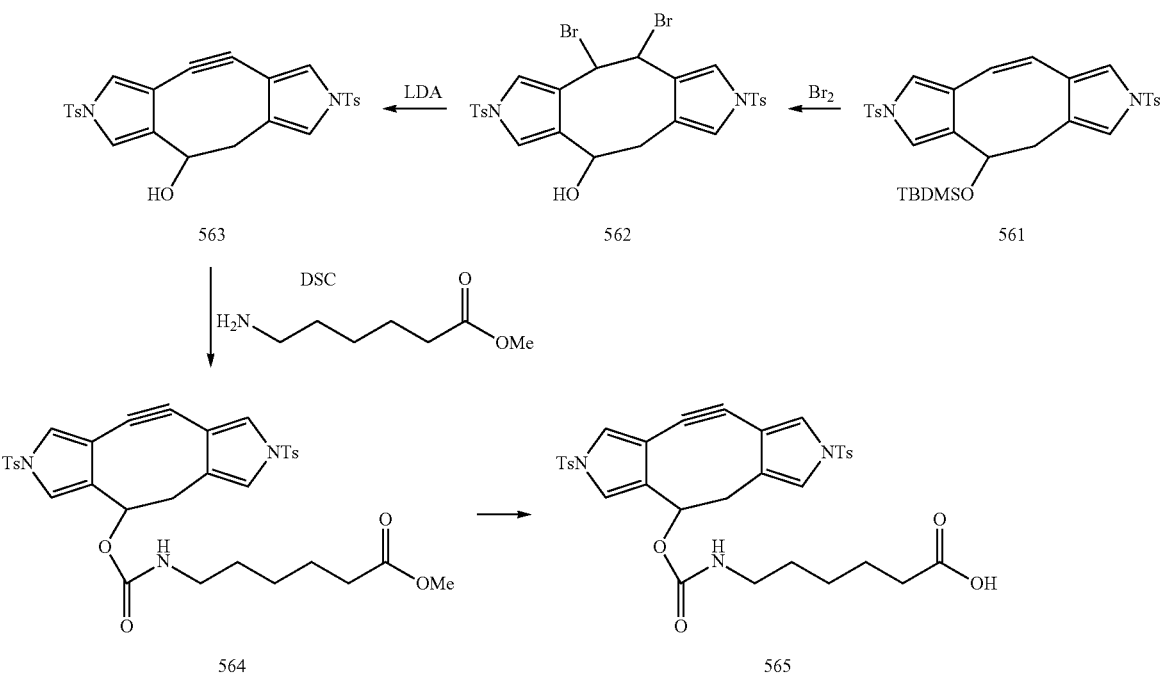
Alkyne derivative 565 is prepared by following the procedure given in scheme 1
Example 17
Synthesis of Alkyne Derivatives 576
Scheme 11
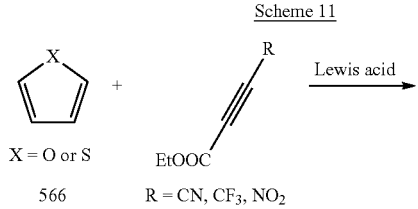
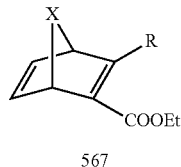
Alkyne derivative 567 is prepared by the Diels alder reaction of furan or thiophene with corresponding acetylene derivatives.
Example 18
Synthesis of 2' and 3' Amino Derivatives
Scheme 12
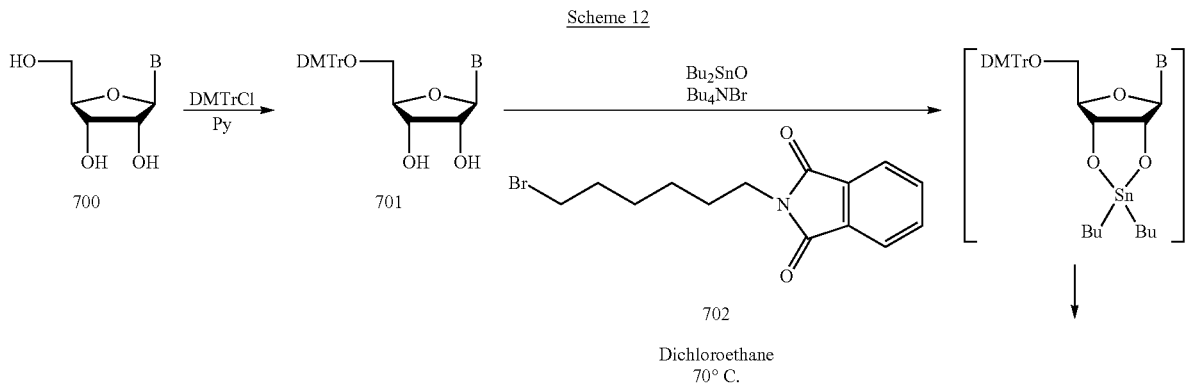
Dichloroethane
70° C.

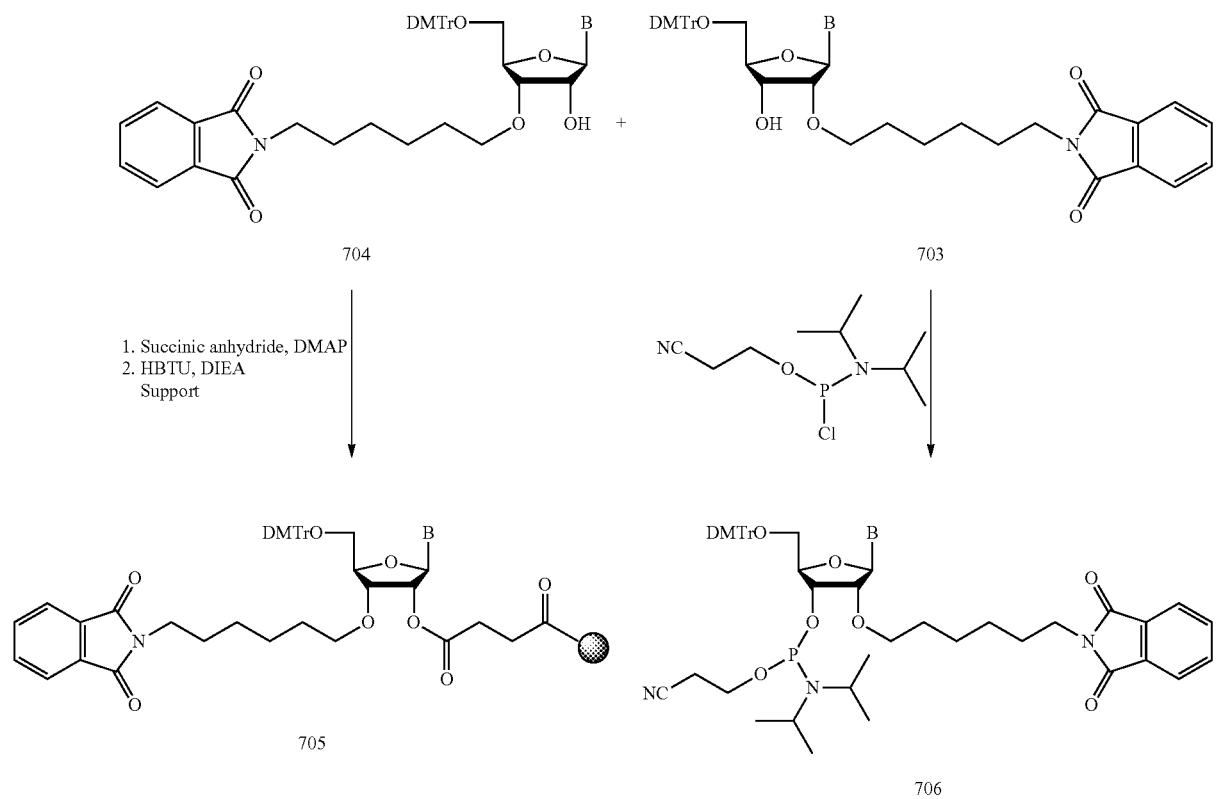
(For the synthesis of 2' and 3' phthalimido derivatives follows Nucleic Acids Symposium Series No. 52 51-52).
Example 19
Synthesis of 2' Alkyne Derivative 709
Scheme 13
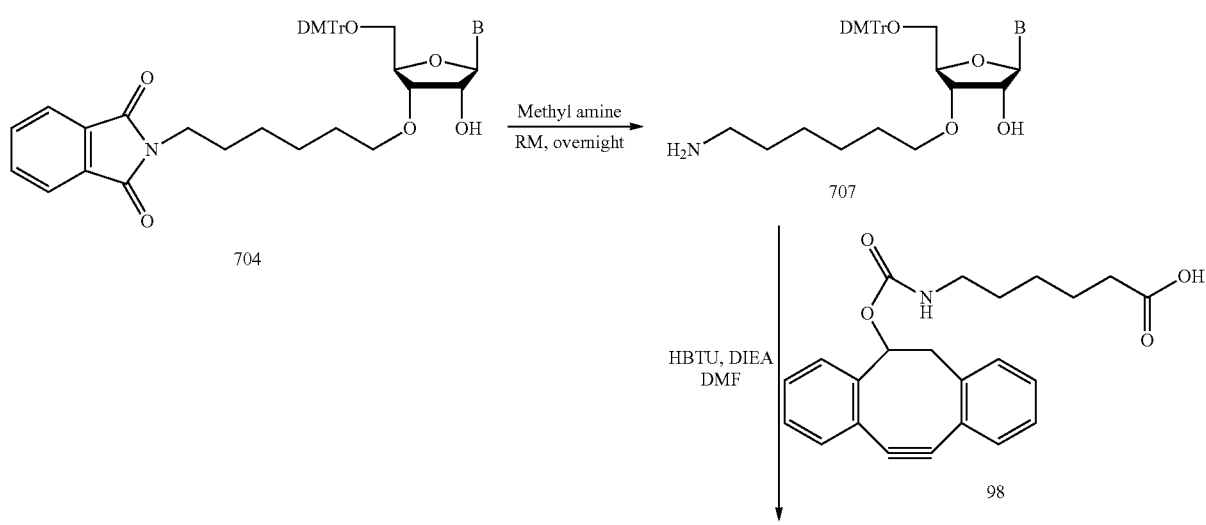

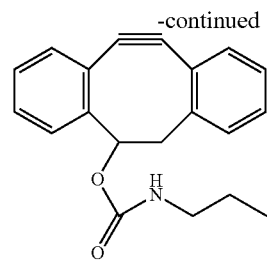

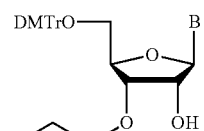

708

1. Succinic anhydride, DMAP
2. HBTU, DIEA
   Support

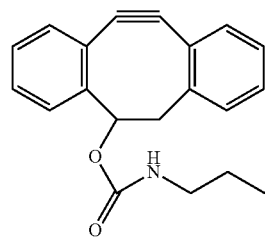

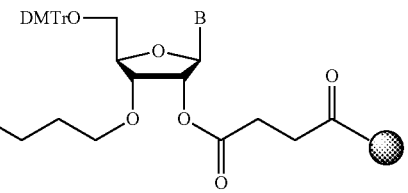

709

Synthesis of compound 709: Compound 704 is treated with methyl amine (33 wt % in ethanol) overnight to get compound 707. This derivative is coupled with the alkyne derivative 98 using HBTU/DIEA to get the hydroxyl compound 708. This is loaded on to the solid support using method described in scheme 3.

Example 20

Synthesis of 3' Alkyne Derivative 712

Scheme 14

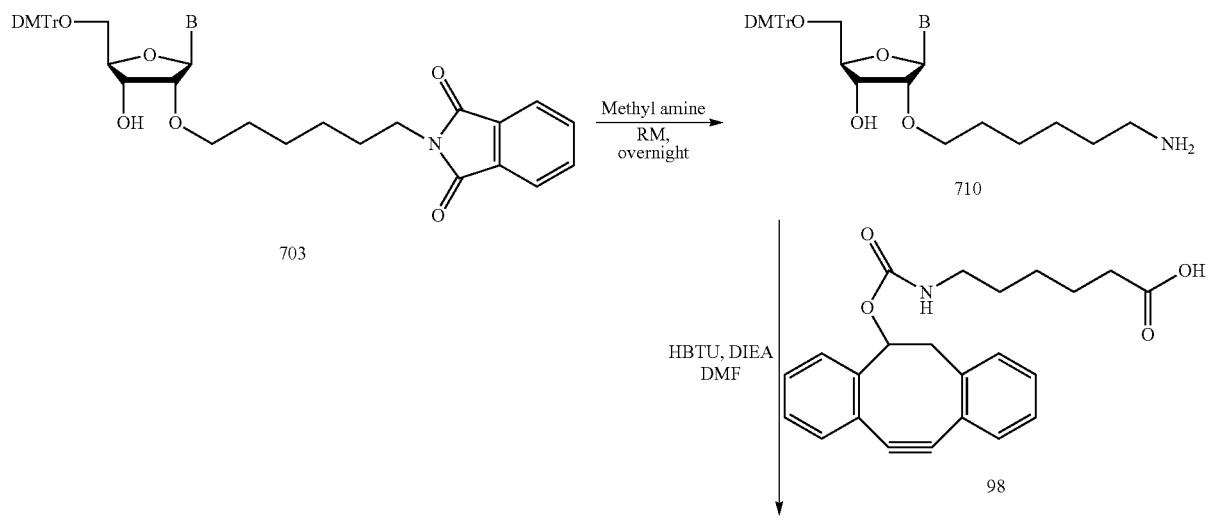

-continued
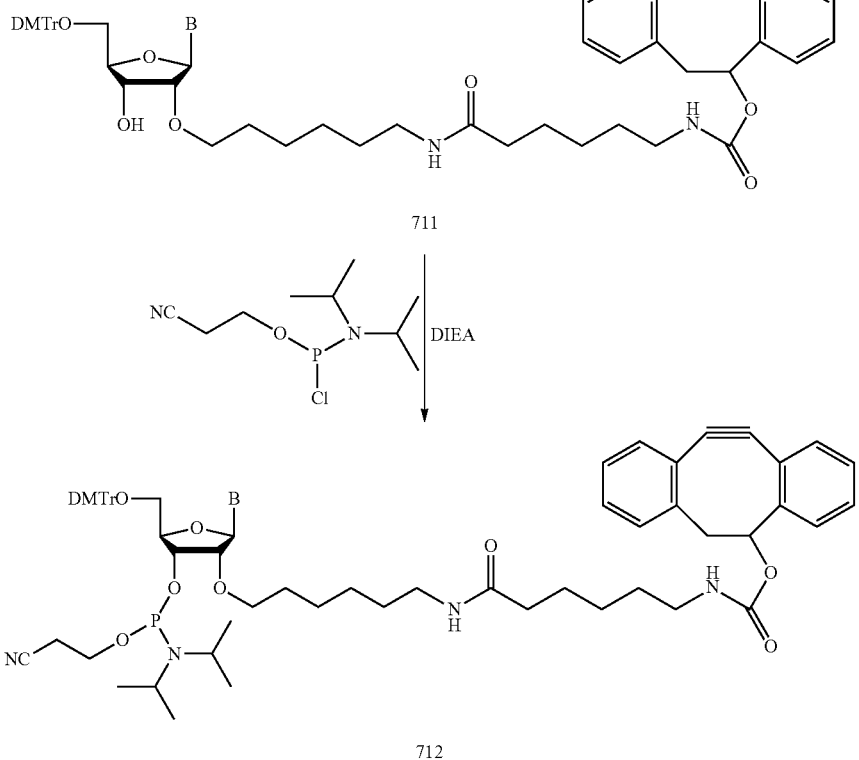
Synthesis of compound 712: Compound 703 is treated with methyl amine (33 wt % in ethanol) overnight to get compound 710. This derivative is coupled with the alkyne derivative 98 using HBTU/DIEA to get the hydroxyl compound 711. Amidite derivative 712 is synthesized using method described in scheme 3.
Example 21
Synthesis of 5' Alkyne Derivative 719

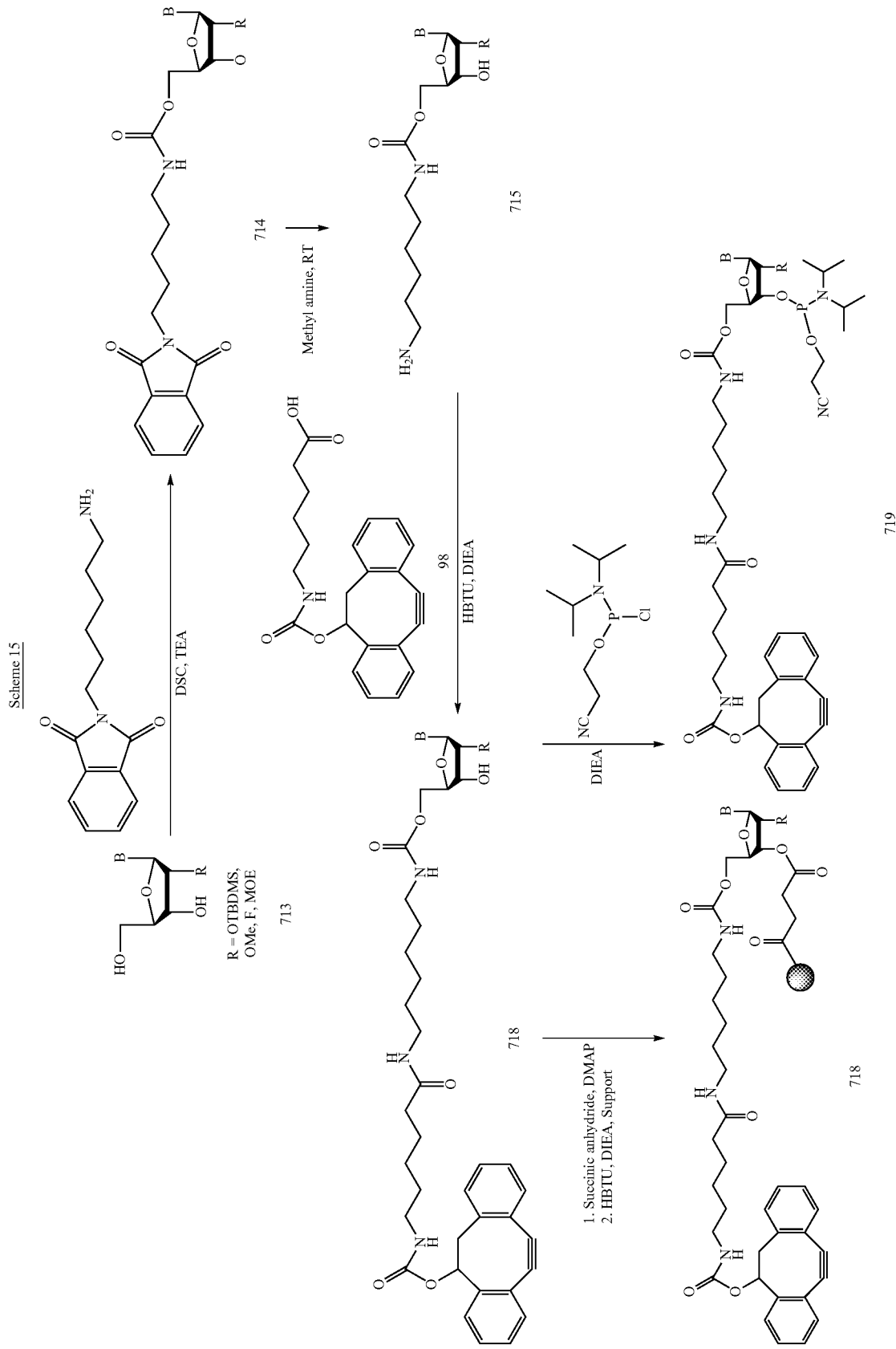

Synthesis of compounds 718 & 719: Compound 713 is treated with phthalimido protected diamine in presence of DSC and TEA to get 714. Phthalimido group is deprotected with methyl amine at RT to get 715. This compound is treated with the alkyne derivative to obtain the hydroxyl derivative 716. From this compound both the amidite and solid support is synthesized by the methods described earlier.

Example 22

Synthesis of Cytidine Derivatives

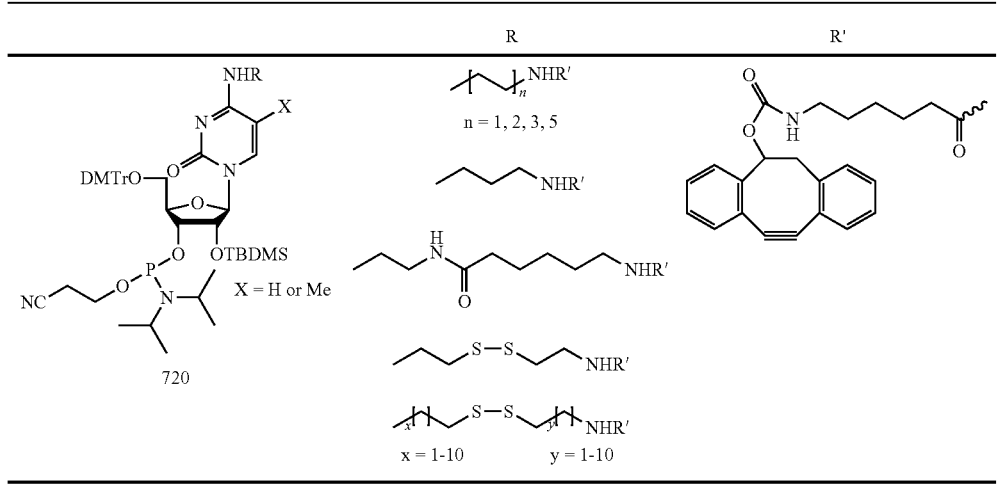

Scheme 16

(For the synthesis of compound 720 follows Manoharan M. Designer antisense oligonucleotides: Conjugation chemistry and Functionality placement, Chapter 17, *Antisense research and applications* Crooke, S. T.; and Lebleu, B. 1993 CRC and Manoharan M. Antisense & Nucleic acid Drug development 2002, 12, 103-128 and references there in)

Example 23

Synthesis of C-5 Derivatives

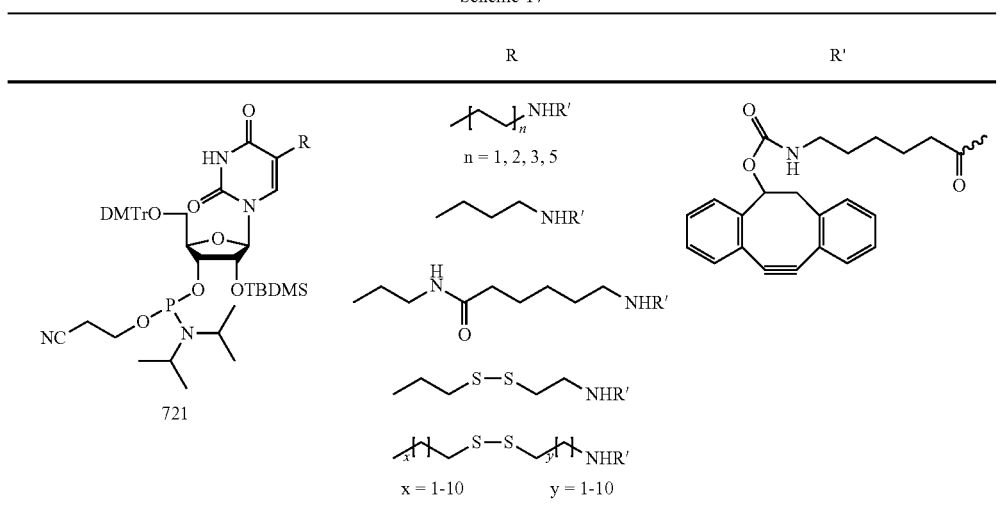

Scheme 17

(For the synthesis of compound 720 follows Manoharan M. Designer antisense oligonucleotides: Conjugation chemistry and Functionality placement, Chapter 17, *Antisense research and applications* Crooke, S. T.; and Lebleu, B. 1993 CRC and Manoharan M. Antisense & Nucleic acid Drug development 2002, 12, 103-128 and references there in)
Example 24
Synthesis of RNA Conjugates
Scheme 18
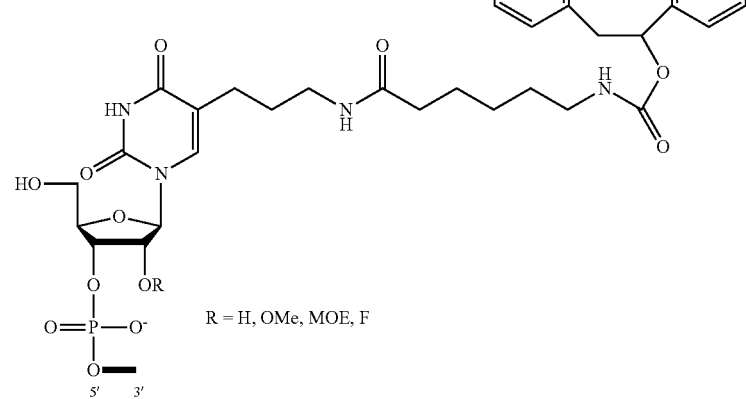
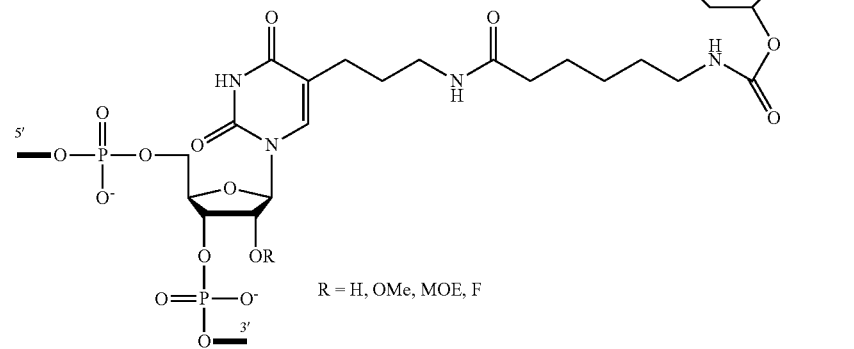
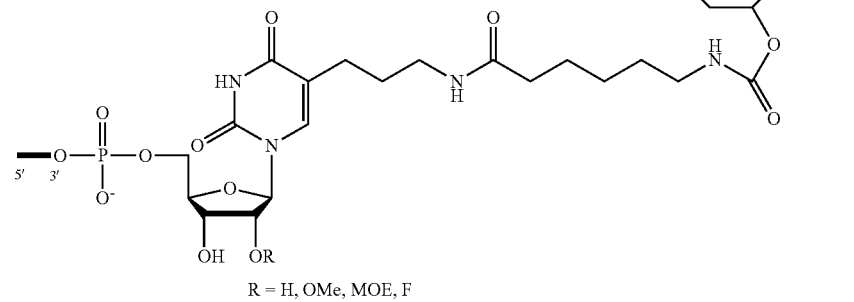

Example 25
Synthesis of RNA Conjugates
Scheme 19
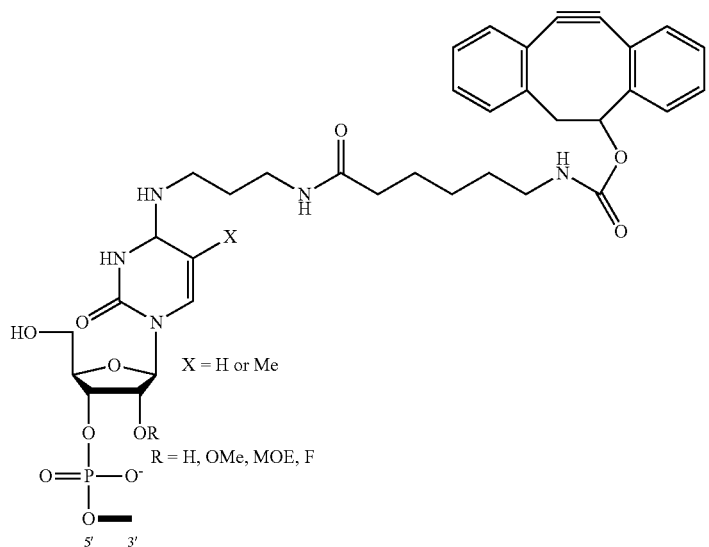
725
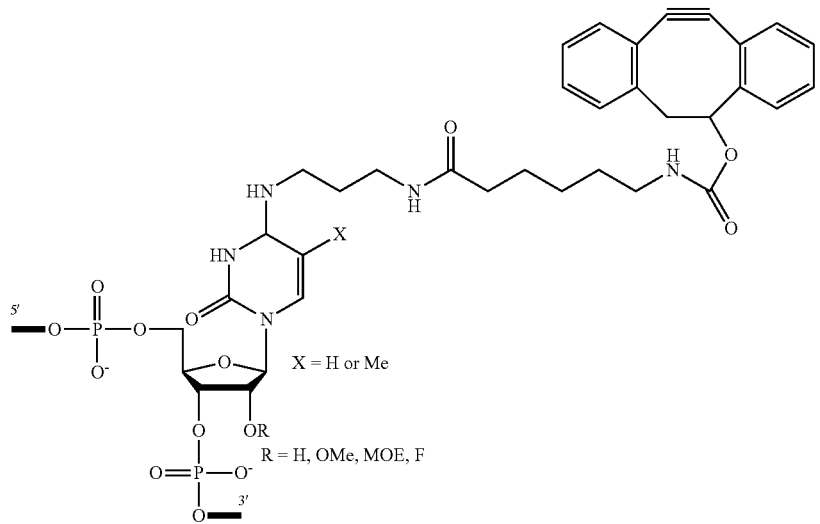
726
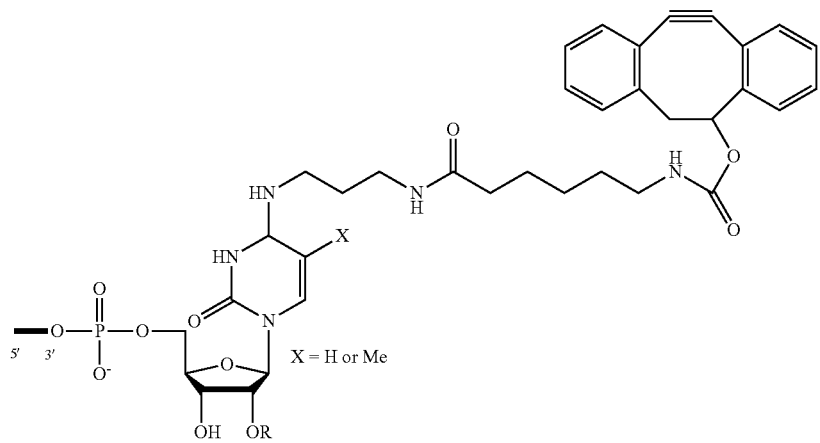
727

Example 25

Pseudouridine Conjugates

Scheme 20

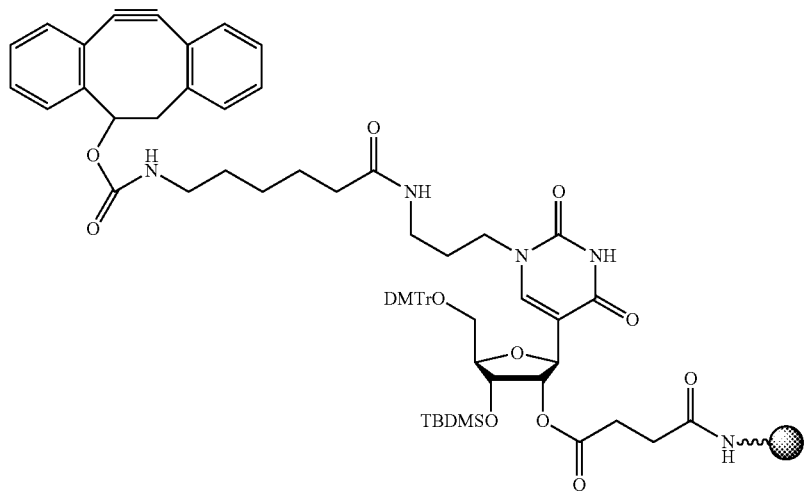

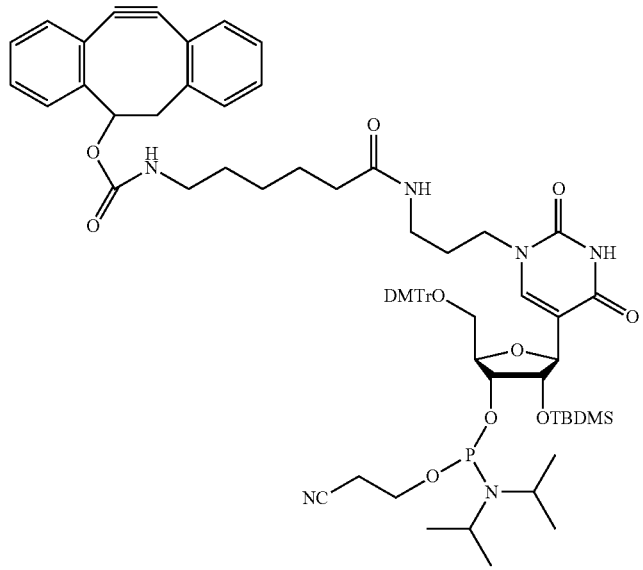

Synthesis of Polymer-siRNA Conjugates Through Metal Free Click Chemistry

Metal free click chemistry is used making different conjugates containing HPMA, polypropyl acrylic acid derivatives, polyketal and other endo-osmolytic polymers with siRNA either in the 3' or 5' end. siRNA can be conjugated to targeting ligands on 3' or 5' end.

Example 26
Synthesis of Azide Group Containing HPMA Copolymer and its Conjugation to Alkyne Functionalized siRNA and Endosomolytic Group
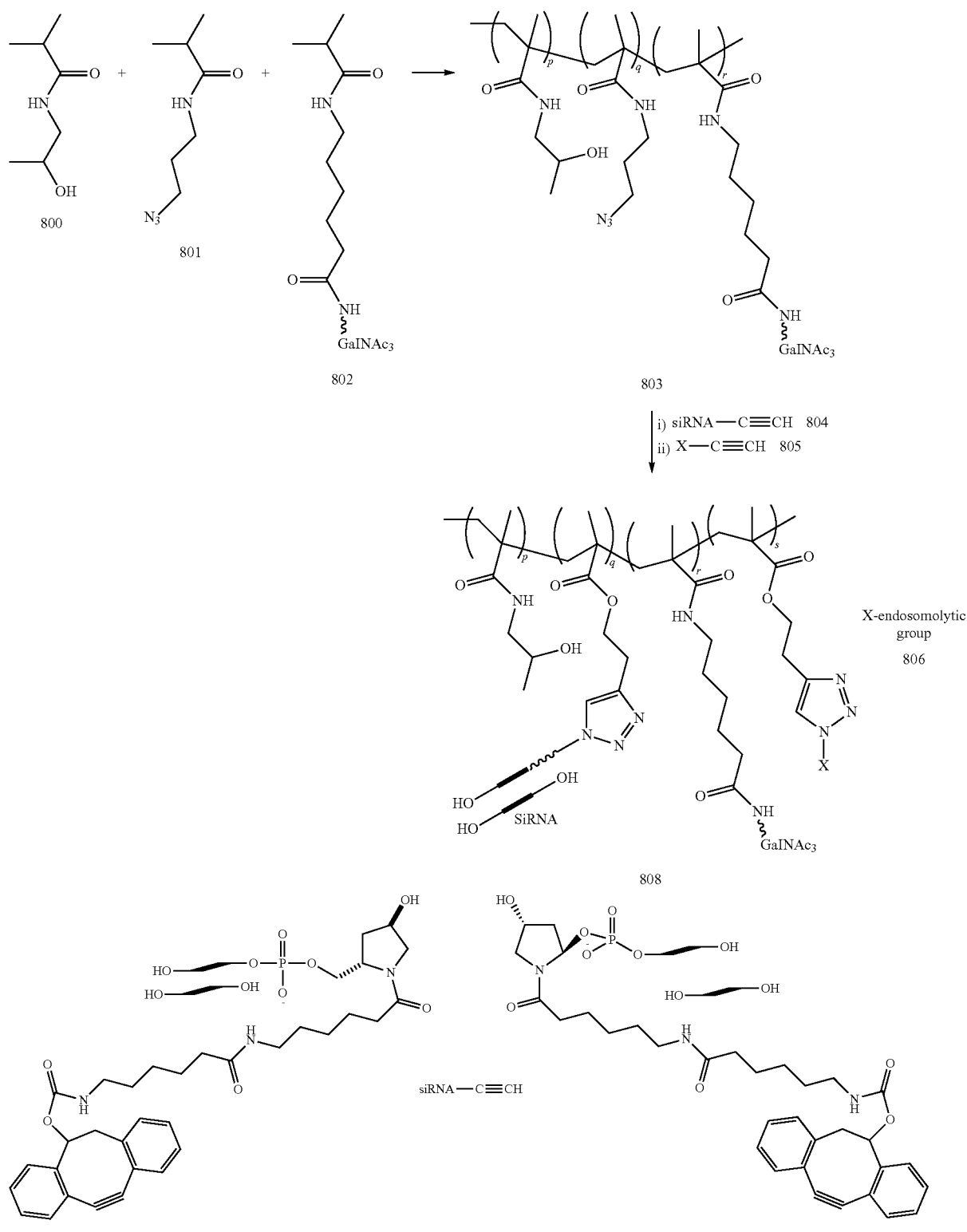

Example 26

Synthesis and Conjugation of HPMA Copolymer Containing Nitrile Oxides and Conjugation with Alkynes by Metal Free Click Chemistry

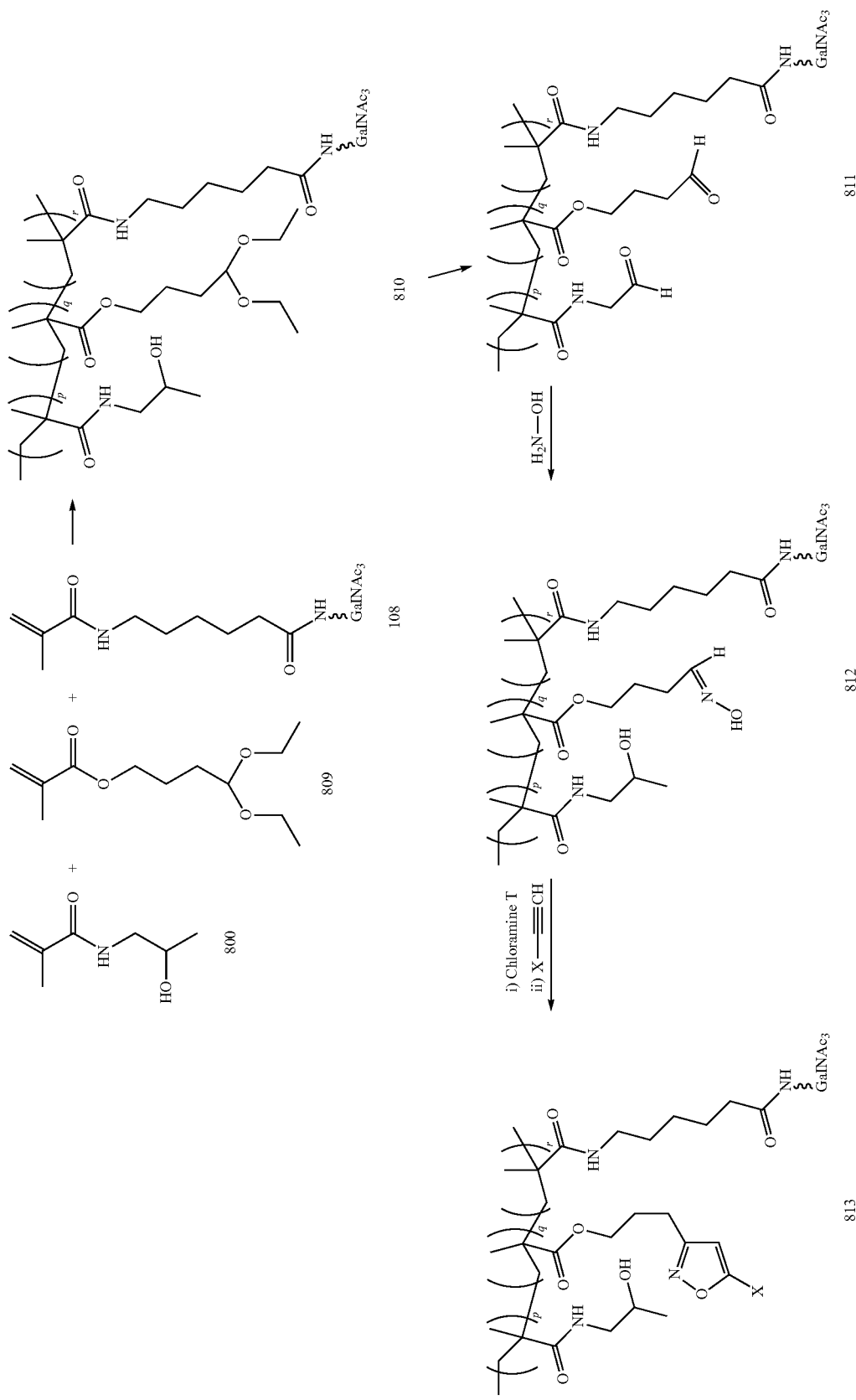

Polymer Characterization

The polymers are characterized for their composition by NMR. The molecular weights (number average molecular weight and weight average molecular weight) and the polydispersity of the polymers are determined by gel permeation chromatography (GPC) coupled with a Multi Angle Laser Light Scattering (MALLS) instrument and a Refractive index (RI) detector. The determined values will be the absolute ones which are not based on polymer standards. The hydrodynamic radii of the polymers are determined from the viscosity detector and light scattering instrument. The size measurements will also be measured using a dynamic light scattering instrument.

Example 27

Synthesis of a Copolymer of HPMA, N-(3-azidopropyl)methacylamide) and GalNAc$_3$-methacrylamide Copolymers are prepared by solution radical copolymerization in DMSO at 60 OC using AIBN (1 wt. %) as initiator and monomers (14 wt. %). N-(3-azidopropyl)methacylamide) is synthesized by the reaction of 1-Azido-3-aminopropane and methacryloyl chloride (Huang, C and Chang F. Macromolecules 2009, 42, 5155-5166). The monomers 100, 101 and 102 (1, 0.25 and 0.125 mmol) mixed with AIBN are dissolved in DMSO, bubbled with argon for 3 min and polymerized in a high-pressure-resistant ampoule at 60 OC for 6 hrs. The crude copolymer is precipitated in dry acetone-ether mixture (1:3, 100 ml). The product is re-precipitated from dry acetone-diethyl ether mixture (3:1, 500 ml), filtered and dried under vacuum.

Example 28

Synthesis of a Copolymer of HPMA, 3,3'-diethoxypropyl methacrylate and GalNAc$_3$-methacrylamide 3,3'-diethoxypropyl methacrylate (809) is prepared by reported procedure (J. Zabransky, M. Houska and J. Kalal, *Makromolekulare Chemie. Macromolecular Chemistry and Physics* 186 (2) (1985), pp. 223-229). The monomers 100, 109 and 102 (1, 0.25 and 0.125 mmol) mixed with AIBN are dissolved in DMSO, bubbled with argon for 3 min and polymerized in a high-pressure-resistant ampoule at 60° C. for 6 hrs. The crude copolymer is precipitated in dry acetone-ether mixture (1:3, 100 ml). The product is re-precipitated from dry acetone-diethyl ether mixture (3:1, 500 ml), filtered and dried under vacuum.

Example 29

Conjugation of siRNA to the Polymer 812

To the alkyne functionalized siRNA (1 mmol) dissolved in ethanol and 4% aqueous NaHCO3 is added the polymer oxime 112 (1 mmol) and chloramines-T (2 mmol). The mixture was stirred at room temperature for 16 hrs. The reaction mixture was purified by dialysis against water and freeze dried

REFERENCES

Rutjes, Floris Petrus Johannes Theodorus; Cornelissen, Johannes Lambertus Maria; Van Berkel, Sander Sebastiaan; Dirks, Antonius Johannes. Process for preparation of trisubstituted 1,2,3-triazoles. PCT Int. Appl. (2008), 63 pp. CODEN: PIXXD2 WO 2008075955 A2 20080626 van Berkel, Sander S.; Dirks, A. J.; Debets, Marjoke F.; van Delft, Floris L.; Cornelissen, Jeroen J. L. M.; Nolte, Roeland J. M.; Rutjes, Floris P. J. T. Metal-free triazole formation as a tool for bioconjugation. ChemBioChem (2007), 8(13), 1504-1508.

A procedure for fast and regioselective copper-free click chemistry at room temperature with p-toluenesulfonyl alkyne. Gouin, Sebastien G.; Kovensky, Jose. Department of Chemistry, Laboratoire des Glucides UMR CNRS 6219, Institut de Chimie de Picardie, Universite de Picardie Jules Verne, Amiens, Fr. Synlett (2009), (9), 1409-1412.

Fast, copper-free click chemistry: A convenient solid-phase approach to oligonucleotide conjugation. Singh, Ishwar; Vyle, Joseph S.; Heaney, Frances. Department of Chemistry, National University of Ireland, Co. Kildare, Maynooth, UK. Chemical Communications (Cambridge, United Kingdom) (2009), (22), 3276-3278.

Bertozzi, Carolyn Ruth; Agard, Nicholas J.; Prescher, Jennifer A.; Baskin, Jeremy Michael; Sletten, Ellen May. Preparation of cyclooctynes and azacyclooctynes for modification of biomolecules in vivo and in vitro by their copper-free strain-promoted [3+2] cycloaddition with azides. U.S. Pat. Appl. Publ. (2009), 62 pp., Cont.-in-part of U.S. Ser. No. 264,463. CODEN: USXXCO US 2009068738 A1 20090312 CAN 150:330128 AN 2009: 291769

De Forest, Cole A.; Polizzotti, Brian D.; Anseth, Kristi S. Sequential click reactions for synthesizing and patterning three-dimensional cell microenvironments. Nature Materials (2009), 8(8), 659-664.

Singh, Ishwar; Zarafshani, Zoya; Lutz, Jean-Francois; Heaney, Frances. Metal-Free "Click" Chemistry: Efficient Polymer Modification via 1,3-Dipolar Cycloaddition of Nitrile Oxides and Alkynes. Macromolecules (Washington, D.C., United States) (2009), 42(15), 5411-5413.

We claim:

1. A compound of formula I, or pharmaceutically acceptable salts thereof:

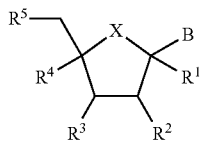

Formula (I)

wherein:

X is O, S, $NR^N$ or $CR^P_2$;

B is independently for each occurrence hydrogen, optionally substituted natural or non-natural nucleobase, optionally substituted triazole or optionally substituted tetrazole; $NH-C(O)-O-C(CH_2B_1)_3$, $NH-C(O)-NH-C(CH_2B_1)_3$; where $B_1$ is halogen, mesylate, $N_3$, CN, optionally substituted triazole or optionally substituted tetrazole;

$R^1$, $R^2$, $R^3$, $R^4$ and $R^5$ are each independently for each occurrence H, $OR^6$, F, $N(R^N)_2$, $N_3$, CN, -J-linker-$N_3$, -J-linker-CN, -J-linker-C≡$R^8$, -J-linker-cycloalkyne, -J-linker-$R^L$, -J-Q-linker-$R^L$, -J-linker-Q-$R^L$, -J-linker-Q-linker-$R^L$, -J-linker-J-Q-$R^L$, or -J-linker-J-Q-linker-$R^L$;

J is independently for each occurrence absent, O, S, $NR^N$, OC(O)NH, NHC(O)O, C(O)NH, NHC(O), NHSO, $NHSO_2$, $NHSO_2NH$, OC(O), C(O)O, OC(O)O, NHC(O)NH, NHC(S)NH, OC(S)NH, O—N=CH, OP(N($R^N)_2$)O, or OP(N($R^N)_2$);

$R^6$ is independently for each occurrence hydrogen, hydroxyl protecting group, optionally substituted alkyl, optionally substituted aryl, optionally substituted cycloalkyl, optionally substituted aralkyl, optionally substituted alkenyl, optionally substituted heteroaryl, polyethyleneglycol (PEG), a phosphate, a diphosphate, a triphosphate, a phosphonate, a phosphonothioate, a phosphonodithioate, a phosphorothioate, a phosphorothiolate, a phosphorodithioate, a phosphorothiolothionate, a phosphodiester, a phosphotriester, an activated phosphate group, an activated phosphite group, a phosphoramidite, a solid support, —P($Z^1$)($Z^2$)—O-nucleoside, —P($Z^1$)($Z^2$)—O-oligonucleotide, —P($Z^1$)($Z^2$)-formula (I), —P($Z^1$)(O-linker-Q-linker-$R^L$)—O-nucleoside, P($Z^1$)(O-linker-$R^L$)—O-nucleoside, —P($Z^1$)(O-linker-$N_3$)—O-nucleoside, P($Z^1$)(O-linker-CN)—O-nucleoside, P($Z^1$)(O-linker-C≡$R^8$)—O-nucleoside, P($Z^1$)(O-linker-cycloalkyne)-O-nucleoside, —P($Z^1$)(O-linker-Q-linker-$R^L$)—O-oligonucleotide, P($Z^1$)(O-linker-$R^L$)—O-oligonucleotide, P($Z^1$)(O-linker-$N_3$)—O-oligonucleotide, —P($Z^1$)(O-linker-CN)—O-oligonucleotide, P($Z^1$)(O-linker-C≡$R^8$)—O-oligonucleotide, P($Z^1$)(O-linker-cycloalkyne)-O-oligonucleotide, —P($Z^1$)(-linker-Q-linker-$R^L$)—O-nucleoside, —P($Z^1$)(-linker-Q-$R^L$)—O-nucleoside, —P($Z^1$)(-linker-$N_3$)—O-nucleoside, P($Z^1$)(-linker-CN)—O-nucleoside, P($Z^1$)(-linker-C≡$R^8$)—O-nucleoside, P($Z^1$)(-linker-cycloalkyne)-O-nucleoside, —P($Z^1$)(-linker-Q-linker-$R^L$)—O-oligonucleotide, —P($Z^1$)(-linker-$R^L$)—O-oligonucleotide, P($Z^1$)(-linker-$N_3$)—O-oligonucleotide, —P($Z^1$)(-linker-CN)—O-oligonucleotide, P($Z^1$)(-linker-C≡$R^8$)—O-oligonucleotide or P($Z^1$)(-linker-cycloalkyne)-O-oligonucleotide;

$R^N$ is independently for each occurrence H, optionally substituted alkyl, optionally substituted alkenyl, optionally substituted alkynyl, optionally substituted aryl, optionally substituted cycloalkyl, optionally substituted aralkyl, optionally substituted heteroaryl or an amino protecting group;

$R^P$ is independently for each occurrence H, optionally substituted alkyl, optionally substituted alkenyl, optionally substituted alkynyl, optionally substituted aryl, optionally substituted cycloalkyl or optionally substituted heteroaryl;

Q is absent or independently for each occurrence or

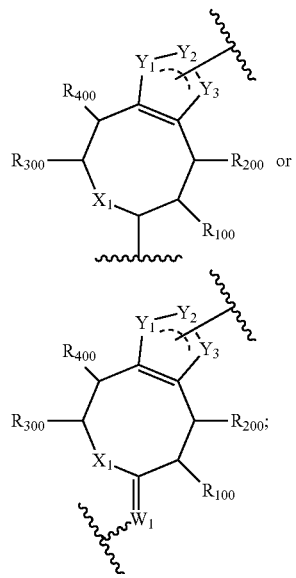

$X_1$ is O, S, $CF_2$, or $CH_2$;
$Y_1$, $Y_2$ and $Y_3$ are each independent $CR^P$, N, O, or S;
$W_1$ is CH or N;
$R_{100}$, $R_{200}$, $R_{300}$ and $R_{400}$ are each independently hydrogen, halogen, $OR^N$, $CR^P_2$, acyl, phosphonyl, sulfonyl;

or alternatively, $R_{100}$ and $R_{200}$ or $R_{300}$ and $R_{400}$ are taken together to form an aryl, substituted aryl, heteroaryl, substituted heteroaryl, cycloalkyl, substituted cycloalkyl, heterocycloalkyl, substituted heterocycloalkyl;

$R^L$ is hydrogen or a ligand;

$R^8$ is N or $CR^9$;

$R^9$ is H, optionally substituted alkyl or silyl; and $Z^1$ and $Z^2$ are each independently for each occurrence O, S or optionally substituted alkyl;

provided that at least one of $R^1$, $R^2$, $R^3$, $R^4$ and $R^5$ is -J-linker-Q-$R^L$, -J-linker-Q-linker-$R^L$, -J-linker-J-Q-$R^L$, or -J-linker-J-Q-linker-$R^L$.

2. The compound of claim 1, represented by formula (VI)

Formula (VI)

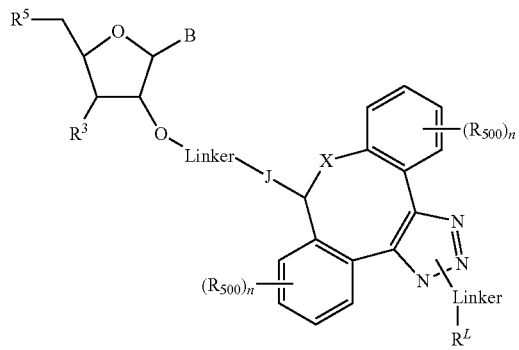

wherein each of $R_{500}$ is independently hydroxyl, halogen, acyl, sulfonyl, phosphonyl, alkyl, haloalkyl, $NO_2$, CN, $N_3$, alkoxy, aminoalkyl, aminodialkyl, and thioalkyl; n is 0-4; each linker can be the same or different; and B, $R^3$, $R^5$, $R^L$, J, and X are as defined in claim 1.

3. The compound of claim 1, represented by formula (VIa)

Formula (VIa)

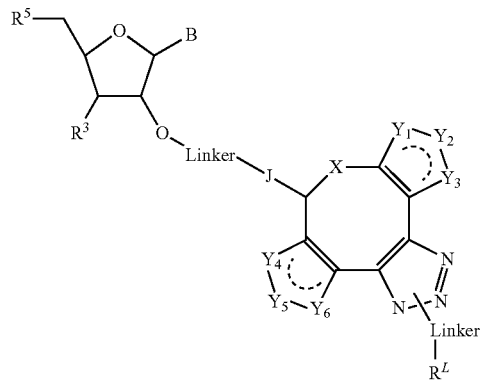

wherein $Y_1$-$Y_6$ are each independently O, S, $NR^N$, or $CR^P{}_2$; each linker can be the same or different; and B, $R^3$, $R^5$, $R^L$, $R^N$, $R^P$, J, and X are as defined in claim 1.

4. The compound of claim 1, where $R^L$ is selected from the group consisting of:

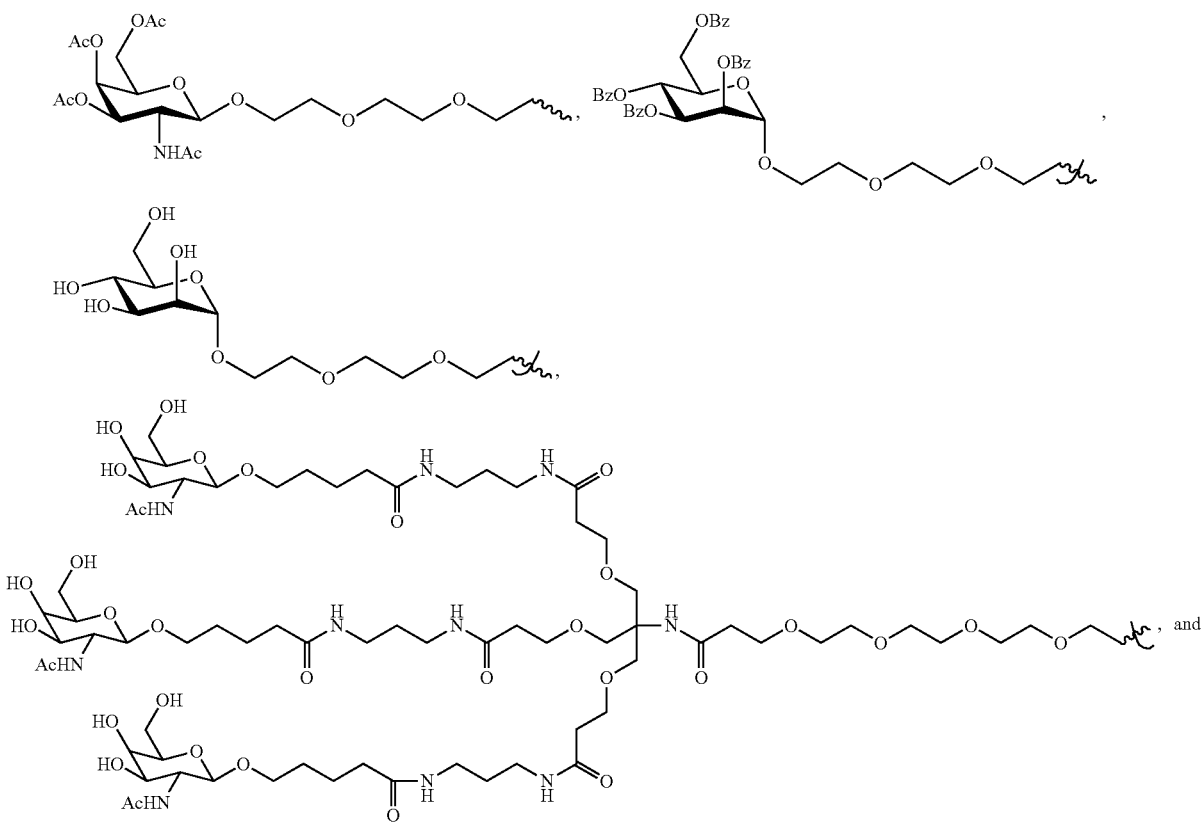

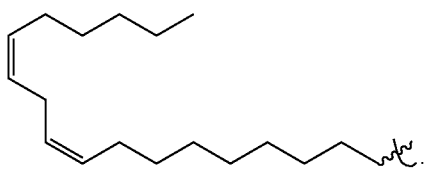

-continued

5. The compound of claim 1, wherein each linker is represented by structure

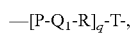

wherein:
P, R and T are each independently for each occurrence absent, CO, NH, O, S, S—S, OC(O), NHC(O), CH$_2$, CH$_2$NH, CH$_2$O; NHCH(R$^a$)C(O), —C(O)—CH(R$^a$)—NH—, —C(O)— (optionally substituted alkyl)-NH—, CH=N—O,

acetal, ketal,

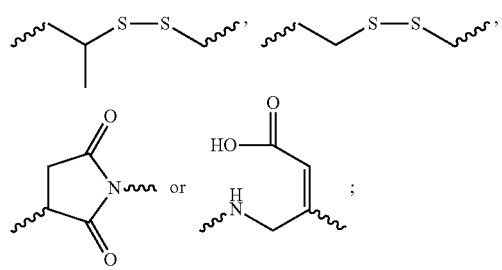

$Q_1$ is independently for each occurrence absent, —(CH$_2$)$_n$—, —C(R$^{100}$)(R$^{200}$)(CH$_2$)$_n$—, —(CH$_2$)$_n$C(R$^{100}$)(R$^{200}$)—, —(CH$_2$CH$_2$O)$_m$CH$_2$CH$_2$—, or —(CH$_2$CH$_2$O)$_m$CH$_2$CH$_2$NH—;
$R^a$ is H or an amino acid side chain;
$R^{100}$ and $R^{200}$ are each independently for each occurrence H, CH$_3$, OH, SH or N(R$^X$)$_2$;

$R^X$ is independently for each occurrence H, methyl, ethyl, propyl, isopropyl, butyl or benzyl;
q is independently for each occurrence 0-20;
n is independently for each occurrence 1-20; and
m is independently for each occurrence 0-50.

6. The compound of claim 1, where least one of $R^1$, $R^2$, $R^3$, $R^4$, and $R^5$ of formula (I) is

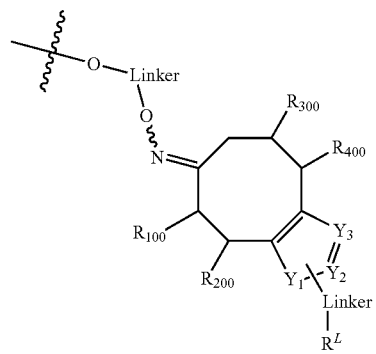

wherein $Y_1$, $Y_2$, $Y_3$, $R_{100}$, $R_{200}$, $R_{300}$, $R_{400}$, and $R^L$ are as previously defined in claim 1.

7. The compound of claim 1, wherein at least one of $R^1$, $R^2$, $R^3$, $R^4$ and $R^5$ is OR$^6$, wherein R$^6$ contains an oligonucleotide.

8. The compound of claim 7, wherein the oligonucleotide is a single-stranded oligonucleotide.

9. The compound of claim 8, wherein the single-stranded oligonucleotide is a single-stranded siRNA.

10. The compound of claim 7, wherein the oligonucleotide is a double-stranded oligonucleotide.

11. The compound of claim 10, wherein the double-stranded oligonucleotide is a double-stranded siRNA.

12. A pharmaceutical composition comprising a compound of claim 1 and a pharmaceutically acceptable excipient.

* * * * *